US007638490B2

(12) United States Patent
Hida et al.

(10) Patent No.: US 7,638,490 B2
(45) Date of Patent: Dec. 29, 2009

(54) METHODS OF AFFECTING FEEDING AND WEIGHT IN MAMMALS BY ADMINISTRATION OF RELAXIN-3

(75) Inventors: Takayuki Hida, Tsukuba (JP); Tomoko Sekiya, Tsukuba (JP); Toru Sawai, Tsukuba (JP); Takashi Seiki, Tsukuba (JP); Eiki Takahashi, Nagareyama (JP); Michiko Kosasa, Tsukuba (JP); Kokichi Harada, Tsukuba (JP); Tohru Arai, Tsukuba (JP)

(73) Assignee: Eisai R&D Managment Co., Ltd., Tokyo-To (JP)

( * ) Notice: Subject to any disclaimer, the term of this patent is extended or adjusted under 35 U.S.C. 154(b) by 198 days.

(21) Appl. No.: 10/588,542

(22) PCT Filed: Feb. 9, 2005

(86) PCT No.: PCT/JP2005/001887

§ 371 (c)(1),
(2), (4) Date: Aug. 7, 2006

(87) PCT Pub. No.: WO2005/075641

PCT Pub. Date: Aug. 18, 2005

(65) Prior Publication Data

US 2007/0054850 A1    Mar. 8, 2007

(30) Foreign Application Priority Data

Feb. 9, 2004   (JP)   .............................. 2004-031591
Dec. 20, 2004  (JP)   .............................. 2004-368509

(51) Int. Cl.
*A61K 38/00*  (2006.01)
*A01N 37/18*  (2006.01)

(52) U.S. Cl. .......................................... 514/12; 514/2
(58) Field of Classification Search .................. None
See application file for complete search history.

(56) References Cited

FOREIGN PATENT DOCUMENTS

| JP | 2002-345468 | 12/2002 |
|---|---|---|
| WO | 00/24891 | 5/2000 |
| WO | 01/48189 A1 | 7/2001 |
| WO | 01/68862 A1 | 9/2001 |
| WO | 02/31111 A2 | 4/2002 |
| WO | 02/061087 A2 | 8/2002 |
| WO | 03/030930 A1 | 4/2003 |
| WO | 2004/082598 A2 | 9/2004 |
| WO | 2004/112575 A2 | 12/2004 |
| WO | 2005/014616 A2 | 2/2005 |
| WO | 2005/075641 A1 | 8/2005 |
| WO | 2005/124361 A2 | 12/2005 |

OTHER PUBLICATIONS

Summerlee AJS et al. Endocrinology 139(5):2322-2328, 1998.*
Sunn N, et al. PNAS 99(3):1701-1706, Feb. 5, 2002.*
M Matsumoto, et al. The novel G-protein coupled receptor SALPR shares sequence similarity with somatostatin and angiotensin receptors. Gene. 248. 183-189. 2000.
S Takeda, et al. Identification of G protein-coupled receptor genes from the human genome sequence. FEBS Letters 520 (2002) 97-101.
R Bathgate, et al. Human relaxin gene 3 (*H3*) and the equivalent mouse relaxin (*M3*) gene. J. Biol. Chem. 277(2). pp. 1148-1157. 2002.
BMC McGowan, et al. Central relaxin-3 administration causes hyperphagia in male wistar rats. Endocrinology. 146 (8). pp. 3295-3300. 2005.
C Liu, et al. INSL5 is a high affinity specific agonist for GPCR142 (GPR100). J. Biol. Chem. 280 (1). pp. 292-300. 2005.
C Liu, et al. Relaxin-3/Insulin-like peptide 5 chimeric peptide, a selective ligand for G protein-coupled receptor (GPCR) 135 and GPCR142 over leucine-rich repeat-containing G protein-coupled receptor 7. Mol. Pharmacol. 67 (1). pp. 231-240. 2005.
K Boels, HC Schaller. Identification and characterisation of GPR100 as a novel human G-protein-coupled bradykinin receptor. British Journal of Pharmacology (2003) 140, 932-938.
P. Sinnayah, et al. Water drinking in rats resulting from intravenous relaxin and its modification by other dispogenic factors. Endocrinology. 140 (11). pp. 5082-5086. 1999.
B Spiegelman, et al. Obesity and the regulation of energy balance. Cell. vol. 104. pp. 531-543. 2001.
C. Liu et al., Identification of relaxin-3/ INSL7 as an endogenous ligand for the orphan G-protein-coupled receptor GPCR135, 2003, J.Biol.Chem., 278(50), p. 50754-64.
C. Liu et al., Identification of relaxin-3/ INSL7 as a ligand for GPCR142, 2003, J.Biol.Chem., 278(50), p. 50765-70.
R.A. Bathgate et al., Relaxin: new peptides, receptors and novel actions, 2003, Trends Endocrinol Metab, 14(5), p. 207-13.
H. Kizawa et al., Production of recombinant human relaxin 3 in AtT20 cells, 2003, Regul. Pept., 113(1-3), pp. 79 to 84.
S. Sudo et al., H3 relaxin is a specifc ligand for LGR7 and activates the receptor by interacting with both the ectodomain and the exoloop 2, 2003, J. Biol.Chem., 278(10), p. 7855-62.

(Continued)

*Primary Examiner*—Robert Landsman
(74) *Attorney, Agent, or Firm*—Wenderoth, Lind & Ponack, L.L.P.

(57) ABSTRACT

Relaxin-3 is found to have feeding-stimulating activity, body weight increasing activity, and fat weight increasing activity when intracerebroventricularly administered to rats through observation of amount of feeding, body weight and fat weight after administration of relaxin-3. This invention includes: a polypeptide having useful effects in stimulating feeding, increasing body weight, and fattening; a therapeutic agent containing the polypeptide; a method of screening for a compound, a substance, or a salt thereof which activates or suppresses a receptor of the polypeptide; a kit for screening; and an agent with a substance which inhibits expression of the polypeptide, such as a feeding-suppressing agent, a therapeutic agent for the treatment of obesity, and a therapeutic agent for the treatment of diabetes.

5 Claims, 11 Drawing Sheets

OTHER PUBLICATIONS

C.S. Samuel et al., Physiological or pathological—a role for relaxin in the cardiovascular system?, 2003, Curr.Opin. Pharmacol., 3(2), p. 152-8.

International Search Report issued Aug. 29, 2007 in the International (PCT) Application of which the present application is the U.S. National Stage.

Liu, et al., "Identification of Relaxin-3/INSL7 as an Endogenous Ligand for the Orphan G-protein-coupled Receptor GPCR135," The Journal of Biological Chemistry, vol. 278, No. 50, Dec. 12, 2003, pp. 50754-50764.

* cited by examiner

METHODS OF AFFECTING FEEDING AND WEIGHT IN MAMMALS BY ADMINISTRATION OF RELAXIN-3

This application is a U.S. national stage of International Application No. PCT/JP05/01887, filed Feb. 9, 2005, which is incorporated herein in its entirety.

FIELD OF THE INVENTION

The present invention relates to a polypeptide having useful effects in stimulating feeding (eating), increasing body weight, and fattening; a therapeutic agent containing said polypeptide; a method of screening for a compound, a substance, or a salt thereof which activates or suppresses a receptor of said polypeptide; a kit for said screening; and an agent which comprises a substance which inhibits expression of said polypeptide, such as a feeding-suppressing agent, a therapeutic agent for the treatment of obesity, and a therapeutic agent for the treatment of diabetes.

BACKGROUND ART

Feeding (eating) is a behavior essential for animals to survive. Obesity is considered to be a result of failure to control or balance feeding and energy consumption in our current society in the age of satiation. Since the obesity is a risk factor for lifestyle diseases and various other diseases, social interest in it has been increasing. Although basic therapies to improve the balance between feeding and energy consumption, such as diet therapy and exercise therapy, have become available, the number of patients and candidates for obesity is currently increasing. Recently, pharmaceutical agents for suppressing nutritional absorption in peripheral tissues and pharmaceutical agents for decreasing the amount of feeding by acting on the central nervous system have been developed; however, development of effective and safe pharmaceutical agents for suppressing the amount of feeding as agents to treat obesity is desired.

It has been gradually revealed that feeding behavior is controlled by a cycle with a direction from the cerebral central nerve and a feedback from the peripheral tissue, whereby a further direction is sent from the central nervous system. Thus, research focusing on the feeding-controlling mechanism in the brain, which plays a major role, has been flourishing. By research using an animal in which a specific region of the brain is destroyed and functional analyses using neuropeptides or neurotransmitters, it has been gradually revealed that a hypothalamus region plays an important role in the feeding behavior. Further, a number of neurotransmitters, neuropeptides and receptors for them are expressed in the hypothalamus and thus their correlation with feeding behavior has been shown. For example, there have been reported that neuropeptide Y, agouti gene-related peptide and the like which are present in the arcuate nucleus of the hypothalamus are involved in feeding-stimulation and that melanocortin which is present in the same region and corticotropin-releasing hormone and thyrotropin-releasing hormone which are released from the paraventricular nucleus of the hypothalamus are involved in feeding-suppression (non-patent reference 1). However, as to the complicated nervous network to control feeding, much remains unrevealed and new findings regarding novel neurotransmitters and their locations are still appearing.

Physiologically active substances which are involved in controlling feeding behavior, such as neurotransmitters and neuropeptides, exhibit their function via specific receptors present in the cell membrane. Of these receptors, receptors which have a structure to penetrate the cell membrane 7 times and are coupled with the G protein trimer in the cells are particularly classified as G-protein-coupled receptors (GPCRs). Upon binding with specific ligands, the GPCRs transmit signals into the cells to activate or suppress the cells and thus play an important role in expressing functions in various organs. Therefore, agonists which activate GPCRs and antagonists which suppress GPCRs have been used as medicines. Of receptors classified into GPCRs, many for which no specific ligand has been identified are known and called orphan GPCRs. The orphan GPCRs have a potential to become a target for novel therapeutic agents, and thus identification of their ligands and research on substances to activate or suppress their function have been in progress. It is extremely important in developing new medicines to elucidate functions of the receptors and their ligands by administering the identified ligands or substances to the body.

In recent years, enrichment of the genetic sequence information makes it possible to predict and identify an unknown peptide or protein as a novel GPCR ligand by deducing its homology and regularity based on sequences of known proteins or peptides. Relaxin, a member of the insulin/relaxin family, is a secretory hormone produced by the corpus luteum or the placenta and has long been known to have functions involved in the maintenance of pregnancy and the delivery. As another function, for example, stimulation of water intake by relaxin-2 intravenously administered in rats has been reported (non-patent reference No. 2); however, correlation between relaxin and feeding behavior has not been known. A protein encoded by a DNA sequence which is newly identified by a gene sequence database based on the base sequence of DNA encoding relaxin is a polypeptide called relaxin-3/INSL7 (patent reference No. 1). Relaxin-3 thus found has been reported to activate cells with an increase in intracellular cyclic AMP (cAMP) of THP-1 cells of the immune system (patent reference No. 2, non-patent reference No. 3). It has later been suggested that relaxin-3, along with relaxin 2, is one of ligands which bind LGR7, a GPCR (non-patent reference No. 4). LGR7 is expressed in the brain and peripheral tissues and has been so far suggested to be involved in development of reproductive organs, pregnancy, and delivery; however, its correlation with feeding has not clearly been understood.

Recently it has been reported that a ligand for GPCRs for which no ligand in the body has been identified, i.e., a receptor called SALPR (GPCR135) and a receptor called GPR100 (hGPCR11, GPCR142), is relaxin-3 (non-patent references Nos. 5 and 6; patent reference No. 3). Further, patent references Nos. 4 to 7 also include descriptions related to these receptors. SALPR is known to locate in the brain (non-patent reference No. 7) and in particular reported to locate in the paraventricular nucleus and the supraoptic nucleus of the hypothalamus (patent reference No. 3; non-patent reference No. 6). On the other hand, GPR100 has been reported to be a receptor which is systemically expressed (non-patent references Nos. 8 and 9); however, its function remains unknown.

On the other hand, relaxin-3 has been reported to be present in the area called the pons in the brain (non-patent reference No. 6) and it has been thought that relaxin-3 may exhibit some functions in the central nervous system as an intracerebral peptide; however, there has been no report on whether relaxin-3 controls feeding or whether relaxin-3 is involved in body weight control. Further, whether relaxin-3 is related to obesity has also not been known.

Patent reference No. 1: WO 01/068862
Patent reference No. 2: Japanese Patent Laid-open No. 2002-345468
Patent reference No. 3: WO 2004/082598
Patent reference No. 4: WO 00/24891
Patent reference No. 5: WO 01/48189
Patent reference No. 6: WO 02/31111
Patent reference No. 7: WO 02/61087
Non-patent reference No. 1: Spiegelman et al., Cell, 104, p. 541-543, 2001
Non-patent reference No. 2: Sinnayah et al., Endocrinology, 140, p. 5082-5086, 1999
Non-patent reference No. 3: Bathgate et al., J. Biol. Chem., 277, p. 1148-1157, 2002
Non-patent reference No. 4: Sudo et al., J. Biol. Chem., 278, p. 7855-7862, 2003
Non-patent reference No. 5: Takeda et al., FEBS Letter, 520, p. 97-101, 2002
Non-patent reference No. 6: Liu et al., J. Biol. Chem., 278, p. 50754-50764, 2003
Non-patent reference No. 7: Matsumoto et al., Gene, 248, p. 183-189, 2000
Non-patent reference No. 8: Liu et al., J. Biol. Chem., 278, p. 50765-50770, 2003
Non-patent reference No. 9: Boels et al., Br. J. Pharmacol., 140, p. 932-938, 2003

DISCLOSURE OF THE INVENTION

Problems to be Solved by the Invention

The present invention relates to a polypeptide having useful effects in stimulating feeding (aperitive), increasing body weight, and fattening; a therapeutic agent containing said polypeptide; a method of screening for a compound, a substance, or a salt thereof which activates or suppresses a receptor of said polypeptide; a kit for said screening; and an agent which comprises a substance which inhibits expression of said polypeptide, such as a feeding-suppressing agent, a therapeutic agent for the treatment of obesity, and a therapeutic agent for the treatment of diabetes.

Means to Solve the Problems

As a result of intensive research to solve the above-mentioned problems, the present inventors have found that relaxin-3 has a feeding-stimulating (aperitive) activity, by intracerebroventricularly administering relaxin-3 to rats and observing the amount of feeding after administration. The inventors also found that the blood leptin concentration known as an index for a body fat increase was increased, by measuring blood samples from rats after single administration of relaxin-3 to the rats. Further, when relaxin-3 was continuously administrated into the cerebroventricle in rats, significant increases in feeding and body weight gain were observed in the relaxin-3 administration group as compared to the control vehicle administration group. No difference in locomotor activity was observed between the continuous relaxing-3 administration group and the control group. These results showed for the first time that relaxin-3 has a body weight increasing activity as well as a feeding-stimulating activity. Further, in the rats whose body weight was increased by the administration of relaxin-3, increases in fat weight and the blood leptin concentration, which correlates with body fat content, were observed. The insulin concentration, which relates to diabetes, was also increased. Thus, relaxin-3 is considered to be a polypeptide which has a feeding-stimulating activity, a body weight increasing activity and a fattening activity. The present invention has been completed based on these findings.

Namely, the present invention relates to (1) a feeding-stimulating agent, comprising a polypeptide comprising the amino acid sequence represented by SEQ ID NO: 2, a functionally equivalent modified polypeptide thereof, or a polypeptide consisting of an amino acid sequence having 70% or more homology to the amino acid sequence of a polypeptide comprising the amino acid sequence represented by SEQ ID NO: 2, or a salt thereof;

(2) a agent for increasing body weight, comprising a polypeptide comprising the amino acid sequence represented by SEQ ID NO: 2, a functionally equivalent modified polypeptide thereof, or a polypeptide consisting of an amino acid sequence having 70% or more homology to the amino acid sequence of a polypeptide comprising the amino acid sequence represented by SEQ ID NO: 2, or a salt thereof;

(3) an agent for increasing fat weight, comprising a polypeptide comprising the amino acid sequence represented by SEQ ID NO: 2, a functionally equivalent modified polypeptide thereof, or a polypeptide consisting of an amino acid sequence having 70% or more homology to the amino acid sequence of a polypeptide comprising the amino acid sequence represented by SEQ ID NO: 2, or a salt thereof;

(4) a method of screening for a compound which stimulates feeding or a salt thereof, comprising the steps of (A) contacting a test substance with a relaxin-3 receptor, a cell containing a relaxin-3 receptor, or a membrane fraction of said cell, and (B) measuring a cell-stimulating activity via the relaxin-3 receptor;

(5) a method of screening for a compound which stimulates or suppresses feeding or a salt thereof, comprising the step of (A) contacting a polypeptide comprising the amino acid sequence represented by SEQ ID NO: 2, a functionally equivalent modified polypeptide thereof, or a polypeptide consisting of an amino acid sequence having 70% or more homology to the amino acid sequence of a polypeptide comprising the amino acid sequence represented by SEQ ID NO: 2, or a salt thereof, and a test substance with a relaxin-3 receptor, a cell which contains a relaxin-3 receptor, or a membrane fraction of said cell;

(6) the method of screening for a compound which stimulates or suppresses feeding or a salt thereof according to (5) above, wherein it comprises the step of (B) measuring a cell-stimulating activity via the relaxin-3 receptor;

(7) the screening method according to (4), (5), or (6) above, wherein the relaxin-3 receptor is SALPR or its partial polypeptide;

(8) the screening method according to (7) above, wherein SALPR is a polypeptide comprising the amino acid sequence represented by SEQ ID NO: 4;

(9) a kit for screening for a compound which stimulates feeding or a salt thereof, comprising the steps of (A) contacting a test substance with a relaxin-3 receptor, a cell which contains a relaxin-3 receptor, or a membrane fraction of said cell, and (B) measuring a cell-stimulating activity via the relaxin-3 receptor;

(10) a kit for screening for a compound which stimulates or suppresses feeding or a salt thereof, comprising the step of (A) contacting a polypeptide comprising the amino acid sequence represented by SEQ ID NO: 2, a functionally equivalent modified polypeptide thereof, or a polypeptide consisting of an amino acid sequence having 70% or more homology to the amino acid sequence of a polypeptide comprising the amino acid sequence represented by SEQ ID NO: 2, or a salt thereof, and a test substance with a relaxin-3 receptor, a cell which contains a relaxin-3 receptor, or a membrane fraction of said cell;

(11) the kit for screening for a compound which stimulates or suppresses feeding or a salt thereof according to (10) above, wherein it comprises the step of (B) measuring a cell-stimulating activity via the relaxin-3 receptor;

(12) the screening kit according to (9), (10), or (11) above, wherein the relaxin-3 receptor is SALPR or its partial polypeptide;

(13) the screening kit according to (12) above, wherein SALPR is a polypeptide comprising the amino acid sequence represented by SEQ ID NO: 4;

(14) a therapeutic agent for the treatment of a disease which requires weight gain, comprising a polypeptide comprising the amino acid sequence represented by SEQ ID NO: 2, a functionally equivalent modified polypeptide thereof, or a polypeptide consisting of an amino acid sequence having 70% or more homology to the amino acid sequence of a polypeptide comprising the amino acid sequence represented by SEQ ID NO: 2, or a salt thereof;

(15) the agent according to (14) above, wherein said disease is anorexia or cachexia;

(16) a method of screening for a compound which increases body weight or a salt thereof, comprising the steps of (A) contacting a test substance with a relaxin-3 receptor, a cell containing a relaxin-3 receptor, or a membrane fraction of said cell, and (B) measuring a cell-stimulating activity via the relaxin-3 receptor;

(17) a method of screening for a compound which increases or decreases body weight or a salt thereof, comprising the step of (A) contacting a polypeptide comprising the amino acid sequence represented by SEQ ID NO: 2, a functionally equivalent modified polypeptide thereof, or a polypeptide consisting of an amino acid sequence having 70% or more homology to the amino acid sequence of a polypeptide comprising the amino acid sequence represented by SEQ ID NO: 2, or a salt thereof, and a test substance with a relaxin-3 receptor, a cell which contains a relaxin-3 receptor, or a membrane fraction of said cell;

(18) the method of screening for a compound which increases or decreases body weight or a salt thereof according to (17) above, wherein it comprises the step of (B) measuring a cell-stimulating activity via the relaxin-3 receptor;

(19) the screening method according to (16), (17), or (18) above, wherein the relaxin-3 receptor is SALPR or its partial polypeptide;

(20) the screening method according to (19) above, wherein SALPR is a polypeptide comprising the amino acid sequence represented by SEQ ID NO: 4;

(21) a kit for screening for a compound which increases body weight or a salt thereof, comprising the steps of (A) contacting a test substance with a relaxin-3 receptor, a cell containing a relaxin-3 receptor, or a membrane fraction of said cell, and (B) measuring a cell-stimulating activity via the relaxin-3 receptor;

(22) a kit for screening for a compound which increases or decreases body weight or a salt thereof, comprising the step of (A) contacting a polypeptide comprising the amino acid sequence represented by SEQ ID NO: 2, a functionally equivalent modified polypeptide thereof, or a polypeptide consisting of an amino acid sequence having 70% or more homology to the amino acid sequence of a polypeptide comprising the amino acid sequence represented by SEQ ID NO: 2, or a salt thereof, and a test substance with a relaxin-3 receptor, a cell which contains a relaxin-3 receptor, or a membrane fraction of said cell;

(23) the kit for screening for a compound which increases or decreases body weight or a salt thereof according to (22) above, wherein it comprises the step of (B) measuring a cell-stimulating activity via the relaxin-3 receptor;

(24) the screening kit according to (21), (22), or (23) above, wherein the relaxin-3 receptor is SALPR or its partial polypeptide;

(25) the screening kit according to (24) above, wherein SALPR is a polypeptide comprising the amino acid sequence represented by SEQ ID NO: 4;

(26) a method of screening for a compound involved in the control of obesity or a salt thereof, comprising the steps of (A) contacting a test substance with a relaxin-3 receptor, a cell containing a relaxin-3 receptor, or a membrane fraction of said cell, and (B) measuring a cell-stimulating activity via the relaxin-3 receptor;

(27) a method of screening for a compound involved in the control of obesity or a salt thereof, comprising the step of (A) contacting a polypeptide comprising the amino acid sequence represented by SEQ ID NO: 2, a functionally equivalent modified polypeptide thereof, or a polypeptide consisting of an amino acid sequence having 70% or more homology to the amino acid sequence of a polypeptide comprising the amino acid sequence represented by SEQ ID NO: 2, or a salt thereof, and a test substance with a relaxin-3 receptor, a cell which contains a relaxin-3 receptor, or a membrane fraction of said cell;

(28) the method of screening for a compound involved in the control of obesity or a salt thereof according to (27) above, wherein it comprises the step of (B) measuring a cell-stimulating activity via the relaxin-3 receptor;

(29) the screening method according to (26), (27), or (28) above, wherein the relaxin-3 receptor is SALPR or its partial polypeptide;

(30) the screening method according to (29) above, wherein SALPR is a polypeptide comprising the amino acid sequence represented by SEQ ID NO: 4;

(31) a kit for screening for a compound involved in the control of obesity or a salt thereof, comprising the steps of (A) contacting a test substance with a relaxin-3 receptor, a cell containing a relaxin-3 receptor, or a membrane fraction of said cell, and (B) measuring a cell-stimulating activity via the relaxin-3 receptor;

(32) a kit for screening for a compound involved in the control of obesity or a salt thereof, comprising the step of (A) contacting a polypeptide comprising the amino acid sequence represented by SEQ ID NO: 2, a functionally equivalent modified polypeptide thereof, or a polypeptide consisting of an amino acid sequence having 70% or more homology to the amino acid sequence of a polypeptide comprising the amino acid sequence represented by SEQ ID NO: 2, or a salt thereof, and a test substance with a relaxin-3 receptor, a cell which contains a relaxin-3 receptor, or a membrane fraction of said cell;

(33) the kit for screening for a compound involved in the control of obesity or a salt thereof according to (32) above, wherein it comprises the step of (B) measuring a cell-stimulating activity via the relaxin-3 receptor;

(34) the screening method according to (31), (32), or (33) above, wherein the relaxin-3 receptor is SALPR or its partial polypeptide;

(35) the screening kit according to (34) above, wherein SALPR is a polypeptide comprising the amino acid sequence represented by SEQ ID NO: 4;

(36) an agent for suppressing feeding, comprising a compound having an SALPR-inhibiting activity;

(37) the agent according to (36) above, wherein the compound having an SALPR-inhibiting activity is a compound obtained by the screening method of (7) or (8) above.

(38) an agent for reducing body weight, comprising a compound having an SALPR-inhibiting activity;

(39) the agent according to (38) above, wherein the compound having an SALPR-inhibiting activity is a compound obtained by the screening method of (19) or (20) above;

(40) an agent for reducing fat weight, comprising a compound having an SALPR-inhibiting activity;

(41) the agent according to (40) above, wherein the compound having an SALPR-inhibiting activity is a compound obtained by the screening method of (29) or (30) above;

(42) a therapeutic agent for the treatment of obesity, comprising a compound having an SALPR-inhibiting activity;

(43) the agent according to (42) above, wherein the compound having an SALPR-inhibiting activity is a compound obtained by the screening method of anyone of (19), (20), (29), and (30) above;

(44) a therapeutic agent for the treatment of diabetes, comprising a compound having an SALPR-inhibiting activity;

(45) the agent according to (44) above, wherein the compound having an SALPR-inhibiting activity is a compound obtained by the screening method of any one of (19), (20), (29), and (30) above;

(46) the agent according to any one of (36) to (45) above, wherein SALPR is a polypeptide comprising the amino acid sequence represented by SEQ ID NO: 4;

(47) a method of screening for a compound to stimulate or suppress feeding or a salt thereof, comprising the steps of administering a compound which acts on a relaxin-3 receptor to a human or a non-human organism and then measuring the amount of feeding after administration;

(48) the method according to (47) above, wherein the compound which acts on a relaxin-3 receptor is a compound obtained by the method of any one of (4) to (8) above;

(49) a method of screening for a compound which increases or decreases body weight or a salt thereof, comprising the steps of administering a compound which acts on a relaxin-3 receptor to a human or a non-human organism and then measuring body weight after administration;

(50) the method according to (49) above, wherein the compound which acts on a relaxin-3 receptor is a compound obtained by the method of any one of (16) to (20) above;

(51) a method of screening for a compound involved in the control of obesity or a salt thereof, comprising the steps of administering a compound which acts on a relaxin-3 receptor to a human or a non-human organism and then measuring indices of obesity after administration; and

(52) the method according to (51) above, wherein the compound which acts on a relaxin-3 receptor is a compound obtained by the method of any one of (26) to (30) above.

BRIEF DISCRIPTION OF THE DRAWINGS

Figure 3:
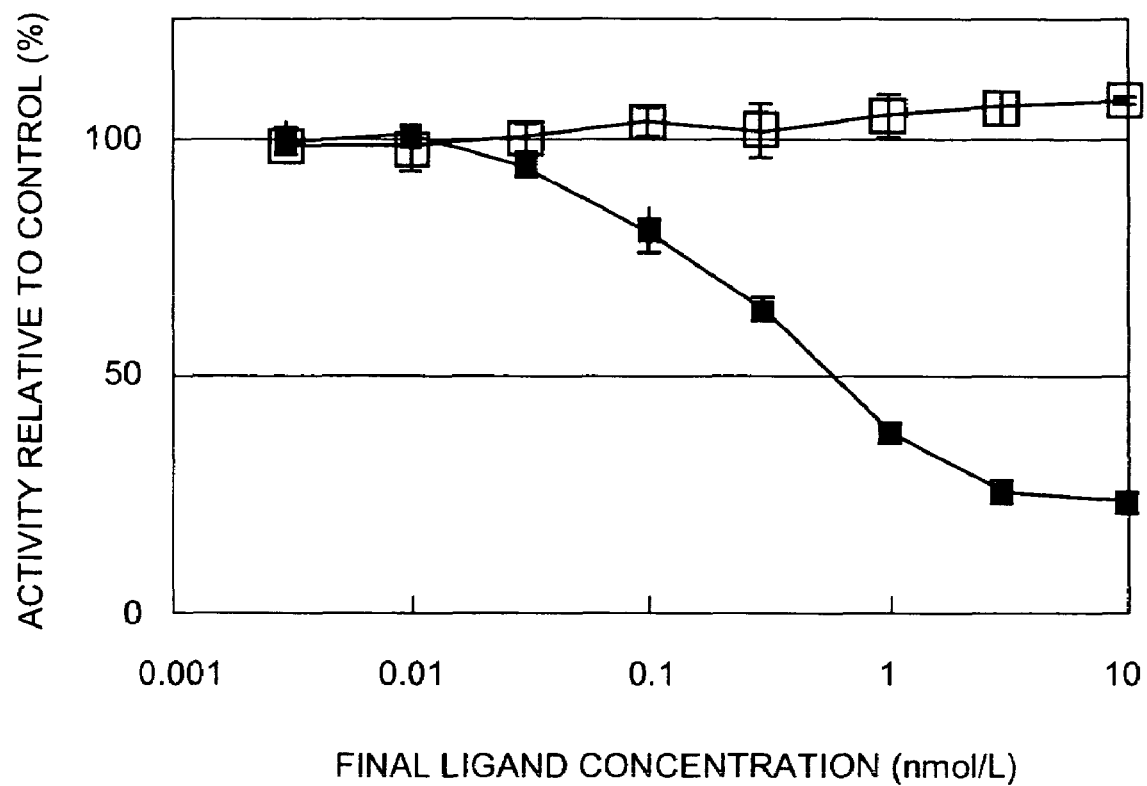

FIG. 3 shows specific dose-dependent suppression by relaxin-3 of transcription activity which is increased by the addition of forskolin in SE302 cells in which SALPR is expressed. Black squares show the case where relaxin-3 was added. White squares show the case where insulin was added. The numbers on the horizontal axis show the final concentration (nmol/L) of each ligand added. The numbers on the vertical axis show the relative activity calculated by setting alkaline phosphatase activity of cellular supernatant with the addition of forskolin at 1 µmol/L to be 100 and with no forskolin to be 0. Each point shows the average (N=3) and standard deviation.

Figure 4:
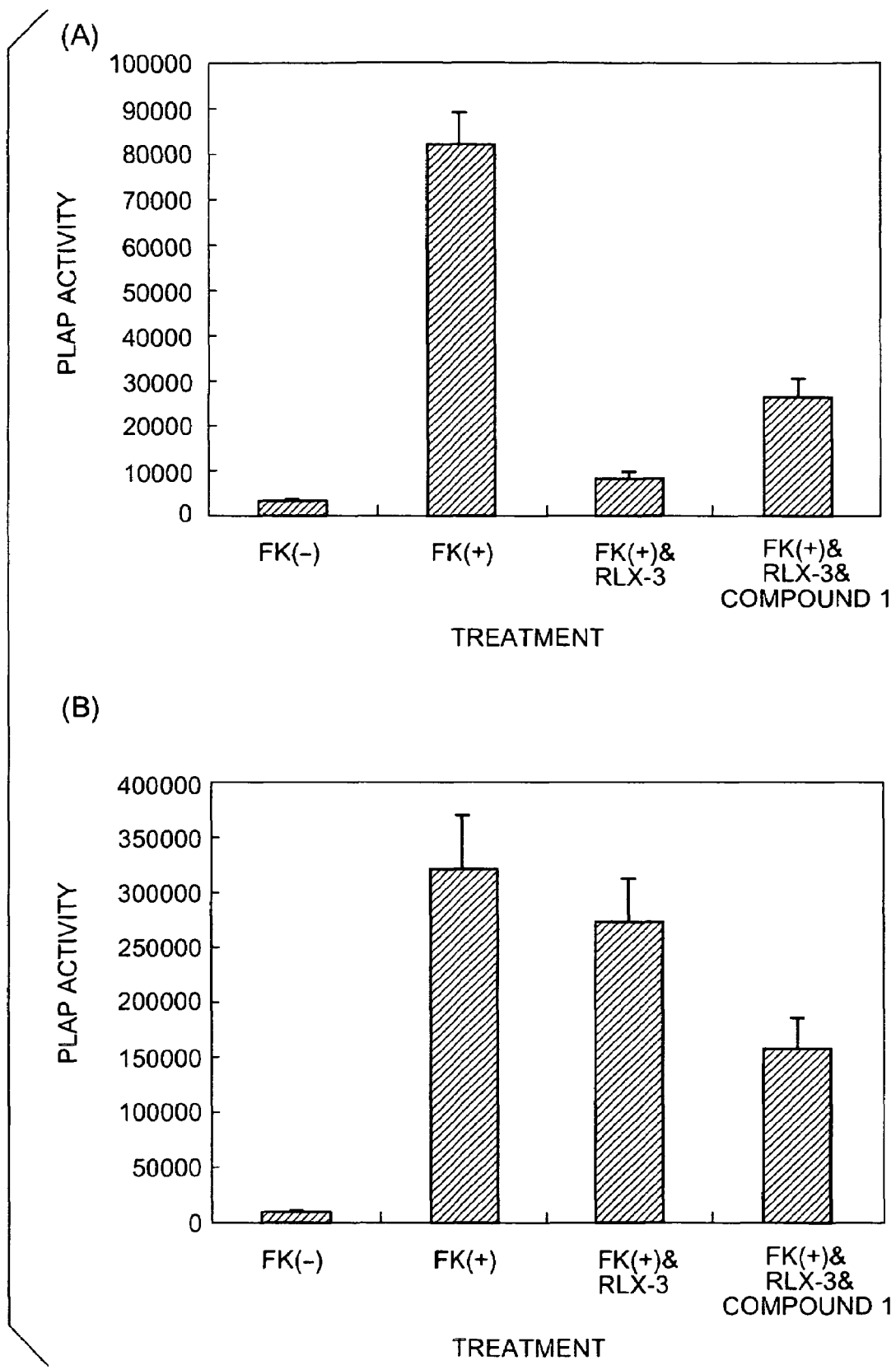

FIG. 4A-B shows the evaluation (screening) for relaxin-3 antagonistic compounds using SALPR-SE302 cells. Panel A is the case where SALPR-SE302 cells were used. Panel B is the case where SE302 cells were used. In this figure, FK(−) shows the forskolin non-treatment group; FK(+), the 3 µM forskolin treatment group; FK(+)&RLX-3, the forskolin and 3 nM relaxin-3 treatment group; and FK(+)&RLX -3 &compound 1, the group treated with a combination of forskolin, relaxin-3, and compound 1.

Figure 5:
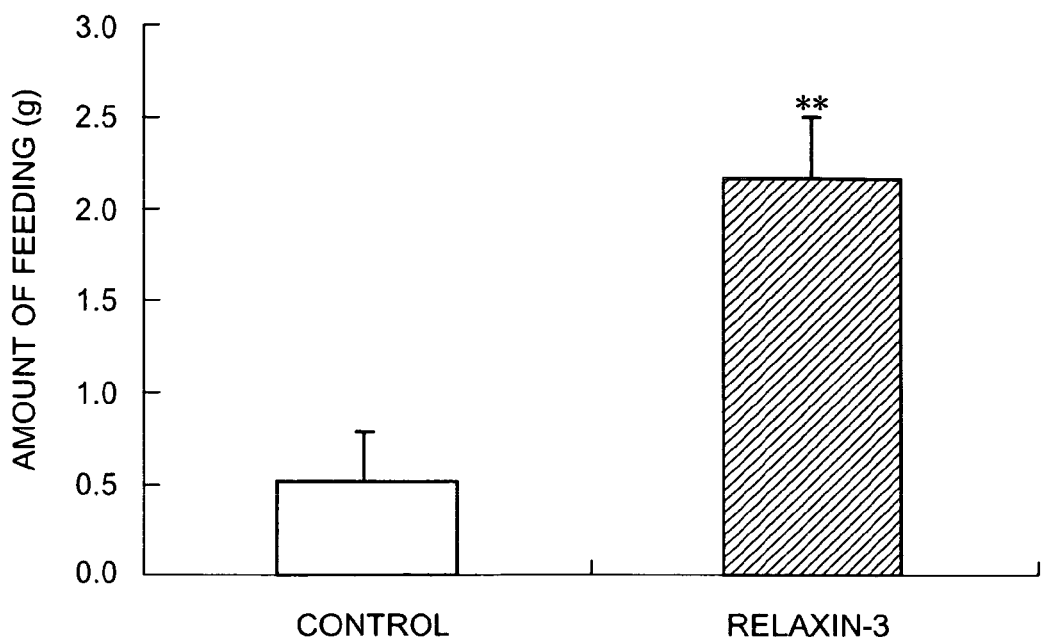

FIG. 5 shows the effect of a single intracerebroventricular administration of relaxin-3 to normal rats on the amount of feeding. The white rectangular bar shows the vehicle administration group (control) and the black rectangular bar shows the relaxin-3 administration group. The vertical axis shows the mean and standard error of the amount of feeding (g) per animal in each group.

Figure 6:
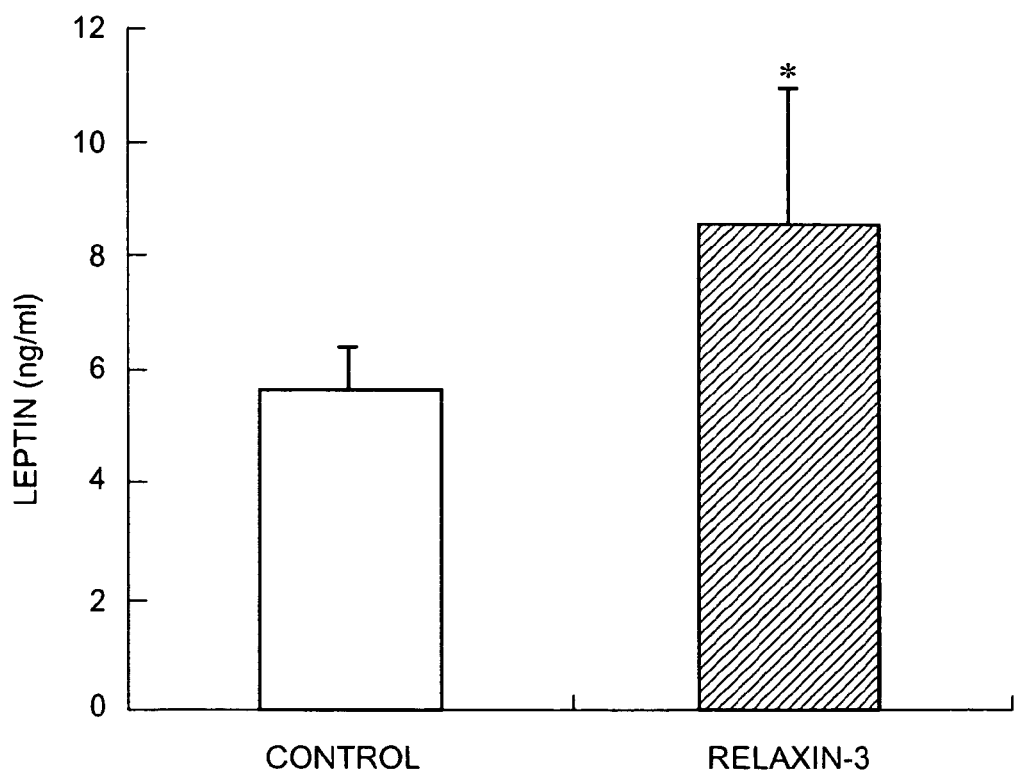

FIG. 6 shows the effect of a single intracerebroventricular administration of relaxin-3 to normal rats on the blood leptin concentration. The white rectangular bar shows the vehicle administration group (control) and the black rectangular bar shows the relaxin-3 administration group. The vertical axis shows the mean and standard deviation of the blood leptin concentration (ng/ml) in each group.

Figure 7:
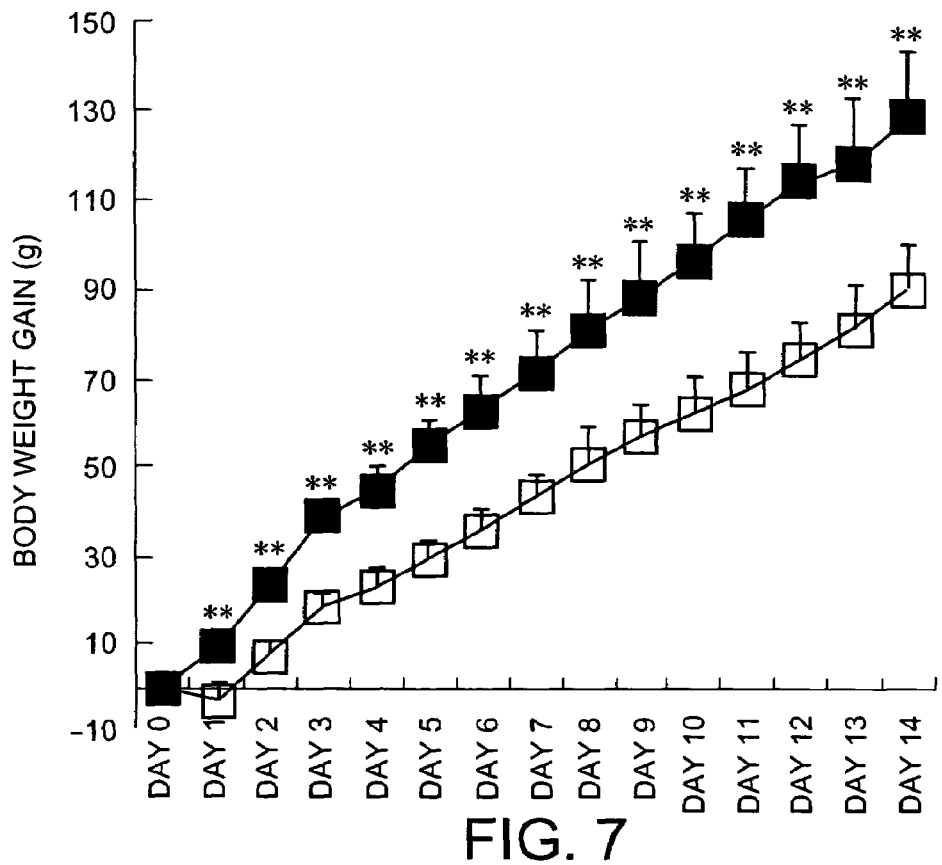

FIG. 7 shows the effect of a chronic intracerebroventricular administration of relaxin-3 to normal rats on the body weight gain. The white squares show the vehicle administration group (control) and the black squares show the relaxin-3 administration group. The vertical axis shows the mean and standard deviation of the body weight gain (g) per animal in each group.

Figure 8:
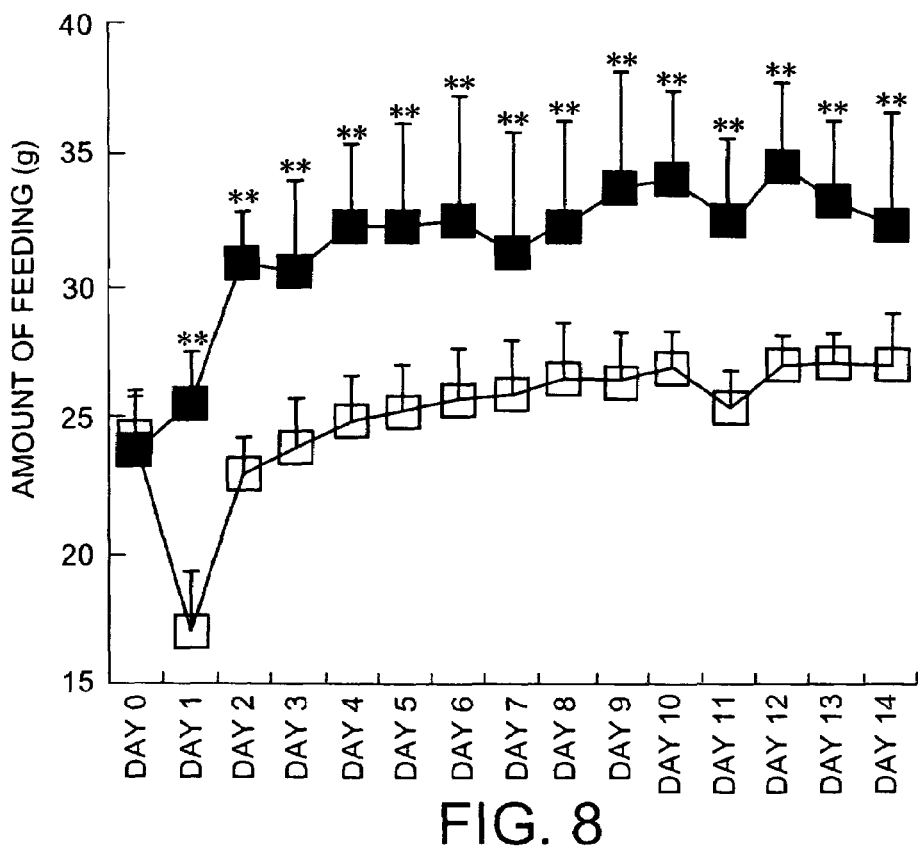

FIG. 8 shows the effect of a chronic intracerebroventricular administration of relaxin-3 to normal rats on the amount of feeding. The white squares show the vehicle administration group (control) and the black squares show the relaxin-3 administration group. The vertical axis shows the mean and standard deviation of the amount of feeding (g) per animal in each group.

Figure 9:
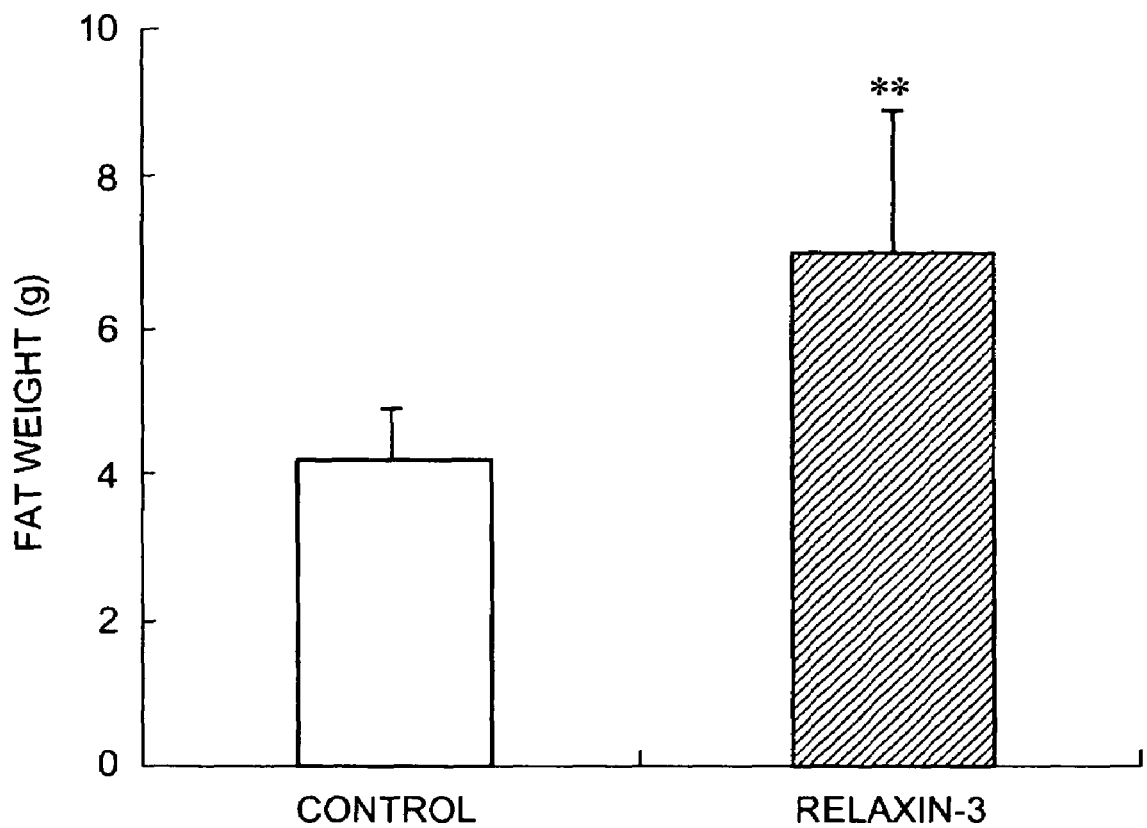

FIG. 9 shows the effect of a chronic intracerebroventricular administration of relaxin-3 to normal rats on the epididymal fat weight. The white rectangular bar shows the vehicle administration group (control) and the black rectangular bar shows the relaxin-3 administration group. The vertical axis shows the mean and standard deviation of the fat weight (g) per animal in each group.

Figure 10:
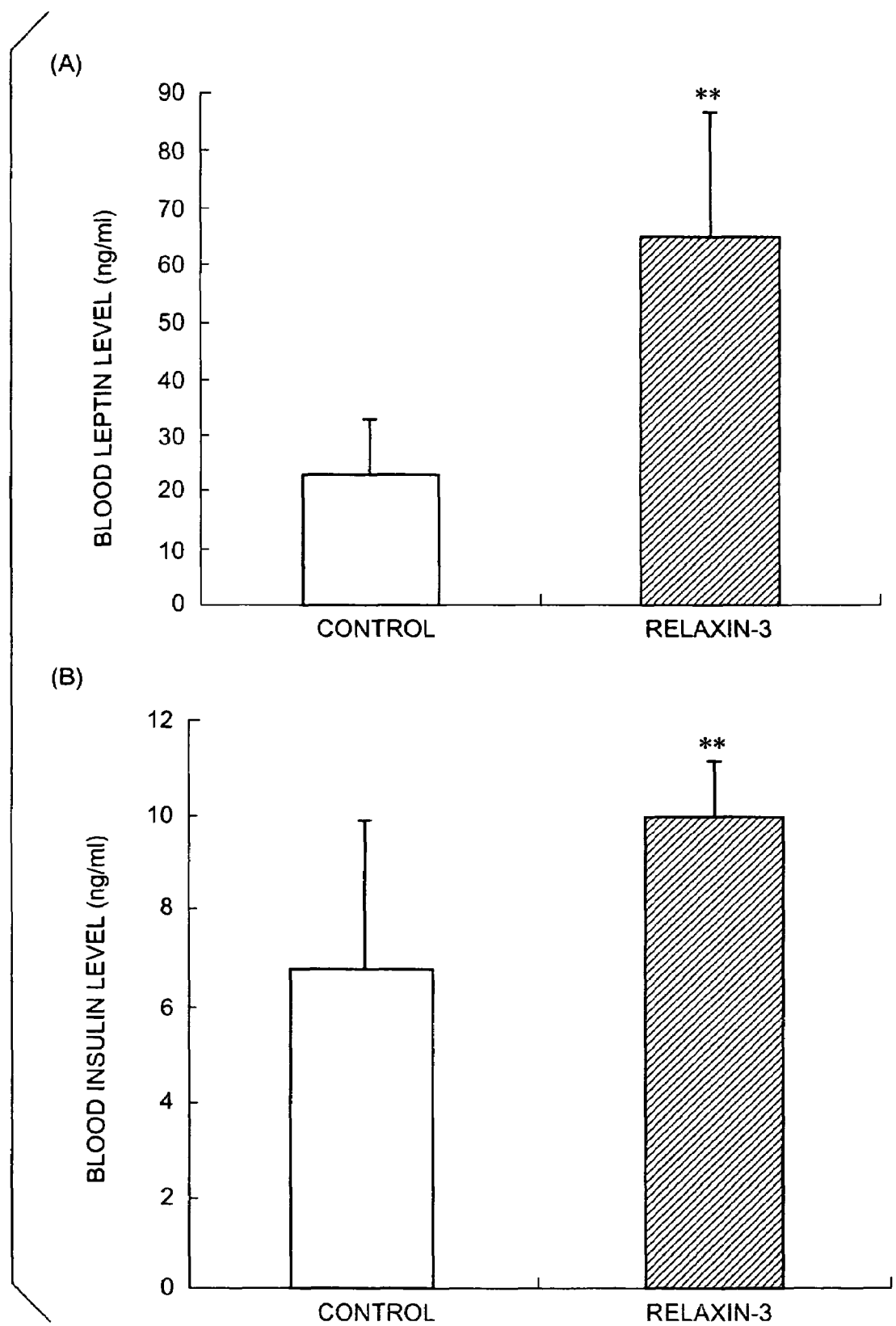

FIG. 10A-B shows the change in the blood hormone level by a chronic intracerebroventricular administration of relaxin-3 to normal rats. Panel A shows the effect on the blood leptin concentration. The white rectangular bar shows the vehicle administration group (control) and the black rectangular bar shows the relaxin-3 administration group. The vertical axis shows the mean and standard deviation of the blood leptin concentration (ng/ml) per animal in each group. Panel B shows the effect on the blood insulin concentration. The white rectangular bar shows the vehicle administration group (control) and the black rectangular bar shows the relaxin-3 administration group. The vertical axis shows the mean and standard deviation of the blood insulin concentration (ng/ml) per animal in each group.

Figure 11:
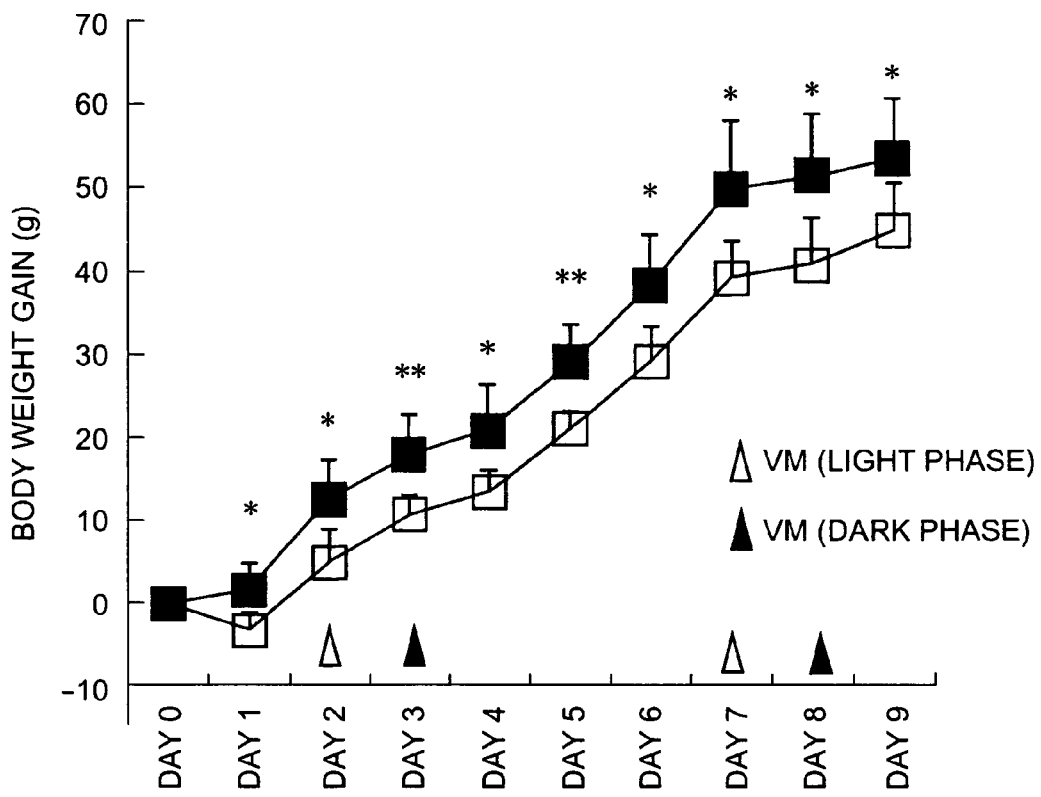

FIG. 11 shows the change in body weight gain in rats which were intracerebroventricularly administered with relaxin-3 continuously and reared while measuring their spontaneous locomotor activity. The white squares show the vehicle administration group (control) and the black squares show the relaxin-3 administration group. The vertical axis shows the mean and standard deviation of the body weight gain (g) per animal in each group. In the figure, the white triangles indicate days for measuring the locomotor activity in the light period and the black triangles indicate days for measuring the locomotor activity in the dark period.

Figure 12:
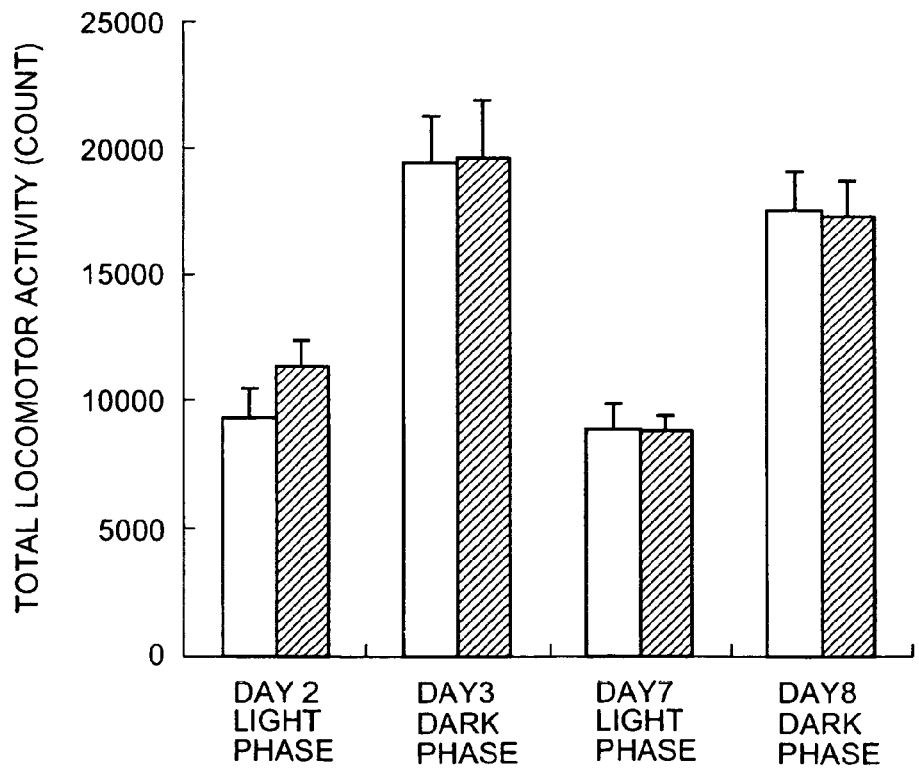

FIG. 12 shows the effect of a chronic intracerebroventricular administration of relaxin-3 to rats on spontaneous locomotor activity. The white bars show the vehicle administration group (control) and the black bars squares show the relaxin-3 administration group. The vertical axis shows the mean and standard deviation of the total locomotor activity (counts) per animal in each group.

BEST MODE FOR CARRYING OUT THE INVENTION

Relaxin-3

"Relaxin-3" used in the present invention is a polypeptide called relaxin-3 (also known as INSL7 (GenBank Accession No. NM_080864)) which is newly identified by a gene sequence database (J. Biol. Chem. 277, 1148-1157, 2002), and means (i) a polypeptide comprising the amino acid sequence represented by SEQ ID NO: 2. Further, relaxin-3 also intends to include (ii) a modified polypeptide which is functionally equivalent to a polypeptide comprising the amino acid sequence represented by SEQ ID NO: 2, and (iii) a homologous polypeptide comprising an amino acid sequence having 70% or more homology to the amino acid sequence of a polypeptide comprising the amino acid sequence represented by SEQ ID NO: 2. Relaxin-3 used in the present invention is preferably "a polypeptide comprising the amino acid sequence represented by SEQ ID NO: 2." Further, the above-mentioned polypeptide intends to include salts of the polypeptide, and those with and without sugar chains.

The term "functionally equivalent modified polypeptide (referred to as modified polypeptide hereinafter)" as used herein means a polypeptide that has a modified amino acid sequence of the amino acid sequence of SEQ ID NO: 2 having one or more (preferably one or several) deletions, substitutions, insertions and/or additions of amino acids and exhibits substantially the same activities as relaxin-3 [for example relaxin-3-receptor binding ability, various cell-stimulating activities associated with the binding (e.g., intracellular calcium release, adenylyl cyclase activation, intracellular cAMP production, intracellular cGMP production, inositol phospholipid production, electrical potential change in the cell membrane, pH change in the vicinity of the cell membrane, phosphorylation of intracellular proteins, c-fos and c-jun induction/activation, arachidonic acid release), feeding-stimulation, body weight gain, and fattening].

The term "substitution" in this specification means the replacement of one or more amino acid residues with other chemically homologous amino acid residues so as not to substantially change peptide activity. For example, a certain hydrophobic residue can be substituted with another hydrophobic residue and a certain polar residue can be substituted with another polar residue having the same charge. Functionally homologous amino acids capable of carrying out these substitutions for each amino acid are known to those skilled in the art. More specifically, examples of non-polar (hydrophobic) amino acids include alanine, valine, isoleucine, leucine, proline, tryptophan, phenylalanine, and methionine. Examples of polar (neutral) amino acids include glycine, serine, threonine, tyrosine, glutamine, asparagine, and cysteine. Examples of positively charged (basic) amino acids include arginine, histidine, and lysine. Examples of negatively charged (acidic) amino acids include aspartic acid and glutamic acid.

The number of amino acid residues to be deleted, substituted, inserted and/or added is, for example, 1 to 30, preferably 1 to 20, more preferably 1 to 10, further more preferably 1 to 5, and most preferably 1 to 2. Further, the above-mentioned modified polypeptide means to include salts of the modified polypeptide, including those with and without sugar chains. Accordingly, the origin of the above-mentioned polypeptide is not limited to humans as long as the conditions above are satisfied. For example, relaxin-3 and its variations derived from organisms other than humans [for example, non-human mammals (e.g., mice, rats, hamsters, pigs, canines), birds, reptiles, amphibians, fish, and insects] are included.

The above-mentioned homologous polypeptide is not particularly limited as long as it comprises an amino acid sequence having 70% or more homology to the amino acid sequence of relaxin-3; it means an amino acid sequence which comprises an amino acid sequence having preferably 80% or more, more preferably 85% or more, further preferably 90% or more, further more preferably 95% or more, and particularly preferably 98% or more, and most preferably 99% or more, homology to relaxin-3 and exhibits substantially the same activities as relaxin-3 (for example, relaxin-3-receptor binding ability, various cell-stimulating activities associated with the binding, feeding-stimulation, body weight gain, and fattening). The figures for the "homology" in this specification can be figures calculated using a homology search program known to those skilled in the art; for example, they can be calculated using default parameters in the homology algorithm BLAST (basic local alignment search tool) http://www.ncbi.nlm.nih.gov/BLAST/ by The National Center for Biotechnology Information (NCBI). Further, the above-mentioned homologous polypeptide includes salts of the homologous polypeptide, including those with and without sugar chains. Accordingly, the origin of the above-mentioned homologous polypeptide is not limited to humans as long as the conditions above are satisfied. For example, relaxin-3 and its variations derived from organisms other than humans [for example, non-human mammals (e.g., mice, rats, hamsters, pigs, canines), birds, reptiles, amphibians, fish, and insects] are included.

The term "variation" as used herein refers to the differences among the individuals within the same polypeptide in the same species or the variations among homologous polypeptides between different species.

Relaxin-3 (namely, relaxin-3, a modified polypeptide, or a homologous polypeptide) to be used in the present invention can be obtained by various known methods, such as a genetic engineering method and a synthesis method. More specifically, in a genetic engineering method, a polynucleotide encoding relaxin-3 is introduced into an appropriate host cell, the resulting transformant is cultured under the conditions for enabling the expression, and then the polypeptide of interest can be isolated and purified from the culture by a method generally used for isolation and purification of an expressed protein. In a synthesis method, synthesis can be possible using an ordinary method such as a liquid phase method and a solid phase method; generally an automatic synthesizer can be used. A chemically modified compound can be synthesized by an ordinary method. Further, a polypeptide to be used can be either the entire or a part of SEQ ID NO: 2 or a polypeptide that has undergone secretory protein processing, such as cross-linking between cystines, N-terminal cyclic glutamination, and C-terminal amidation.

Polynucleotide Encoding Relaxin-3

A polynucleotide encoding relaxin-3 to be used in the present invention is not particularly limited as long as it is a polynucleotide encoding a polypeptide to be used in the present invention.

The term "polynucleotide" as used herein includes both DNA and RNA. More specifically, the polynucleotide used in the present invention is selected from the group consisting of the following (a) to (e):

(a) a polynucleotide consisting of the base sequence represented by SEQ ID NO: 1;
(b) a polynucleotide encoding "polypeptide consisting of the amino acid sequence represented by SEQ ID NO: 2";
(c) a polynucleotide encoding "a polypeptide which comprises the amino acid sequence represented by SEQ ID NO: 2 and exhibits substantially the same activities as the above-mentioned relaxin-3";
(d) a polynucleotide encoding "a polypeptide which comprises a modified amino acid sequence of the amino acid sequence represented by SEQ ID NO: 2 having one or more (preferably one or several) deletions, substitutions, insertions and/or additions of amino acids and exhibits substantially the same activities as the above-mentioned relaxin-3"; and
(e) a polynucleotide which hybridizes with a polynucleotide consisting of the base sequence represented by SEQ ID NO: 1 under stringent conditions and encodes a polypeptide having substantially the same activities as the above-mentioned relaxin-3.

According to one embodiment of the present invention, the polynucleotide to be used in the present invention is a polynucleotide encoding "a polypeptide which comprises a modified amino acid sequence of the amino acid sequence represented by SEQ ID NO: 2 having one or more (preferably one or several) deletions, substitutions, insertions and/or additions of amino acids and exhibits substantially the same activities as the above-mentioned relaxin-3." Here, the number of amino acid residues which can be deleted, substituted, inserted and/or added is, for example, 1 to 30, preferably 1 to 20, more preferably 1 to 10, further more preferably 1 to 5, and most preferably 1 to 2.

According to another embodiment of the present invention, the polynucleotide to be used in the present invention is a polynucleotide which hybridizes with a polynucleotide consisting of the base sequence represented by SEQ ID NO: 1 under stringent conditions and encodes "a polypeptide having substantially the same activities as the above-mentioned relaxin-3."

In this specification, a specific example of the polynucleotide which hybridizes under stringent conditions is a polynucleotide having at least 70% or more, preferably 80% or more, more preferably 85% or more, further preferably 90% or more, further more preferably 95% or more, particularly preferably 98% or more, and most preferably 99% or more homology to the base sequence represented by SEQ ID NO: 1 when the homology is calculated by a homology search software, such as FASTA, BLAST, Smith-Waterman (Meth. Enzym., 164, 765, 1988), using default parameters. Further, hybridization "under stringent conditions" can be performed, for example, by a method in which the reaction is carried out at 40° to 70° C., preferably at 60° C. to 65° C., in a hybridization buffer solution generally used by those skilled in the art and washing is carried out in a washing solution at a salt concentration of 15 to 300 mmol/L, preferably at 15 to 60 mmol/L. The temperature and salt concentration can be appropriately adjusted depending on the length of the probe to be used.

A polynucleotide to be used in the present invention can be, for example, of natural origin or entirely synthesized. Further, it can be synthesized using a part of a natural product. Typically, a polynucleotide to be used in the present invention can be obtained, for example, from a commercial library or a cDNA library by a method customarily used in the field of genetic engineering, for example, by a screening method using an appropriate DNA probe constructed based on information of a partial amino acid sequence (for example the amino acid sequence represented by SEQ ID NO: 2).

As a polynucleotide to be used in the present invention, "a polynucleotide comprising the base sequence represented by SEQ ID NO: 1" is preferable. The base sequence represented by SEQ ID NO: 1 has an open reading frame starting with ATG at position 1-3 and ending with TAG at position 427-429.

Pharmaceutical Composition Containing Relaxin-3

Relaxin-3 used in the present invention can be used as a feeding-stimulating agent to treat dysorexia and nutritional disorders with decrease in feeding, as a body weight gaining agent and a fattening agent to treat diseases which requires body weight gain, as a medicine to treat diseases caused by some abnormality in controlling obesity, and as a medicine to treat diseases caused by abnormality in relaxin-3 or a polynucleotide encoding relaxin-3. Further, it can be used as a therapeutic medicine for the purpose of recovering feeding (or appetite) and/or body weight decreased due to onset of various diseases or treatment of various diseases (for example, during or after an operation). Examples of the above-mentioned various diseases include diseases involved in the movement or function of the alimentary tract (e.g., diarrhea, constipation, functional constipation, hypersensitive intestinal syndrome, and conditions which require defecation to remove intestinal contents upon alimentary canal examination or before or after an operation), diseases involved in control of the immune functions (for example, chronic rheumatoid arthritis, systemic erythematodes, kidney diseases, scleroderma, atopic dermatitis, bronchial asthma, multiple sclerosis, rheumatic interstitial pneumonia, sarcoidosis, Crohn's disease, inflammatory colitis, liver cirrhosis, chronic hepatitis, fulminant hepatitis, encephalomyelitis, and myasthenia gravis), feeding disorder, anorexia, AIDS, cancers, and cachexia. They are preferably anorexia and cachexia.

Said polypeptide or its salt can be used alone; however, it can also be used as a pharmaceutical composition by admixing with a pharmaceutically acceptable carrier.

The term "salt" as used herein is not particularly limited as long as it is a salt formed with a compound of the present invention and pharmaceutically acceptable. Preferred examples of such salt include halogenated hydroacid salts (e.g., hydrofluorides, hydrochlorides, hydrobromides, hydroiodides), inorganic acid salts (e.g., sulfates, nitrates, perchlorates, phosphates, carbonates, bicarbonates), organic carboxylates (e.g., acetates, trifluroacetates, oxalates, maleates, tartrates, fumarates, citrates), organic sulfonates (e.g., methanesulfonates, trifluoromethanesulfonates, ethanesulfonates, benzensulfonates, toluenesulfonates, camphorsulfonates), amino acid salts (e.g., aspartates, glutamates), quaternary amine salts, alkaline metal salts (e.g., sodium salts, potassium salts) and alkaline earth metal salts (e.g., magnesium salts, calcium salts). Hydrochlorides, oxalates and the like are preferred as said "pharmaceutically acceptable salt."

Here, the percentage of the active ingredient in the carrier can vary between 1 to 90% by weight. The above-mentioned medicine can be administered in various forms either orally or parenterally (for example, by intravenous, intramuscular, subcutaneous, rectal, or dermal administration) to humans or organisms other than humans [for example, non-human mammals (e.g., cattle, monkeys, poultry, cats, mice, rats, hamsters, pigs, canines), birds, reptiles, amphibians, fish, and insects]. Accordingly, the pharmaceutical composition containing relaxin-3 of the present invention is formulated into an appropriate dosage form depending on the administration route. More specifically, it can be formulated into oral formulations such as tablets, capsules, granules, dispersible powders and syrups or parenteral formulations such as injections, intravenous drips, liposome compositions, and suppositories. These pharmaceutical preparations can be manufactured by an ordinary method using commonly used excipients, fillers, binding agents, wetting agents, disintegrating agents, surfactants, lubricants, dispersing agents, buffering agents, preservatives, solubilizing agents, antiseptics, flavoring agents, analgesic agents, stabilizers, and the like. Examples of the above-mentioned non-toxic additives to be used include lactose, fructose, glucose, starch, gelatin, magnesium stearate, methylcellulose or its salts, ethanol, citric acid, sodium chloride, and sodium phosphate.

The dosage form and amount of the administration depend on the selection of polypeptide, the subject to be administered, the administration route, properties of the preparation, conditions of the patient, and physician's judgement. However, the appropriate dose per 1 kg of patient's body weight ranges, for example, from about 0.1 to 500 μg, preferably from about 0.1 to 100 μg, and more preferably from about 1 to 50 μg. The amount of necessary dosage is expected to vary widely considering that the efficiency is different depending on the route of administration. For example, the necessary dose for oral administration is expected to be higher than that for intravenous injection. Such variations in the dose level can be adjusted using a standard empirical optimizing procedure well understood in the field.

Method of Screening for Compounds Involved in Feeding-control Using Relaxin-3 Receptor As a relaxin-3 receptor used in the present invention, among various receptors, a receptor which has an ability to bind relaxin-3 and exhibits various cell-stimulating activities of the relaxin-3 receptor expressing cell (e.g., intracellular calcium release, adenylyl cyclase activation, intracellular cAMP production, intracellular cGMP production, inositol phospholipid production, electrical potential change in the cell membrane, pH change in the vicinity of the cell membrane, phosphorylation of intracellular proteins, c-fos and c-jun induction/activation, arachidonic acid release) can be used.

More specifically, as a relaxin-3 receptor, a reported known receptor, for example, LGR7 (GenBank Accession No. NM_021634), SALPR (GenBank Accession No. NM_016568, also called GPCR135), or GPR100 (GenBank Accession No. AB_083593, also called hGPCR11 or GPCR142) can be used. Further, a partial polypeptide of these receptors is not particularly limited as long as it is usable in the screening method described later and a partial polypeptide having a binding ability to relaxin-3, a partial polypeptide comprising an amino acid sequence corresponding to the outside region of the cell membrane or the like can also be used.

The content of the present invention will be explained in detail below in this specification, referring to a screening method using SALPR as a preferred example of the present invention. Namely, the present invention is to provide a method of screening for a compound which binds to SALPR or its partial polypeptide and is involved in the control of feeding (stimulation or suppression of feeding). Further, whether a substance has an activity to stimulate or suppress feeding can be determined by allowing the test substance to act on SALPR or its partial polypeptide and measuring cell-stimulating activities.

SALPR or its partial polypeptide can be obtained by various known methods; for example, it can be prepared by a known genetic engineering method using a polynucleotide encoding SALPR (GenBank Accession No. NM_016568). In another embodiment, it can be obtained by a known polypeptide synthesis method, such as an ordinary method, e.g., a liquid phase method or solid phase method; an auto-synthesizer can generally be used. Further, in another embodiment, a partial polypeptide of SALPR can be prepared by cleaving SALPR with an appropriate proteolytic enzyme.

The polypeptide encoding SALPR to be used in the present invention means a polypeptide comprising the amino acid sequence represented by SEQ ID NO: 4, a modified polypeptide functionally equivalent to a polypeptide comprising the amino acid sequence represented by SEQ ID NO: 4, or a polypeptide which comprises an amino acid sequence having 70% or more, preferably 80% or more, more preferably 85% or more, further preferably 90% or more, further more preferably 95% or more, particularly preferably 98% or more, and most preferably 99% or more, homology to the amino acid sequence represented by SEQ ID NO: 4 and exhibits substantially the same activities as relaxin-3 (for example, a binding ability to relaxin-3 and various cell-stimulating activities associated with the binding, or a feeding-controlling activity).

Here, the modified polypeptide functionally equivalent to a polypeptide comprising the amino acid sequence represented by SEQ ID NO: 4 means a polypeptide which comprises an amino acid sequence having one or more deletions, substitutions, insertions and/or additions of one or more (preferably one or several) amino acids in the polypeptide comprising the amino acid sequence represented by SEQ ID NO: 4 and exhibits substantially the same activities as SALPR (for example, a binding ability to relaxin-3 and various cell-stimulating activities associated with the binding, or a feeding-controlling activity).

Further, a partial polypeptide of SALPR can also be used as long as it has substantially the same activities as SALPR (for example, a binding ability to relaxin-3 and various cell-stimulating activities associated with the binding, or a feeding-controlling activity).

The genetic engineering method will be explained in detail more specifically using SALPR below; however, its partial peptide can also be used as long as it is usable in the screening method described later.

A polynucleotide encoding SALPR is introduced into an appropriate host cell, the resulting transformant is cultured under the conditions for enabling the expression, and thus a polypeptide of interest can be isolated and purified from the culture by a method generally used for isolation and purification of an expressed protein. Examples of the method for the above-mentioned isolation and purification include ammonium sulphate salting-out, ion-exchange column chromatography using ion-exchange cellulose, molecular sieving column chromatography using a molecular sieving gel, affinity column chromatography using a protein-A binding polysaccharide, dialysis and lyophilization.

A polynucleotide encoding SALPR to be used in the present invention is not particularly limited as long as it is a polynucleotide encoding a polypeptide to be used in the present invention.

The term "polynucleotide" as used herein includes both DNA and RNA. More specifically, the polynucleotide used in the present invention is selected from the group consisting of the following (a) to (e):

(a) a polynucleotide comprising the base sequence represented by SEQ ID NO: 3;
(b) a polynucleotide encoding "a polypeptide comprising the amino acid sequence represented by SEQ ID NO: 4";
(c) a polynucleotide encoding "a polypeptide which comprises the amino acid sequence represented by SEQ ID NO: 4 and exhibits substantially the same activities as the above-mentioned SALPR";
(d) a polynucleotide encoding "a polypeptide which comprises an amino acid sequence having deletions, substitutions, insertions and/or additions of one or more (preferably one or several) amino acids at one or more (preferably one or several) sites of the amino acid sequence represented by SEQ ID NO: 4 and exhibits substantially the same activities as the above-mentioned SALPR"; and
(e) a polynucleotide which hybridizes with a polynucleotide comprising the base sequence represented by SEQ ID NO: 3 under stringent conditions and encodes a polypeptide which exhibits substantially the same activities as the above-mentioned SALPR.

According to one embodiment of the present invention, the polynucleotide to be used in the present invention is a polynucleotide comprising the base sequence represented by SEQ ID NO: 3. The above-mentioned polynucleotide represented by SEQ ID NO: 3 encodes SALPR comprising the amino acid sequence represented by SEQ ID NO: 4.

According to another embodiment of the present invention, the polynucleotide to be used in the present invention is a polynucleotide encoding "a polypeptide which comprises an amino acid sequence having deletions, substitutions, insertion and/or additions of one or more (preferably one or several) amino acids at one or more (preferably one or several) sites of the amino acid sequence represented by SEQ ID NO: 4 and exhibits substantially the same activities as the above-mentioned SALPR." Here the number of amino acid residues which can be deleted, substituted, inserted and/or added is, for example, 1 to 30, preferably 1 to 20, more preferably 1 to 10, further more preferably 1 to 5, and most preferably 1 to 2.

According to still another embodiment of the present invention, the polynucleotide to be used in the present invention is a polynucleotide which hybridizes with a polynucleotide comprising the base sequence represented by SEQ ID NO: 3 under stringent conditions and encodes a polypeptide which exhibits substantially the same activities as the above-mentioned SALPR. Further, according to still another embodiment of the present invention, the polynucleotide to be used in the present invention is a polynucleotide which hybridizes with a polynucleotide consisting of the base sequence represented by SEQ ID NO: 3 under stringent conditions and encodes a polypeptide which exhibits substantially the same activities as the above-mentioned SALPR.

A plasmid to be used in the above-mentioned transformation is not particularly limited as long as it contains a polynucleotide encoding the above-mentioned SALPR; for example, it can be obtained by inserting said polynucleotide into a known expression vector appropriately selected depending on a host cell used.

The above-mentioned transformant is also not particularly limited as long as it contains a polynucleotide encoding the above-mentioned SALPR; for example, it can be a transformant in which said polynucleotide is incorporated into a chromosome of the host cell, a transformant which contains said polynucleotide in the form of a plasmid, or a transformant which does not express SALPR. Said transformant can be obtained, for example, by transforming a desired host cell with the above-mentioned plasmid or the above-mentioned polynucleotide itself.

Examples of the above-mentioned host cell include generally used known microorganisms such as *Escherichia coli* (e.g., *E. coli* JM109) and yeasts (e.g., *Saccharomyces cerevisiae* W303) and known culture cells such as animal cells (e.g., CHO cells, HEK-293 cells, COS cells) and insect cells (e.g., EmN4 cells).

Examples of the above-mentioned expression vector include pUC, pTV, pGEX, pKK, and pTrcHis for *E. coli*; pEMBLY and pYES2 for yeasts; pcDNA3, pMAMneo and pBabe Puro for CHO cells, HEK-293 cells and COS cells; and a vector having the polyhedrin promoter of Bombyx mori nuclear polyhedrosis virus (BmNPV) (e.g., pBK283) for BmN4 cells.

A cell containing SALPR is not particularly limited as long as it expresses SALPR on the surface of the cell membrane and can be obtained, for example, by culturing the above-mentioned transformant (namely, the cell transformed with a plasmid containing a polynucleotide encoding SALPR) under the conditions enabling the expression of SALPR, or by injecting RNA encoding SALPR into an appropriate cell and culturing it under the conditions enabling the expression of SALPR.

A cell membrane fraction containing SALPR to be used in the present invention can be obtained, for example, by disrupting the cells expressing SALPR according to the present invention and then isolating a fraction rich in the cell membrane. Examples of the method of disrupting the cells include a method of disrupting the cells using a homogenizer (e.g., a Potter-Elvehiem-type homogenizer), disruption by a Waring blender or Polytron (Kinematica), ultrasonic disruption, and disruption by ejecting the cells from a fine nozzle under pressure using a French press or the like. Further, examples of the method for fractionating the cell membrane include a fractionation method by centrifugation, such as differential centrifugation and density gradient centrifugation.

In a method of screening for a compound which stimulates or suppresses feeding via SALPR according to the present invention, SALPR, the above-mentioned cell membrane fraction (namely, a cell membrane fraction containing SALPR) or the above-mentioned cell (namely, the cell containing SALPR) can be used.

Further, a screening method according to the present invention includes and utilizes a method of examining whether a test substance binds specifically to SALPR and a method of examining cell-stimulating activities generated by the binding of the test substance to SALPR (for example, intracellular calcium release, adenylyl cyclase activation, intracellular cAMP production, intracellular cGMP production, inositol phospholipid production, electrical potential change in the cell membrane, pH change in the vicinity of the cell membrane, phosphorylation of intracellular proteins, c-fos and c-jun induction/activation, and arachidonic acid release).

In the screening method according to the present invention, for example, SALPR, the above-mentioned cell membrane fraction or the above-mentioned cell is contacted with a test substance to analyze whether SALPR, the above-mentioned cell membrane fraction, or the above-mentioned cell binds to the test substance, and thus the screening for the compound can be achieved without distinction between stimulating and suppressing abilities in feeding via SALPR.

Specifically, in the presence or absence of the test substance, SALPR, the above-mentioned cell membrane fraction or the above-mentioned cell is contacted with a labeled natural ligand (namely relaxin-3) to compare the amount of specific binding of the above-mentioned natural ligand via SALPR, the above-mentioned cell membrane fraction or the above-mentioned cell, and thus the screening for the compound can be achieved without distinction between stimulating and suppressing abilities in feeding via SALPR. Namely, when the above-mentioned test substance has feeding-stimulating or -suppressing ability via SALPR, the amount of specific binding of the natural ligand via SALPR, the above-mentioned cell membrane fraction or the above-mentioned cell in the presence of the test substance decreases as compared to the corresponding amount of the specific binding in the absence of the test substance.

In the screening method according to the present invention, when the amount of specific binding of the natural ligand via SALPR, the above-mentioned cell membrane fraction or the above-mentioned cell is compared, a labeled natural ligand can be used as the above-mentioned natural ligand. For the above-mentioned labeling, a radioactive isotope, an enzyme, a fluorescent substance, a luminescent substance and the like can be used. Examples of the radioactive isotope include [$^3$H], [$^{14}$C], [$^{125}$I], and [$^{35}$S]. Examples of the enzyme include β-galactosidase, alkaline phosphatase, and peroxidase. Examples of the fluorescent substance include fluorescein isothiocyanate and BODIPY. Examples of the luminescent substance include luciferin and lucigenin. Occasionally, the biotin-avidin system can be used for binding of the natural ligand and the labeling substance.

Thus, the screening method according to the present invention can screen for a compound which binds to SALPR, the above-mentioned cell membrane fraction or the above-mentioned cell to inhibit their binding to the natural ligand, without distinction between stimulating and suppressing abilities in feeding via SALPR.

In another embodiment of the screening method according to the present invention, the above-mentioned cell is contacted with a labeled natural ligand (namely relaxin-3) under conditions in the presence or absence of a test substance to compare the amount of specific binding of the above-mentioned natural ligand via the above-mentioned cell under these conditions and then further compare a specific cell-stimulating activity of the above-mentioned natural ligand under these conditions, thereby enabling the screening for a compound with distinction between stimulating and suppressing abilities in feeding via SALPR.

In the above-mentioned embodiment, a substance which binds to the above-mentioned cell and exhibits the cell-stimulating activity via a receptor contained in the above-mentioned cell can be selected as a compound which stimulates feeding via SALPR.

On the other hand, in the above-mentioned embodiment, a test substance which inhibits binding of the above-mentioned cell and the natural ligand but does not exhibit the cell-stimulating activity can be selected as a compound which suppresses feeding via SALPR.

The screening method according to the present invention can be carried out using, for example, suppression of adenylyl cyclase activity as a cell-stimulating activity.

In the screening method of this embodiment, for example, cAMP produced in a cell by the activation of adenylyl cyclase can be measured using a known method, thereby enabling the screening for a compound with distinction between stimulating and suppressing abilities in feeding via SALPR. This embodiment utilizes intracellular signal transmission generated by the binding of the natural ligand to SALPR, namely, the suppression of adenylyl cyclase activity which is one of cell-stimulating activities of SALPR. Specifically, when the natural ligand binds to SALPR, a Gi family that is a member of G protein family coupled with SALPR suppresses adenylyl cyclase to decrease the amount of cyclic AMP (cAMP, produced from ATP by adenylyl cyclase) produced in the cell.

For example, the intracellular cAMP concentration increases when an adenylyl cyclase-activating agent [such as forskolin (FSK)] is added to mammal-derived cells (for example, HEK-293 cells or CHO cells) in which SALPR is expressed on the cell membrane (preferably, excessively expressed by introducing an expression vector containing SALPR).

Further, when a natural ligand of SALPR is added upon adding an adenylyl cyclase-activating agent, adenylyl cyclase activity suppression also occurs due to the action of the above-mentioned natural ligand on SALPR according to the present invention, in addition to the above-mentioned adenylyl cyclase activity stimulation due to the adenylyl cyclase-activating agent, which results in a decrease in the cAMP production as compared to the case where the adenylyl cyclase activating agent alone is added. Therefore, when the screening is carried out for a compound having a feeding-stimulating activity, a compound which decreases the cAMP production (namely having the same activity as the natural ligand) can be selected by contacting the test substance alone, in place of the natural ligand which acts via SALPR in this screening system.

When the screening is carried out for a compound having a feeding-suppressing activity, an adenylyl cyclase activating agent, a natural ligand of SALPR, and a test substance can be added to cells for screening. The cAMP production decreases due to the action of the natural ligand as compared to the case where the adenylyl cyclase activating agent alone is added; however, the decrease in the cAMP production is suppressed when the test substance antagonizes the action of the natural ligand. In this case, this test substance can be selected as a compound having a feeding-suppressing activity.

As a method for measuring the amount of intracellular cAMP, an immunoassay or the like can be used; for example, a commercial kit for cAMP quantification can also be used.

In another embodiment of the screening method, for example, screening for a compound can be achieved with distinction between stimulating and suppressing abilities in feeding via SALPR, by using a cell (occasionally referred to as "screening cell" hereinafter) in which SALPR is expressed on the cell membrane (preferably excessively expressed by introducing an expression vector containing SALPR) and a reporter gene [for example, the alkaline phosphatase gene, the luciferase gene, the β-lactamase gene, the nitroreductase gene, the chloramphenicol acetyl transferase gene, the β-galactosidase gene, or a fluorescent protein gene such as GFP (green fluorescent protein) gene] having a cAMP-responding element (CRE) located upstream of the 5' end is contained. This embodiment utilizes the fact that the transcription of the reporter gene, which has the CRE introduced into the above-mentioned screening cell in the promoter region, is suppressed as a result of the decrease in the above-mentioned cAMP production.

A process of screening for a compound with distinction between stimulating and suppressing abilities in feeding via SALPR by the above-mentioned embodiment will be explained in more detail as follows.

Namely, the CRE introduced into the above-mentioned screening cell is a base sequence commonly present in a transcription regulatory region of a group of genes (cAMP inducing genes) whose expression is accelerated when the intracellular cAMP concentration increases. Therefore, when an adenylyl cyclase activating agent (e.g., FSK) is added to a screening cell, the intracellular cAMP concentration increases, which results in an increase in the amount of expression of the reporter gene located in the downstream of the CRE. The amount of expression of a reporter gene product can be easily measured by measuring luminescence derived from a luminescent substance generated from a substrate reacted with the reporter gene product or fluorescence derived from a fluorescent protein produced as the reporter gene product.

Further, when a natural ligand of SALPR is added upon adding an adenylyl cyclase-activating agent, adenylyl cyclase activity suppression also occurs due to the action of the above-mentioned natural ligand on SALPR according to the present invention, in addition to the above-mentioned adenylyl cyclase activity stimulation due to the adenylyl cyclase-activating agent, which results in a decrease in the amount of the expression of the reporter gene product as compared to the case where the adenylyl cyclase activating agent alone is added. Therefore, when the screening is carried out for a compound having feeding-stimulating activity, a compound which decreases the amount of expression of the reporter gene product (namely having the same activity as the natural ligand) can be selected by contacting the test substance alone, in place of the natural ligand which acts via SALPR in this screening system.

When the screening is carried out for a compound having a feeding-suppressing activity, an adenylyl cyclase activating agent, a natural ligand of SALPR, and a test substance can be added to a screening cell. The amount of expression of the reporter gene product decreases due to the action of the natural ligand as compared to the case where the adenylyl cyclase activating agent alone is added; however, the decrease in the amount of expression of the reporter gene product is suppressed when the test substance antagonizes the action of the natural ligand. In this case, the test substance can be selected as a compound having a feeding-suppressing activity.

Whether the action by a test substance is due to the action through the binding to SALPR can be easily confirmed. For example, in parallel with the above-mentioned test using a screening cell (namely, a cell which expresses SALPR on the cell membrane and contains a reporter gene with CRE located upstream of the 5' end), a similar test is carried out using a cell for control (for example, a cell which contains a reporter gene with CRE located upstream of the 5' end but does not express SALPR on the cell membrane). As a result, the cell for screening and the cell for control show the same phenomenon regarding the amount of expression of the reporter gene product when the action by the above-mentioned test substance is not due to the binding to SALPR, while the cell for screening and the cell for control show different phenomena regarding the amount of expression of the reporter gene product when the action by the above-mentioned test substance is due to the binding to SALPR.

Further, in another embodiment, a test substance influencing feeding-control can be confirmed and determined by administering the test substance selected by the above-mentioned screening method to humans or organisms other than humans [for example, non-human mammals (e.g., cattle, monkeys, poultry, cats, mice rats, hamsters, pigs, canines), birds, reptiles, amphibians, fish, and insects] and analyzing indices such as the amount of feeding and changes in blood parameters after administration. The above-mentioned mammals are not limited to normal animals, but can also be genetic mutant animal models for disease (for example, morbid obesity models such as ob/ob mice, db/db mice, and Zucker fatty rats) and genetically modified animals. The test substance can be administered either orally or parenterally. Examples of the parenteral route include intravenous, intraarterial, subcutaneous, intraperitoneal, intratracheal, intrarectal, and intracerebral administration, preferably administration into the cerebroventricle near the hypothalamus. As the indices for the screening, body weight, the amount of motor activity, the amount of energy metabolism, the amount of blood sugar and fat, the amount of hormones, the amount of secretory peptides and the like can be effectively measured other than the amount of feeding. Further, upon administration, conditions such as fasting, satiation, and excessive fat diet can be added.

The test substance can be administered in a single or divided dose per day and the administration or observation period can be from one day to several weeks.

Method of Screening for Compounds Involved in Body Weight Control using Relaxin-3 Receptor As a relaxin-3 receptor to be used in the present invention, among various receptors, a receptor which has an ability to bind relaxin-3 and exhibits various cell-stimulating activities of the relaxin-3 receptor expressing cell (e.g., intracellular calcium release, adenylyl cyclase activation, intracellular cAMP production, intracellular cGMP production, inositol phospholipid production, electrical potential change in the cell membrane, pH change in the vicinity of the cell membrane, phosphorylation of intracellular proteins, c-fos and c-jun induction/activation, arachidonic acid release) can be used.

More specifically, as a relaxin-3 receptor, a reported known receptor, for example, LR7 (GenBank Accession No. NM_021634), SALPR (GenBank Accession No. NM_016568, also called GPCR135), or GPR100 (GenBank Accession No. AB_083593, also called hGPCR11 or GPCR142) can be used. Further, a partial polypeptide of these receptors is not particularly limited as long as it is usable in the screening method described later and a partial polypeptide having a binding ability to relaxin-3, a partial polypeptide comprising an amino acid sequence corresponding to the outside region of the cell membrane or the like can also be used.

The content of the present invention will be explained in detail below in this specification, referring to a screening method using SALPR as a preferred example of the present invention. Namely, the present invention is to provide a method of screening for a compound which binds to SALPR or its partial polypeptide and is involved in the control of body weight (increase or decrease in body weight). Further, whether a substance has an activity to increase or decrease body weight can be determined by allowing the test substance to act on SALPR or its partial polypeptide and measuring cell-stimulating activities.

SALPR or its partial polypeptide can be obtained by various known methods; for example, it can be prepared by a known genetic engineering method using a polynucleotide encoding SALPR (GenBank Accession No. NM_016568). In another embodiment, it can be obtained by a known polypeptide synthesis method, such as an ordinary method, e.g., a liquid phase method or solid phase method; an autosynthesizer can generally be used. Further, in another embodiment, a partial polypeptide of SALPR can be prepared by cleaving SALPR with an appropriate proteolytic enzyme.

The polypeptide encoding SALPR to be used in the present invention means a polypeptide comprising the amino acid sequence represented by SEQ ID NO: 4, a modified polypeptide functionally equivalent to a polypeptide comprising the amino acid sequence represented by SEQ ID NO: 4, or a polypeptide which comprises an amino acid sequence having 70% or more, preferably 80% or more, more preferably 85% or more, further preferably 90% or more, further more preferably 95% or more, particularly preferably 98% or more, and most preferably 99% or more, homology to the amino acid sequence represented by SEQ ID NO: 4 and exhibits substantially the same activities as relaxin-3 (for example, a binding ability to relaxin-3 and various cell-stimulating activities associated with the binding, or a body weight controlling activity).

Here, the modified polypeptide functionally equivalent to a polypeptide comprising the amino acid sequence represented by SEQ ID NO: 4 means a polypeptide which comprises an amino acid sequence having one or more deletions, substitutions, insertions and/or additions of one or more (preferably one or several) amino acids in the polypeptide comprising the amino acid sequence represented by SEQ ID NO: 4 and exhibits substantially the same activities as SALPR (for example, a binding ability to relaxin-3 and various cell-stimulating activities associated with the binding, or a body weight controlling activity).

Further, a partial polypeptide of SALPR can also be used as long as it has substantially the same activities as SALPR (for example, a binding ability to relaxin-3 and various cell-stimulating activities associated with the binding, or a body weight controlling activity).

The genetic engineering method will be explained in detail more specifically using SALPR below; however, its partial peptide can also be used as long as it is usable in the screening method described later.

A polynucleotide encoding SALPR is introduced into an appropriate host cell, the resulting transformant is cultured under the conditions for enabling the expression, then a polypeptide of interest can be isolated and purified from the culture by a method generally used for isolation and purification of an expressed protein, and thus SALPR is prepared. Examples of the method for the above-mentioned isolation and purification include ammonium sulphate salting-out, ion-exchange column chromatography using an ion-exchange cellulose, molecular sieving column chromatography using a molecular sieving gel, affinity column chromatography using a protein-A binding polysaccharide, dialysis and lyophilization.

A polynucleotide encoding SALPR to be used in the present invention is not particularly limited as long as it is a polynucleotide encoding a polypeptide to be used in the present invention.

The term "polynucleotide" as used herein includes both DNA and RNA. More specifically, the polynucleotide used in the present invention is selected from the group consisting of the following (a) to (e):

(a) a polynucleotide comprising the base sequence represented by SEQ ID NO: 3;
(b) a polynucleotide encoding "a polypeptide comprising the amino acid sequence represented by SEQ ID NO: 4";
(c) a polynucleotide encoding "a polypeptide which comprises the amino acid sequence represented by SEQ ID NO: 4 and exhibits substantially the same activities as the above-mentioned SALPR";
(d) a polynucleotide encoding "a polypeptide which comprises an amino acid sequence having deletions, substitutions, insertions and/or additions of one or more (preferably one or several) amino acids at one or more (preferably one or several) sites of the amino acid sequence represented by SEQ ID NO: 4 and exhibits substantially the same activities as the above-mentioned SALPR"; and
(e) a polynucleotide which hybridizes with a polynucleotide comprising the base sequence represented by SEQ ID NO: 3 under stringent conditions and encodes a polypeptide which exhibits substantially the same activities as the above-mentioned SALPR.

According to one embodiment of the present invention, the polynucleotide to be used in the present invention is a polynucleotide comprising the base sequence represented by SEQ ID NO: 3. The above-mentioned polynucleotide represented by SEQ ID NO: 3 encodes SALPR comprising the amino acid sequence represented by SEQ ID NO: 4.

According to another embodiment of the present invention, the polynucleotide to be used in the present invention is a polynucleotide encoding "a polypeptide which comprises an amino acid sequence having deletions, substitutions, insertion and/or additions of one or more (preferably one or several) amino acids at one or more (preferably one or several) sites of the amino acid sequence represented by SEQ ID NO: 4 and exhibits substantially the same activities as the above-mentioned SALPR." Here the number of amino acid residues which can be deleted, substituted, inserted and/or added is, for example, 1 to 30, preferably 1 to 20, more preferably 1 to 10, further more preferably 1 to 5, and most preferably 1 to 2.

According to still another embodiment of the present invention, the polynucleotide to be used in the present invention is a polynucleotide which hybridizes with a polynucleotide comprising the base sequence represented by SEQ ID NO: 3 under stringent conditions and encodes a polypeptide which exhibits substantially the same activities as the above-mentioned SALPR. Further, according to still another embodiment of the present invention, the polynucleotide to be used in the present invention is a polynucleotide which hybridizes with a polynucleotide comprising the base sequence represented by SEQ ID NO: 3 under stringent conditions and encodes a polypeptide which exhibits substantially the same activities as the above-mentioned SALPR.

A plasmid to be used in the above-mentioned transformation is not particularly limited as long as it contains a polynucleotide encoding the above-mentioned SALPR; for example, it can be obtained by inserting said polynucleotide into a known expression vector appropriately selected depending on a host cell used.

The above-mentioned transformant is also not particularly limited as long as it contains a polynucleotide encoding the above-mentioned SALPR; for example, it can be a transformant in which said polynucleotide is incorporated into a chromosome of the host cell, a transformant which contains said polynucleotide in the form of a plasmid, or a transformant which does not express SALPR. Said transformant can be obtained, for example, by transforming a desired host cell with the above-mentioned plasmid or the above-mentioned polynucleotide itself.

Examples of the above-mentioned host cell include generally used known microorganisms such as *Escherichia coli* (e.g., *E. coli* JM109) and yeasts (e.g., *Saccharomyces cerevisiae* W303) and known culture cells such as animal cells (e.g., CHO cells, HEK-293 cells, COS cells) and insect cells (e.g., BmN4 cells).

Examples of the above-mentioned expression vector include pUC, pTV, pGEX, pKK, and pTrcHis for *E. coli*; pEMBLY and pYES2 for yeasts; pcDNA3, pMAMneo and pBabe Puro for CHO cells, HEK-293 cells and COS cells; and a vector having the polyhedrin promoter of Bombyx mori nuclear polyhedrosis virus (BmNPV) (e.g., pBK283) for BmN4 cells.

A cell containing SALPR is not particularly limited as long as it expresses SALPR on the surface of the cell membrane and can be obtained, for example, by culturing the above-mentioned transformant (namely, the cell transformed with a plasmid containing a polynucleotide encoding SALPR) under the conditions enabling the expression of SALPR, or by injecting RNA encoding SALPR into an appropriate cell and culturing it under the conditions enabling the expression of SALPR.

A cell membrane fraction containing SALPR to be used in the present invention can be obtained, for example, by disrupting the cells expressing SALPR according to the present invention and then isolating a fraction rich in the cell membrane. Examples of the method of disrupting the cells include a method of crushing the cells using a homogenizer (e.g., a Potter-Elvehiem-type homogenizer), disruption by a Waring blender or Polytron (Kinematica), ultrasonic disruption, and disruption by ejecting the cells from a fine nozzle under pressure using a French press or the like. Further, examples of the method for fractionating the cell membrane include a fractionation method by centrifugation, such as differential centrifugation and density gradient centrifugation.

In a method of screening for a compound which increases or decreases body weight via SALPR according to the present invention, SALPR, the above-mentioned cell membrane fraction (namely, a cell membrane fraction containing SALPR) or the above-mentioned cell (or the cell containing SALPR) can be used.

Further, a screening method according to the present invention includes and utilizes a method of examining whether a test substance binds specifically to SALPR and a method of examining cell-stimulating activities generated by the binding of the test substance to SALPR (for example, intracellular calcium release, adenylyl cyclase activation, intracellular cAMP production, intracellular cGMP production, inositol phospholipid production, electrical potential change in the cell membrane, pH change in the vicinity of the cell membrane, phosphorylation of intracellular proteins, c-fos and c-jun induction/activation, and arachidonic acid release).

In the screening method according to the present invention, for example, SALPR, the above-mentioned cell membrane fraction or the above-mentioned cell is contacted with a test substance to analyze whether SALPR, the above-mentioned cell membrane fraction, or the above-mentioned cell binds to the test substance, and thus the screening for the compound can be achieved without distinction between body weight increasing and decreasing abilities via SALPR.

Specifically, in the presence or absence of the test substance, SALPR, the above-mentioned cell membrane fraction or the above-mentioned cell is contacted with a labeled natural ligand (namely relaxin-3) to compare the amount of specific binding of the above-mentioned natural ligand via SALPR, the above-mentioned cell membrane fraction or the above-mentioned cell, and thus the screening for the compound can be achieved without distinction between body weight increasing and decreasing abilities via SALPR. Namely, when the above-mentioned test substance has body weight increasing or decreasing ability via SALPR, the amount of specific binding of the natural ligand via SALPR, the above-mentioned cell membrane fraction or the above-mentioned cell in the presence of the test substance decreases as compared to the corresponding amount of the specific binding in the absence of the test substance.

In the screening method according to the present invention, when the amount of specific binding of the natural ligand via SALPR, the above-mentioned cell membrane fraction or the above-mentioned cell is compared, a labeled natural ligand can be used as the above-mentioned natural ligand. For the above-mentioned labeling, a radioactive isotope, an enzyme, a fluorescent substance, a luminescent substance and the like can be used. Examples of the radioactive isotope include $[^3H]$, $[^{14}C]$, $[^{125}I]$, and $[^{35}S]$. Examples of the enzyme include β-galactosidase, alkaline phosphatase, and peroxidase. Examples of the fluorescent substance include fluorescein isothiocyanate and BODIPY. Examples of the luminescent substance include luciferin and lucigenin. Occasionally, the biotin-avidin system can be used for binding of the natural ligand and the labeling substance.

Thus, the screening method according to the present invention can screen for a compound which binds to SALPR, the above-mentioned cell membrane fraction or the above-mentioned cell to inhibit their binding to the natural ligand, without distinction between body weight increasing and decreasing abilities via SALPR.

In another embodiment of the screening method according to the present invention, the above-mentioned cell is contacted with a labeled natural ligand (namely relaxin-3) under conditions in the presence or absence of a test substance to compare the amount of specific binding of the above-mentioned natural ligand via the above-mentioned cell under the above-mentioned conditions and then further compare a specific cell-stimulating activity of the above-mentioned natural ligand under these conditions, thereby enabling the screening for a compound with distinction between body weight increasing and decreasing abilities via SALPR.

In the above-mentioned embodiment, a substance which binds to the above-mentioned cell and exhibits the cell-stimulating activity via a receptor contained in the above-mentioned cell can be selected as a compound which increases body weight via SALPR.

On the other hand, in the above-mentioned embodiment, a test substance which inhibits binding of the above-mentioned cell and the natural ligand but does not exhibit the cell-stimulating activity can be selected as a compound which decreases body weight via SALPR.

The screening method according to the present invention can be carried out using, for example, suppression of adenylyl cyclase activity as a cell-stimulating activity.

In the screening method of this embodiment, for example, cAMP produced in a cell by the activation of adenylyl cyclase can be measured using a known method, there by enabling the screening for a compound with distinction between body weight increasing and decreasing abilities via SALPR. This embodiment utilizes intracellular signal transmission generated by the binding of the natural ligand to SALPR, namely, the suppression of adenylyl cyclase activity which is one of cell-stimulating activities of SALPR. Specifically, when the natural ligand binds to SALPR, a Gi family that is a member of G protein family coupled with SALPR suppresses adenylyl cyclase to decrease the amount of cyclic AMP (cAMP, produced from ATP by adenylyl cyclase) produced in the cell.

For example, the intracellular cAMP concentration increases when an adenylyl cyclase-activating agent [such as forskolin (FSK)] is added to mammal-derived cells (for example, HEK-293 cells or CHO cells) in which SALPR is expressed on the cell membrane (preferably, excessively expressed by introducing an expression vector containing SALPR).

Further, when a natural ligand of SALPR is added upon adding an adenylyl cyclase-activating agent, adenylyl cyclase activity suppression also occurs due to the action of the above-mentioned natural ligand on SALPR according to the present invention, in addition to the above-mentioned adenylyl cyclase activity stimulation due to the adenylyl cyclase-activating agent, which results in a decrease in the cAMP production as compared to the case where the adenylyl cyclase activating agent alone is added. Therefore, when the screening is carried out for a compound having a body weight increasing activity, a compound which decreases the cAMP production (namely having the same activity as the natural ligand) can be selected by contacting the test substance alone, in place of the natural ligand which acts via SALPR in this screening system.

When the screening is carried out for a compound having a body weight decreasing activity, an adenylyl cyclase activating agent, a natural ligand of SALPR, and a test substance can be added to cells for screening. The cAMP production decreases due to the action of the natural ligand as compared to the case where the adenylyl cyclase activating agent alone is added; however, the decrease in the cAMP production is suppressed when the test substance antagonizes the action of the natural ligand. In this case, this test substance can be selected as a compound having a body weight decreasing activity.

As a method for measuring the amount of intracellular cAMP, an immunoassay or the like can be used; for example, a commercial kit for cAMP quantification can also be used.

In another embodiment of the screening method, for example, screening for a compound can be achieved with distinction between body weight increasing and decreasing abilities via SALPR, by using a cell (occasionally referred to as "screening cell" hereinafter) in which SALPR is expressed on the cell membrane (preferably excessively expressed by introducing an expression vector containing SALPR) and a reporter gene [for example, the alkaline phosphatase gene, the luciferase gene, the β-lactamase gene, the nitroreductase gene, the chloramphenicol acetyl transferase gene, the β-galactosidase gene, or a fluorescent protein gene such as GFP (green fluorescent protein) gene] having a cAMP responding element (CRE) located upstream of the 5' end is contained. This embodiment utilizes the fact that the transcription of the reporter gene which has the CRE introduced into the above-mentioned screening cell, in the promoter region is suppressed as a result of the decrease in the above-mentioned cAMP production.

A process of screening for a compound with distinction between body weight increasing and decreasing abilities via SALPR by the above-mentioned embodiment will be explained in more detail as follows.

Namely, the CRE introduced into the above-mentioned screening cell is a base sequence commonly present in a transcription regulatory region of a group of genes (cAMP inducing genes)whose expression is accelerated when the intracellular cAMP concentration increases. Therefore, when an adenylyl cyclase activating agent (e.g., FSK) is added to a screening cell, the intracellular cAMP concentration increases, which results in an increase in the amount of expression of the reporter gene located in the downstream of the CRE. The amount of expression of a reporter gene product can be easily measured by measuring luminescence derived from a luminescent substance generated from a substance reacted with the reporter gene product or fluorescence derived from a fluorescent protein produced as the reporter gene product.

Further, when a natural ligand of SALPR is added upon adding an adenylyl cyclase-activating agent, adenylyl cyclase activity suppression also occurs due to the action of the above-mentioned natural ligand on SALPR according to the present invention, in addition to the above-mentioned adenylyl cyclase activity stimulation due to the adenylyl cyclase-activating agent, which results in a decrease in the amount of the expression of the reporter gene product as compared to the case where the adenylyl cyclase activating agent alone is added. Therefore, if the screening is for a compound having body weight increasing activity, a compound which decreases the amount of expression of the reporter gene product (namely having the same activity as the natural ligand) can be selected by contacting the test substance alone, in place of the natural ligand which acts via SALPR in this screening system.

When the screening is carried out for a compound having a body weight decreasing activity, an adenylyl cyclase activating agent, a natural ligand of SALPR, and a test substance can be added to a screening cell. The amount of expression of the reporter gene product decreases due to the action of the natural ligand as compared to the case where the adenylyl cyclase activating agent alone is added; however, the decrease in the amount of expression of the reporter gene product is suppressed when the test substance antagonizes the action of the natural ligand. In this case, the test substance can be selected as a compound having a body weight decreasing activity.

Whether the action by a test substance is due to the action through the binding to SALPR can be easily confirmed. For example, in parallel with the above-mentioned test using a screening cell (namely, a cell which expresses SALPR on the cell membrane and contains a reporter gene with CRE located upstream of the 5' end), a similar test is carried out using a cell for control (for example, a cell which contains a reporter gene with CRE located upstream of the 5' end but does not express SALPR on the cell membrane). As a result, the cell for screening and the cell for control show the same phenomenon regarding the amount of expression of the reporter gene product when the action by the above-mentioned test substance is not due to the binding to SALPR, while the cell for screening and the cell for control show different phenomena regarding the amount of expression of the reporter gene product when the action by the above-mentioned test substance is due to the binding to SALPR.

Further, in another embodiment, a test substance influencing body weight control can be confirmed and determined by administering the test substance selected by the above-mentioned screening method to humans or organisms other than humans [for example, non-human mammals (e.g., cattle, monkeys, poultry, cats, mice rats, hamsters, pigs, canines), birds, reptiles, amphibians, fish, and insects] and measuring the amount of feeding, body weight, and indices of obesity (for example, percent body fat, BMI (body mass index), degree of obesity, body habitus, physical age, impedance, body fat weight, fat free mass, body water mass, body protein mass, muscle mass, inorganic mass, body cellular mass, muscle mass by the region of the body, water mass by the region of the body, BMR (basal metabolic rate), energy requirement, visceral-subcutaneous fat ratio (VSR), visceral fat weight, subcutaneous fat weight, visceral fat weight level, organ weight, changes in blood parameters, and the amounts of leptin, glucose, lipid, hormones, secretory peptides in the blood) after administration. The above-mentioned mammals are not limited to normal animals, but can also be genetic mutant animal models for disease (for example, morbid obesity models such as ob/ob mice, db/db mice, and Zucker fatty rats) and genetically modified animals. The test substance can be administered either orally or parenterally. Examples of the parenteral route include intravenous, intraarterial, subcutaneous, intraperitoneal, intratracheal, intrarectal, and intracerebral administrations, preferably administration into the cerebroventricle near the hypothalamus. As the indices for the screening, for example, the amount of feeding and indices of obesity as well as body weight can be effectively measured. Further, upon administration, conditions such as fasting, satiation, and excessive fat diet can be added.

The test substance can be administered in a single or divided dose per day and the administration or observation period can be from one day to several weeks.

Method of Screening for Compounds Involved in Obesity Control Using Relaxin-3 Receptor As a relaxin-3 receptor to be used in the present invention, among various receptors, a receptor which has an ability to bind relaxin-3 and exhibits various cell-stimulating activities of the relaxin-3 receptor expressing cell (e.g., intracellular calcium release, adenylyl cyclase activation, intracellular cAMP production, intracellular cGMP production, inositol phospholipid production, electrical potential change in the cell membrane, pH change in the vicinity of the cell membrane, phosphorylation of intracellular proteins, c-fos and c-jun induction/activation, arachidonic acid release) can be used.

More specifically, as a relaxin-3 receptor, a reported known receptor, for example, LGR7 (GenBank Accession No. NM_021634), SALPR (GenBank Accession No. NM_016568, also called GPCR135), or GPR100 (GenBank Accession No. AB_083593, also called hGPCR11 or GPCR142) can be used. Further, a partial polypeptide of these receptors is not particularly limited as long as it is usable in the screening method described later and a partial polypeptide having a binding ability to relaxin-3, a partial polypeptide comprising an amino acid sequence corresponding to the outside region of the cell membrane or the like can also be used.

The content of the present invention will be explained in detail below in this specification, referring to a screening method using SALPR as a preferred example of the present invention. Namely, the present invention is to provide a method of screening for a compound which binds to SALPR or its partial polypeptide and is involved in the control of obesity (stimulation or suppression of obesity). Further, whether a substance has an activity to stimulate or suppress obesity can be determined by allowing the test substance to act on SALPR or its partial polypeptide and measuring cell-stimulating activities.

SALPR or its partial polypeptide can be obtained by various known methods; for example, it can be prepared by a known genetic engineering method using a polynucleotide encoding SALPR (GenBank Accession No. NM_016568). In another embodiment, it can be obtained by a known polypeptide synthesis method, such as an ordinary method, e.g., a liquid phase method or solid phase method; an autosynthesizer can generally be used. Further, in another embodiment, a partial polypeptide of SALPR can be prepared by cleaving SALPR with an appropriate proteolytic enzyme.

The polypeptide encoding SALPR to be used in the present invention means a polypeptide comprising the amino acid sequence represented by SEQ ID NO: 4, a modified polypeptide functionally equivalent to a polypeptide comprising the amino acid sequence represented by SEQ ID NO: 4, or a polypeptide which comprises an amino acid sequence having 70% or more, preferably 80% or more, more preferably 85% or more, further preferably 90% or more, further more preferably 95% or more, particularly preferably 98% or more, and most preferably 99% or more, homology to the amino acid sequence represented by SEQ ID NO: 4 and exhibits substantially the same activities as relaxin-3 (for example, a binding ability to relaxin-3 and various cell-stimulating activities associated with the binding, or obesity controlling effect).

Here, the modified polypeptide functionally equivalent to a polypeptide comprising the amino acid sequence represented by SEQ ID NO: 4 means a polypeptide which comprises an amino acid sequence having one or more deletions, substitutions, insertions and/or additions of one or more (preferably one or several) amino acids in the polypeptide comprising the amino acid sequence represented by SEQ ID NO: 4 and exhibits substantially the same activities as SALPR (for example, a binding ability to relaxin-3 and various cell-stimulating activities associated with the binding, or obesity controlling effects).

Further, a partial polypeptide of SALPR can also be used as long as it has substantially the same activities as SALPR (for example, a binding ability to relaxin-3 and various cell-stimulating activities associated with the binding, or an obesity controlling activity).

The genetic engineering method will be explained in detail more specifically using SALPR below; however, its partial peptide can also be used as long as it is usable in the screening method described later.

A polynucleotide encoding SALPR is introduced into an appropriate host cell, the resulting transformant is cultured under the conditions for enabling the expression, then a polypeptide of interest can be isolated and purified from the culture by a method generally used for isolation and purification of an expressed protein, and thus SALPR is prepared. Examples of the method for the above-mentioned isolation and purification include ammonium sulphate salting-out, ion-exchange column chromatography using an ion-exchange cellulose, molecular sieving column chromatography using a molecular sieving gel, affinity column chromatography using a protein-A binding polysaccharide, dialysis and lyophilization.

A polynucleotide encoding SALPR to be used in the present invention is not particularly limited as long as it is a polynucleotide encoding a polypeptide to be used in the present invention.

The term "polynucleotide" as used herein includes both DNA and RNA. More specifically, the polynucleotide used in the present invention is selected from the group consisting of the following (a) to (e):
(a) a polynucleotide comprising the base sequence represented by SEQ ID NO: 3;
(b) a polynucleotide encoding "a polypeptide comprising the amino acid sequence represented by SEQ ID NO: 4";
(c) a polynucleotide encoding "a polypeptide which comprises the amino acid sequence represented by SEQ ID NO: 4 and exhibits substantially the same activities as the above-mentioned SALPR";
(d) a polynucleotide encoding "a polypeptide which comprises an amino acid sequence having deletions, substitutions, insertions and/or additions of one or more (preferably one or several) amino acids at one or more (preferably one or several) sites of the amino acid sequence represented by SEQ ID NO: 4 and exhibits substantially the same activities as the above-mentioned SALPR"; and
(e) a polynucleotide which hybridizes with a polynucleotide comprising the base sequence represented by SEQ ID NO: 3 under stringent conditions and encodes a polypeptide which exhibits substantially the same activities as the above-mentioned SALPR.

According to one embodiment of the present invention, the polynucleotide to be used in the present invention is a polynucleotide comprising the base sequence represented by SEQ ID NO: 3. The above-mentioned polynucleotide represented by SEQ ID NO: 3 encodes SALPR comprising the amino acid sequence represented by SEQ ID NO: 4.

According to another embodiment of the present invention, the polynucleotide to be used in the present invention is a polynucleotide encoding "a polypeptide which comprises an amino acid sequence having deletions, substitutions, insertion and/or additions of one or more (preferably one or several) amino acids at one or more (preferably one or several) sites of the amino acid sequence represented by SEQ ID NO: 4 and exhibits substantially the same activities as the above-mentioned SALPR." Here the number of amino acid residues which can be deleted, substituted, inserted and/or added is, for example, 1 to 30, preferably 1 to 20, more preferably 1 to 10, further more preferably 1 to 5, and most preferably 1 to 2.

According to still another embodiment of the present invention, the polynucleotide to be used in the present invention is a polynucleotide which hybridizes with a polynucleotide comprising the base sequence represented by SEQ ID NO: 3 under stringent conditions and encodes a polypeptide which exhibits substantially the same activities as the above-mentioned SALPR. Further, according to still another embodiment of the present invention, the polynucleotide to be used in the present invention is a polynucleotide which hybridizes with a polynucleotide comprising the base sequence represented by SEQ ID NO: 3 under stringent conditions and encodes a polypeptide which exhibits substantially the same activities as the above-mentioned SALPR.

A plasmid to be used in the above-mentioned transformation is not particularly limited as long as it contains a polynucleotide encoding the above-mentioned SALPR; for example, it can be obtained by inserting said polynucleotide into a known expression vector appropriately selected depending on a host cell used.

The above-mentioned transformant is also not particularly limited as long as it contains a polynucleotide encoding the above-mentioned SALPR; for example, it can be a transformant in which said polynucleotide is incorporated into a chromosome of the host cell, a transformant which contains said polynucleotide in the form of a plasmid, or a transformant which does not express SALPR. Said transformant can be obtained, for example, by transforming a desired host cell with the above-mentioned plasmid or the above-mentioned polynucleotide itself.

Examples of the above-mentioned host cell include generally used known microorganisms such as *Escherichia coli* (e.g., *E. coli* JM109) and yeasts (e.g., *Saccharomyces cerevisiae* W303) and known culture cells such as animal cells (e.g., CHO cells, HEK-293 cells, COS cells) and insect cells (e.g., BmN4 cells).

Examples of the above-mentioned expression vector include pUC, pTV, pGEX, pKK, and pTrcHis for *E. coli*; pEMBLY and pYES2 for yeasts; pcDNA3, pMAMneo and pBabe Puro for CHO cells, HEK-293 cells and COS cells; and a vector having the polyhedrin promoter of Bombyx mori nuclear polyhedrosis virus (BmNPV) (e.g., pBK283) for BmN4 cells.

A cell containing SALPR is not particularly limited as long as it expresses SALPR on the surface of the cell membrane and can be obtained, for example, by culturing the above-mentioned transformant (namely, the cell transformed with a plasmid containing a polynucleotide encoding SALPR) under the conditions enabling the expression of SALPR, or by injecting RNA encoding SALPR into an appropriate cell and culturing it under the conditions enabling the expression of SALPR.

A cell membrane fraction containing SALPR to be used in the present invention can be obtained, for example, by disrupting the cells expressing SALPR according to the present invention and then isolating a fraction rich in the cell membrane. Examples of the method of disrupting the cells include a method of disrupting the cells using a homogenizer (e.g., a Potter-Elvehiem-type homogenizer), disruption by a Waring blender or Polytron (Kinematica), ultrasonic disruption, and disruption by ejecting the cells from a fine nozzle under pressure using a French press or the like. Further, examples of the method for fractionating the cell membrane include a fractionation method by centrifugation, such as differential centrifugation and density gradient centrifugation.

In a method of screening for a compound which stimulates or suppresses obesity via SALPR according to the present invention, SALPR, the above-mentioned cell membrane fraction (namely, a cell membrane fraction containing SALPR) or the above-mentioned cell (or the cell containing SALPR) can be used.

Further, a screening method according to the present invention includes and utilizes a method of examining whether a test substance binds specifically to SALPR and a method of examining cell-stimulating activities generated by the binding of the test substance to SALPR (for example, intracellular calcium release, adenylyl cyclase activation, intracellular cAMP production, intracellular cGMP production, inositol phospholipid production, electrical potential change in the cell membrane, pH change in the vicinity of the cell membrane, phosphorylation of intracellular proteins, c-fos and c-jun induction/activation, and arachidonic acid release).

In the screening method according to the present invention, for example, SALPR, the above-mentioned cell membrane fraction or the above-mentioned cell is contacted with a test substance to analyze whether SALPR, the above-mentioned cell membrane fraction, or the above-mentioned cell binds to the test substance, and thus the screening for the compound can be achieved without distinction between obesity stimulating and suppressing abilities via SALPR.

Specifically, in the presence or absence of the test substance, SALPR, the above-mentioned cell membrane fraction or the above-mentioned cell is contacted with a labeled natural ligand (namely relaxin-3) to compare the amount of specific binding of the above-mentioned natural ligand via SALPR, the above-mentioned cell membrane fraction or the above-mentioned cell, and thus the screening for the compound can be achieved without distinction between obesity stimulating and suppressing abilities via SALPR. Namely, when the above-mentioned test substance has obesity stimulating or suppressing abilities via SALPR, the amount of specific binding of the natural ligand via SALPR, the above-mentioned cell membrane fraction or the above-mentioned cell in the presence of the test substance decreases as compared to the corresponding amount of the specific binding in the absence of the test substance.

In the screening method according to the present invention, when the amount of specific binding of the natural ligand via SALPR, the above-mentioned cell membrane fraction or the above-mentioned cell is compared, a labeled natural ligand can be used as the above-mentioned natural ligand. For the above-mentioned labeling, a radioactive isotope, an enzyme, a fluorescent substance, a luminescent substance and the like can be used. Examples of the radioactive isotope include [$^3$H], [$^{14}$C], [$^{125}$I], and [$^{35}$S]. Examples of the enzyme include β-galactosidase, alkaline phosphatase, and peroxidase. Examples of the fluorescent substance include fluorescein isothiocyanate and BODIPY. Examples of the luminescent substance include luciferin and lucigenin. Occasionally, the biotin-avidin system can be used for binding of the natural ligand and the labeling substance.

Thus, the screening method according to the present invention can screen for a compound which binds to SALPR, the above-mentioned cell membrane fraction or the above-mentioned cell to inhibit their binding to the natural ligand, without distinction between obesity stimulating and suppressing abilities via SALPR.

In another embodiment of the screening method according to the present invention, the above-mentioned cell is contacted with a labeled natural ligand (namely relaxin-3) under conditions in the presence or absence of a test substance to compare the amount of specific binding of the above-mentioned natural ligand via the above-mentioned cell under the above-mentioned conditions and then further compare a specific cell-stimulating activity of the above-mentioned natural ligand under these conditions, thereby enabling the screening for a compound with distinction between obesity stimulating and suppressing abilities via SALPR.

In the above-mentioned embodiment, a substance which binds to the above-mentioned cell and exhibits the cell-stimulating activity via a receptor contained in the above-mentioned cell can be selected as a compound which stimulates obesity via SALPR.

On the other hand, in the above-mentioned embodiment, a test substance which inhibits binding of the above-mentioned cell and the natural ligand but does not exhibit the cell-stimulating activity can be selected as a compound which suppresses obesity via SALPR.

The screening method according to the present invention can be carried out using, for example, suppression of adenylyl cyclase activity as a cell-stimulating activity.

In the screening method of this embodiment, for example, cAMP produced in a cell by the activation of adenylyl cyclase can be measured using a known method, thereby enabling the screening for a compound with distinction between obesity stimulating and suppressing abilities via SALPR. This embodiment utilizes intracellular signal transmission generated by the binding of the natural ligand to SALPR, namely, the suppression of adenylyl cyclase activity which is one of cell-stimulating activities of SALPR. Specifically, when the natural ligand binds to SALPR, a Gi family that is a member of G protein family coupled with SALPR suppresses adenylyl cyclase to decrease the amount of cyclic AMP (cAMP, produced from ATP by adenylyl cyclase) produced in the cell.

For example, the intracellular cAMP concentration increases when an adenylyl cyclase-activating agent [such as forskolin (FSK)] is added to mammal-derived cells (for example, HEK-293 cells or CHO cells) in which SALPR is expressed on the cell membrane (preferably, excessively expressed by introducing an expression vector containing SALPR).

Further, when a natural ligand of SALPR is added upon adding an adenylyl cyclase-activating agent, adenylyl cyclase activity suppression also occurs due to the action of the above-mentioned natural ligand on SALPR according to the present invention, in addition to the above-mentioned adenylyl cyclase activity stimulation due to the adenylyl cyclase-activating agent, which results in a decrease in the cAMP production as compared to the case where the adenylyl cyclase activating agent alone is added. Therefore, when the screening is carried out for a compound having obesity stimulating activity, a compound which decreases the cAMP production (namely having the same activity as the natural ligand) can be selected by contacting the test substance alone, in place of the natural ligand which acts via SALPR in this screening system.

When the screening is carried out for a compound having obesity suppressing activity, an adenylyl cyclase activating agent, a natural ligand of SALPR, and a test substance can be added to cells for screening. The cAMP production decreases due to the action of the natural ligand as compared to the case where the adenylyl cyclase activating agent alone is added; however, the decrease in the cAMP production is suppressed when the test substance antagonizes the action of the natural ligand. In this case, this test substance can be selected as a compound having obesity suppressing activity.

As a method for measuring the amount of intracellular cAMP, an immunoassay or the like can be used; for example, a commercial kit for cAMP quantification can also be used.

In another embodiment of the screening method, for example, screening for a compound can be achieved with distinction between obesity stimulating and suppressing abilities via SALPR, by using a cell (occasionally referred to as "screening cell" hereinafter) in which SALPR is expressed on the cell membrane (preferably excessively expressed by introducing an expression vector containing SALPR) and a reporter gene [for example, the alkaline phosphatase gene, the luciferase gene, the β-lactamase gene, the nitroreductase gene, the chloramphenicol acetyl transferase gene, the β-galactosidase gene, or a fluorescent protein gene such as GFP (green fluorescent protein) gene] having a cAMP responding element (CRE) located upstream of the 5' end is contained. This embodiment utilizes the fact that the transcription of the reporter gene which has the CRE introduced into the above-mentioned screening cell, in the promoter region is suppressed as a result of the decrease in the above-mentioned cAMP production.

A process of screening for a compound with distinction between obesity stimulating and suppressing abilities via SALPR by the above-mentioned embodiment will be explained in more detail as follows.

Namely, the CRE introduced into the above-mentioned screening cell is a base sequence commonly present in a transcription regulatory region of a group of genes (cAMP inducing genes) whose expression is accelerated when the intracellular cAMP concentration increases. Therefore, when an adenylyl cyclase activating agent (e.g., FSK) is added to a screening cell, the intracellular cAMP concentration increases, which results in an increase in the amount of expression of the reporter gene located in the downstream of the CRE. The amount of expression of a reporter gene product can be easily measured by measuring luminescence derived from a luminescent substance generated from a substance reacted with the reporter gene product or fluorescence derived from a fluorescent protein produced as the reporter gene product.

Further, when a natural ligand of SALPR is added upon adding an adenylyl cyclase-activating agent, adenylyl cyclase activity suppression also occurs due to the action of the above-mentioned natural ligand on SALPR according to the present invention, in addition to the above-mentioned adenylyl cyclase activity stimulation due to the adenylyl cyclase-activating agent, which results in a decrease in the amount of the expression of the reporter gene product as compared to the case where the adenylyl cyclase activating agent alone is added. Therefore, if the screening is for a compound exhibiting obesity stimulating activity, a compound which decreases the expression of the reporter gene product (namely having the same activity as the natural ligand) can be selected by contacting the test substance alone, in place of the natural ligand which acts via SALPR in this screening system.

When the screening is carried out for a compound having obesity suppressing activity, an adenylyl cyclase activating agent, a natural ligand of SALPR, and a test substance can be added to a screening cell. The amount of expression of the reporter gene product decreases due to the action of the natural ligand as compared to the case where the adenylyl cyclase activating agent alone is added; however, the decrease in the amount of expression of the reporter gene product is suppressed when the test substance antagonizes the action of the natural ligand. In this case, the test substance can be selected as a compound having obesity suppressing activity.

Whether the action by a test substance is due to the action through the binding to SALPR can be easily confirmed. For example, in parallel with the above-mentioned test using a screening cell (namely, a cell which expresses SALPR on the cell membrane and contains a reporter gene with CRE located upstream of the 5' end), a similar test is carried out using a cell for control (for example, a cell which contains a reporter gene with CRE located upstream of the 5' end but does not express SALPR on the cell membrane). As a result, the cell for screening and the cell for control show the same phenomenon regarding the amount of expression of the reporter gene product when the action by the above-mentioned test substance is not due to the binding to SALPR, while the cell for screening and the cell for control show different phenomena regarding the amount of expression of the reporter gene product when the action by the above-mentioned test substance is due to the binding to SALPR.

Further, in another embodiment, a test substance influencing activity causing obesity can be confirmed and determined by administering the test substance selected by the above-mentioned screening method to humans or organisms other than humans [for example, non-human mammals (e.g., cattle, monkeys, poultry, cats, mice rats, hamsters, pigs, canines), birds, reptiles, amphibians, fish, and insects] and measuring the amount of feeding, body weight, and indices of obesity (for example, percent body fat, BMI (body mass index)), degree of obesity, body habitus, physical age, impedance, body fat weight, fat free mass, body water mass, body protein mass, muscle mass, inorganic mass, body cellular mass, muscle mass by the region of the body, water mass by the region of the body, BMR (basal metabolic rate), energy requirement, visceral-subcutaneous fat ratio (VSR), visceral fat weight, subcutaneous fat weight, visceral fat weight level, organ weight, changes in blood parameters, and the amounts of leptin, glucose, lipid, hormones, secretory peptides in the blood) after administration. The above-mentioned mammals are not limited to normal animals, but can also be genetic mutant animal models for disease (for example, morbid obesity models such as ob/ob mice, db/db mice, and Zucker fatty rats) and genetically modified animals. The test substance can be administered either orally or parenterally. Examples of the parenteral route include intravenous, intraarterial, subcutaneous, intraperitoneal, intratracheal, intrarectal, and intracerebral administration, preferably administration into the cerebroventricle near the hypothalamus. As the indices for the screening, for example, the amount of feeding and body weight as well as indices of obesity can be effectively measured. Further, upon administration, conditions such as fasting, satiation, and excessive fat diet can be added.

The test substance can be administered in a single or divided dose per day and the administration or observation period can be from one day to several weeks.

Here, a test substance to be used in the present invention can be any compound and can be, for example, an expression product of gene library, a synthetic low molecular compound library, nucleic acid (oligo DNA, oligo RNA), a synthetic peptide library, an antibody, a bacterial releasing substance, a fluid extract of cells (microorganisms, plant cells, or animal cells), a culture supernatant of cells (microorganisms, plant cells, animal cells), a purified or partially purified polypeptide, an extract derived from a marine organism, plant or animal, soil, or a random phage peptide display library.

Screening Kit

A screening kit of the present invention contains a relaxin-3 receptor, preferably SALPR or the above-mentioned cell membrane fraction (i.e., a cell membrane fraction containing SALPR), or the above-mentioned cell (i.e., a cell containing SALPR). The above-mentioned screening kit may further contain various reagents, such as labeled relaxin-3, non-labeled relaxin-3, a buffer solution for binding reaction, and/or a buffer solution for washing, an instruction, and implements, if necessary.

Specifically, the above-mentioned screening kit contains SALPR, the above-mentioned cell membrane fraction, or the above-mentioned cell and may contain a labeled natural ligand (i.e., relaxin-3), a non-labeled natural ligand, and/or a buffer solution for binding reaction, an instruction, and implements, if necessary.

A screening kit of another embodiment of the present invention comprises a cell which expresses a relaxin-3 receptor, preferably SALPR, on the cell membrane (preferably expresses excessively by introducing an expression vector containing SALPR) and moreover contains a reporter gene with a cAMP responding element (CRE) located upstream of the 5' end, and if necessary, may comprise a substrate for alkaline phosphatase, luciferase or the like, an adenylyl cyclase activating agent (e.g., FSK), a natural ligand (i.e., relaxin-3), and/or a buffer solution for binding reaction, an instruction, and implements.

A screening kit of further another embodiment of the present invention comprises a cell which expresses a relaxin-3 receptor, preferably SALPR, on the cell membrane (preferably expresses excessively by introducing an expression vector containing SALPR) and moreover contains a reporter gene with a cAMP responding element (CRE) located upstream of the 5' end and a cell which contains a reporter gene with a CRE located upstream of the 5' end but does not express SALPR on the cell membrane and if necessary, may comprise a substrate of a reporter gene product, an adenylyl cyclase activating agent (e.g., FSK), and/or a buffer solution for binding reaction, an instruction, and implements.

Medicine Containing a Compound Obtained by the Screening Method of the Present Invention A compound obtained by the screening method of the present invention is a compound which stimulates or suppresses feeding, a compound which increases or decreases body weight, or a compound which stimulates or suppresses obesity. Said compound can be in the form of a salt, for example, a pharmaceutically acceptable salt. Accordingly, a compound obtained by the screening method of the present invention, or its salt, can be used as a medicine for the treatment of diseases caused by some abnormalities in feeding (or appetite) control, diseases caused by some abnormalities in controlling body weight, diseases caused by some abnormalities in controlling obesity, and diseases caused by abnormalities in relaxin-3 or a polynucleotide encoding relaxin-3. Further, it can be used as a therapeutic medicine for the purpose of recovering feeding (or appetite) and/or body weight which is increased or decreased due to onset of various diseases or treatment of various diseases (for example, during or after an operation). Examples of the above-mentioned diseases include diseases involved in the movement or function of the alimentary tract (for example, diarrhea, constipation, functional constipation, hypersensitive intestinal syndrome, and conditions which require defecation stimulation to remove intestinal contents upon alimentary canal examination or before or after an operation), diseases involved in controlling immune functions (for example, chronic rheumatoid arthritis, systemic erythematodes, kidney diseases, scleroderma, atopic dermatitis, bronchial asthma, multiple sclerosis, rheumatic interstitial pneumonia, sarcoidosis, Crohn's disease, inflammatory colitis, liver cirrhosis, chronic hepatitis, fulminant hepatitis, encephalomyelitis, and myasthenia gravis), diseases involved in energy metabolisms (for example, diabetes, obese diabetes, abnormalities in glucose tolerance, ketosis, acidosis, diabetic neuropathy, diabetic nephropathy, diabetic retinopathy, hyperlipidemia, arteriosclerosis, cardiac angina, myocardial infarction, obesity, morbid obesity, feeding disorders, and anorexia), AIDS, cancers, and cachexia.

According to the screening method of the present invention, there is provided a compound having an activity to inhibit cell-stimulating activities via a relaxin-3 receptor, preferably SALPR or its partial polypeptide (SALPR-inhibiting activity), more specifically, cell-stimulating activities caused by the binding of a natural ligand to SALPR or its partial polypeptide (for example, intracellular calcium release, adenylyl cyclase activation, intracellular cAMP production, intracellular cGMP production, inositol phospholipid production, electrical potential change in the cell membrane, pH change in the vicinity of the cell membrane, phosphorylation of intracellular proteins, c-fos and c-jun induction/activation, and arachidonic acid release). Examples of the medicine containing such a compound include feeding-suppressing agents, body weight-reducing agents, fat-reducing agents, therapeutic agents for the treatment of obesity, and therapeutic agents for the treatment of diabetes.

The compound thus obtained or its salt can be used alone; however, it can also be used as a pharmaceutical composition by admixing with a pharmaceutically acceptable carrier. The percentage of the active ingredient in the carrier can vary between 1 to 90% by weight. The above-mentioned medicine can be administered in various forms either orally or parenterally (for example, intravenous, intramuscular, subcutaneous, rectal, and dermal administrations) to humans or organisms other than humans [for example, non-human mammals (e.g., cattle, monkeys, poultry, cats, mice, rats, hamsters, pigs, canines), birds, reptiles, amphibians, fish, and insects]. Accordingly, the pharmaceutical composition containing a compound obtained by the present invention or its salt is prepared into an appropriate form depending on the administration route. Specifically, it can be formulated into oral formulations such as tablets, capsules, granules, dispersible powders and syrups or parenteral formulations such as injections, intravenous drips, liposome compositions, and suppositories. These formulations can be manufactured by an ordinary method using commonly used excipients, fillers, binding agents, wetting agents, disintegrating agents, surfactants, lubricants, dispersing agents, buffering agents, preservatives, solubilizing agents, antiseptics, flavoring agents, analgesic agents, stabilizers, and the like. Examples of the above-mentioned non-toxic additives to be used include lactose, fructose, glucose, starch, gelatin, magnesium stearate, methylcellulose or its salts, ethanol, citric acid, sodium chloride, and sodium phosphate.

Their form and amount of the administration depend on the selection of the compound obtained by the screening method of the present invention or its salt, the subject to be administered, the administration route, properties of the preparation, conditions of the patient, and physician's judgment. However, the appropriate dose per 1 kg of patient's body weight ranges, for example, from about 1.0 to 1,500 μg, preferably from about 10 to 500 μg. The amount of necessary dosage is expected to vary widely considering that the efficiency is different depending on the route of administration. For example, the dose required for oral administration is expected to be higher than that for intravenous injection. Such variations in the dose level can be adjusted using a standard empirical optimizing procedure well understood in the art.

Substance Inhibiting Activity of Relaxin-3 and its Use

A substance which inhibits the activity of relaxin-3 used in the present invention (i.e., relaxin-3, a modified polypeptide, or a homologous polypeptide) can suppress or inhibit feeding stimulation, body weight gain, and obesity. Accordingly, a substance which inhibits the expression of relaxin-3 has a potential to be used for controlling functions associated with feeding-control and body weight control (e.g., energy metabolism control, growth) and obesity, in vivo, ex vivo, and in vitro, by relaxin-3.

The substance which inhibits the activity of relaxin-3 used in the present invention is not particularly limited as long as it has the above-mentioned activity and can be, for example, a substance which inhibits the expression of relaxin-3, such as a DNA having an antisense sequence of a base sequence encoding relaxin-3, a double stranded RNA having a base sequence encoding relaxin-3 (small interfering RNA (siRNA)) or a ribozyme; or a substance which interacts with relaxin-3 or a relaxin-3 receptor (preferably SALPR) to inhibit the activity of relaxin-3, such as a relaxin-3 antibody, a glycoprotein, or a compound obtained by the above-mentioned screening method.

The above-mentioned substance can be in the form of a salt, for example, a pharmaceutically acceptable salt. Accordingly, a substance which inhibits the activity of relaxin-3 (i.e., relaxin-3, a modified polypeptide, or a homologous polypeptide) or its salt can be used as a medicine for the treatment of diseases caused by some abnormalities in feeding (or appetite) control, diseases caused by some abnormalities in controlling body weight, diseases caused by some abnormalities in controlling obesity, and diseases caused by abnormalities in relaxin-3 or a polynucleotide encoding relaxin-3. Further, it can be used as a therapeutic medicine for the purpose of reducing feeding (or appetite) and/or body weight which is increased due to onset of diseases or treatment of diseases (for example, during or after an operation). Examples of the above-mentioned diseases include diseases involved in the movement or function of the alimentary tract (e.g., diarrhea, constipation, functional constipation, hypersensitive intestinal syndrome, and conditions which require defecation stimulation to remove intestinal contents upon alimentary tract examination or before or after an operation), diseases involved in controlling immune functions (for example, chronic rheumatoid arthritis, systemic erythematodes, kidney diseases, scleroderma, atopic dermatitis, bronchial asthma, multiple sclerosis, rheumatic interstitial pneumonia, sarcoidosis, Crohn's disease, inflammatory colitis, liver cirrhosis, chronic hepatitis, fulminant hepatitis, encephalomyelitis, and myasthenia gravis), and diseases involved in energy metabolisms (for example, diabetes, obese diabetes, abnormalities in glucose tolerance, ketosis, acidosis, diabetic neuropathy, diabetic nephropathy, diabetic retinopathy, hyperlipidemia, arteriosclerosis, cardiac angina, myocardial infarction, obesity, morbid obesity, and feeding disorders). Preferably, it can be used as a feeding-controlling agent, a body weight-reducing agent, a fat-reducing agent, a therapeutic agent for the treatment of obesity, or a therapeutic agent for the treatment of diabetes.

The mechanisms in which an antisense nucleic acid suppresses the expression of a target gene are, for example, (1) inhibition of transcription initiation by triple stranded chain formation, (2) suppression of transcription by hybrid formation at the site of local open loop structure formed by RNA polymerase, (3) inhibition of transcription by hybrid formation with RNA being synthesized, (4) suppression of splicing by hybrid formation at an intron-exon junction, (5) suppression of splicing by hybrid formation at the site of spliceosome formation, (6) suppression of transfer of mRNA into the cytoplasm by hybrid formation with the mRNA, (7) suppression of splicing by hybrid formation at the capping site or the poly-A addition site, (8) suppression of translation initiation by hybrid formation at the translation initiation factor binding site, (9) suppression of translation by hybrid formation at the ribosome binding site, (10) suppression of peptide chain elongation by hybrid formation at the mRNA translation region or the polysome binding site, and (11) suppression of gene expression by hybrid formation at the nucleic acid/protein interaction site (New Experimental Course of Biochemistry 2, Nucleic Acid IV, Gene Replication and Expression, by Hirashima and Inoue, compiled by the Japanese Biochemical Society, Tokyo Kagaku Dojin, pp. 319-347, 1993).

The antisense nucleic acid of relaxin-3 to be used in the present invention can be any nucleic acid which suppresses gene expression by any of the above-mentioned mechanisms (1) to (11). Namely, it can contain not only a translation region of a gene to inhibit expression but also an antisense sequence to a sequence of a non-translation region. DNA encoding the antisense nucleic acid can be used by connecting it with an appropriate regulating sequence to enable its expression. The antisense nucleic acid is not necessarily completely complementary to the translation region or non-translation region of a target gene as long as it effectively inhibits the expression of the target gene. Such antisense nucleic acid is at least 15 bp or more, preferably 100 bp or more, more preferably 500 bp or more, and generally has a chain length of 3000 bp or less, preferably 2000 bp or less, more preferably 1000 bp or less, and a homology of preferably 90% or more, more preferably 95% or more, to the complementary chain of the transcription product of the target gene. Such antisense nucleic acid can be prepared based on the relaxin-3 sequence information using the phosphorothioate method (Stein (1988) Nucleic Acids Res. 16: 3209-21) or the like.

Ribozyme is the general term for catalysts composed of RNA and can be loosely divided into large ribozymes and small ribozymes. The large ribozymes are enzymes which cleave phosphodiester bonds of nucleic acid to leave 5'-phosphate and 3'-hydroxyl groups at the reaction sites after the reaction. The large ribozymes are further classified into (1) group I intron RNAs which carry out a transesterification reaction at the 5' splice site by guanosine, (2) group II intron RNAs which self-splice by two step reactions via lariat structure, and (3) RNA components of ribonuclease P which cleaves a tRNA precursor on the 5' side by hydrolysis. On the other hand, the small ribozymes are relatively small structure units (about 40 bp) and produce 5'-hydroxyl groups and 2',3'-cyclic phosphates by cleaving RNAs. Small ribozymes include hammerhead-type ribozymes (Koizumi et al. (1988) FEBS Lett. 228: 225), hairpin-type ribozymes (Buzayan (1986) Nature 323: 349; Kikuchi and Sasaki (1992) Nucleic Acids Res. 19: 6751; Hiroshi Kikuchi (1992) Kagaku to Seibutsu 30: 112) and the like. Since ribozymes can be easily modified and synthesized, various improving methods are known. For example, a hammerhead-type ribozyme which recognizes and cleaves a base sequence UC, UU or UA in a target RNA can be created by designing the substrate binding site of a ribozyme to be complementary to an RNA sequence near the target site (Koizumi et al. (1988) FEBS Lett. 228: 225; Makoto Koizumi and Eiko Otsuka (1990) Tampakushitsu Kakusan Koso 35: 2191; Koizumi et al. (1989) Nucleic Acids Res. 17: 7059). Hairpin-type ribozymes can also be designed and produced according to known methods (Kikuchi and Sasaki (1992) Nucleic Acids Res. 19: 6751; Hiroshi Kikuchi (1992) Kagaku to Seibutsu 30: 112).

In 1998, a phenomenon (RNA interference) in which RNAs interfere with each other to lose their function in *Caenorhabditis elegance* was observed (Fire et al. (1998) Nature 391: 806-11). The RNA interference is a phenomenon in which RNA having the same base sequence is decomposed by introducing a double-stranded synthetic RNA into a cell. Later research suggested that RNA silencing phenomena such as RNA interference are cellular mechanisms to eliminate defective mRNAs and to defend against molecular parasites such as transposons and viruses. Today, double-stranded RNAs (small interfering RNAs; siRNAs) areutilized as a tool to suppress expression of many genes and a method of treating or preventing diseases by controlling the expression of disease causative genes or the like using siRNA has been under study. The siRNA of the present invention is not particularly limited as long as it inhibits the transcription of mRNA of relaxin-3. Generally, an siRNA is a combination of a sense strand and an antisense strand of a target mRNA and has a length of from at least 10 nucleotides to the same number of nucleotides as the target mRNA. The length is preferably 15 to 75, more preferably 18 to 50, further more preferably 20 to 25 nucleotides. In order to suppress the expression of relaxin-3, siRNA can be introduced into a cell by a known method. For example, DNA encoding two RNA strands composing an siRNA on a single strand is designed and incorporated into an expression vector, a cell is transformed with the resulting expression vector, and thus the siRNA can be expressed in the cell as a double-stranded RNA having a hairpin structure. Plasmid expression vectors which continuously produce siRNAs by transfection have also been designed (For example, RNAi-Ready pSIREN Vector, RNAi-Ready pSIREN-RetroQ Vector (BD Biosciences Clontech)).

Base sequences of siRNAs can be designed, for example, using a computer program on the Ambion website (http://www.ambion.com/techlib/misc/siRNA_finder.html). Kits for screening for functional siRNAs and the like (for example, BD Knockout RNAi System (BD Biosciences Clontech)) are also commercially available for use.

In gene therapy to suppress intracellular gene expression in a patient, an antisense nucleic acid of the present invention, a ribozyme and an siRNA can directly be administered into the tissue or a vector having a structure which is so constructed as to express these elements (for example, virus-derived vectors, such as retrovirus, adenovirus, and adeno-associated virus vectors and nonviral vectors, such as liposomes) can directly be administered into the tissue (in vivo method). The administration can be performed by injection into the tissue site, for example, by intramuscular injection, subcutaneous injection, intraarterial injection, or intravenous injection.

Alternatively, in advance, a vector having a structure which is so constructed as to express an antisense nucleic acid of the present invention, a ribozyme and an siRNA can be introduced into cells ex vivo. The cells thus obtained are injected in to patient's tissue, for example, by intramuscular injection, subcutaneous injection, intraarterial injection, or intravenous injection (ex vivo method). The cells used can be heterologous or homologous, preferably homologous, with those of the patient, and more preferably cells taken from the patient.

An antisense nucleic acid of the present invention, a ribozyme and an siRNA or any vector which is so constructed as to express these elements can be used alone; however, they can be admixed with a pharmaceutically acceptable carrier to be used as a pharmaceutical composition (e.g., a feeding-suppressing agent, a therapeutic agent for the treatment of obesity, a therapeutic agent for the treatment of diabetes). For example, when administered in the form of an injectable agent, the pharmaceutical composition can contain distilled water, a solution of a salt such as sodium chloride or a mixture of sodium chloride and an inorganic salt, a solution of a sugar such as mannitol, lactose, dextran, and glucose, a solution of an amino acid such as glycine and arginine, a mixed solution of an organic acid solution or a salt solution and a glucose solution, and the like.

The amount of administration varies depending on the body weight and age of the patient, symptomatic conditions, the form of administration, and the like; however, the amount of dose can be appropriately selected by those skilled in the art.

Antibodies to be used in the present invention include monoclonal antibodies, polyclonal antibodies, and antibody fragments.

A monoclonal antibody to be used in the present invention can be obtained by a known procedure except that relaxin-3 (namely, relaxin-3, a modified polypeptide, or a homologous polypeptide) or a partial fragment thereof is used as an antigen for immunization and an antigen for screening. For example, a mouse is immunized with the above-mentioned antibody for immunization, splenocytes obtained from the mouse and mouse myeloma cells are subjected to cell fusion by a cell fusion method (Nature, 256, 495 (1975)) or an electric cell fusion method (J. Immunol. Method, 100, 181-189 (1987)), the fused cells are subjected to screening using the above-mentioned antigen for screening, and thus a hybridoma for producing the monoclonal antibody to be used in the present invention can be obtained.

As a medium to culture the above-mentioned hybridoma, any medium which is appropriate to culture the hybridoma, preferably a Dulbecco's modified Eagle's minimum essential medium supplemented with fetal calf serum, L-glutamine, L-pyruvic acid and antibiotics (penicillin G and streptomycin), can be used. The above-mentioned hybridoma can be cultured in a medium in an atmosphere of 5% $CO_2$ at 37° C. for about 3 days. Alternatively, it can be cultured intraperitoneally in a mouse for about 14 days.

From the culture fluid or mouse abdominal fluid thus obtained, the above-mentioned monoclonal antibody can be isolated and purified by an ordinary protein isolation and purification method. Examples of such method include ammonium sulphate salting-out, ion-exchange column chromatography using ion-exchange cellulose, molecular sieving column chromatography using a molecular sieving gel, affinity column chromatography using a protein-A binding polysaccharide, dialysis and lyophilization.

Further, a polyclonal antibody to be used in the present invention can also be prepared by a known procedure, for example, as described below, except that relaxin-3 (namely, relaxin-3, a modified polypeptide, or a homologous polypeptide) or a partial fragment thereof is used as an antigen for immunization and an antigen for screening. Specifically, an emulsion of physiological saline containing an antigen mixed and emulsified with an equal amount of Freund's complete adjuvant or incomplete adjuvant or an equivalent thereof such as Hunter's TiterMax™ (Funakoshi) is administered to a mammal (particularly a rabbit or goat) either subcutaneously, intraperitoneally, or intramuscularly (primary immunization). Thereafter, the immunization is carried out in the same manner several times at 2 to 4 weeks intervals. One to two weeks after the last immunization, the blood is taken from the carotid artery or heart of the mammal and the serum can be prepared by salting out with ammonium sulfate.

An antibody fragment to be used in the present invention is a partial fragment of the above-mentioned antibody (including a monoclonal antibody and a polyclonal antibody) and not particularly limited as long as it has the same reaction specificity as the original antibody. Examples of the antibody fragment according to the present invention include Fab, Fab', $F(ab')_2$ and Fv. An antibody fragment to be used in the present invention can be obtained, for example, by digesting the monoclonal antibody or polyclonal antibody obtained by the above-mentioned method using a proteolytic enzyme (e.g., trypsin) according to an ordinary method and then subjecting the resulting product to an ordinary protein isolation and purification method.

Further, according to another embodiment, an antibody to be used in the present invention can be obtained by the method described in WO 01/068862 and Japanese Patent Laid-open No. 2002-345468 specification. A known relaxin-3 antibody, for example, an antibody described in an example of Japanese Patent Laid-open No. 2002-345468 (monoclonal antibody HK4-144-10), can also be used.

An antibody to be used in the present invention can also be used as a pharmaceutical composition, such as a feeding (or appetite) suppressing agent, a therapeutic agent for the treatment of obesity, and a therapeutic agent for the treatment of diabetes. The antibody to be used in the present invention can be used as a pharmaceutical composition by admixing with a pharmaceutically acceptable carrier. The percentage of the active ingredient in the carrier can vary between 1 to 90% by weight. Further, the above-mentioned medicine can be administered in various forms either orally or parenterally (for example, intravenous, intramuscular, subcutaneous, rectal, or dermal administration) to humans or organisms other than humans [for example, non-human mammals (e.g., cattle, monkeys, poultry, cats, mice, rats, hamsters, pigs, canines), birds, reptiles, amphibians, fish, and insects]. Accordingly, the pharmaceutical composition containing the antibody of the present invention is prepared into an appropriate form depending on the administration route. Specifically, it can be formulated into oral formulations such as tablets, capsules, granules, dispersible powders, and syrups or parenteral formulations such as injections, intravenous drips, liposome compositions, and suppositories. These pharmaceutical preparations can be manufactured by an ordinary method using commonly used excipients, fillers, binding agents, wetting agents, disintegrating agents, surfactants, lubricants, dispersing agents, buffering agents, preservatives, solubilizing agents, antiseptics, flavoring agents, analgesic agents, stabilizers, and the like. Examples of the above-mentioned non-toxic additives to be used include lactose, fructose, glucose, starch, gelatin, magnesium stearate, methylcellulose or its salts, ethanol, citric acid, sodium chloride, and sodium phosphate.

Their form and amount of the administration depend on the selection of the antibody, the subject to be administered, the route of administration, properties of the preparation, conditions of the patient, and physician's judgement. However, the appropriate dose per 1 kg of patient's body weight ranges, for example, from about 0.01 to 30 mg, preferably from about 0.1 to 10 mg. The amount of necessary dosage is expected to vary widely considering that the efficiency is different depending on the route of administration. For example, the dose required for oral administration is expected to be higher than that for intravenous injection. Such variations in the dose level can be adjusted using a standard empirical optimizing procedure well understood in the art.

A substance which interacts with relaxin-3 or a relaxin-3 receptor (preferably SALPR) and inhibits activities of relaxin-3 can be obtained by a screening method of the present invention. An appropriate example of the compound obtained by the above-mentioned screening method is 1,2,5-oxadiazolo[3,4-a]1,2,5-oxadiazolo[3,4-e]1,2,5-oxadiazolo[3,4-i]1,2,5-oxadiazolo[3,4-m][16]annulene (occasionally referred to as "compound 1" hereinafter) described later in an example. Forms of administration of this compound can be referred to those of the above-mentioned medicine containing a compound obtained by a screening method of the present invention.

The term "therapy" as used herein generally means to obtain desired pharmacological effects and/or physiological effects. The effects are preventive in terms of completely or partly preventing diseases and/or symptoms or they are therapeutic in terms of completely or partly curing ill effects caused by diseases and/or symptoms. The term "therapy" as used herein includes therapy of diseases in mammals, particularly humans, and are exemplified by the following therapies:

(a) to prevent the onset of a disease or symptoms in a patient who may have a causative factor for the disease or symptoms but is not diagnosed to have it;
(b) to inhibit disease symptoms, or to prevent or delay their progression; and
(c) to alleviate disease symptoms, that is, to regress a disease or symptoms or reverse the progression of the symptoms.

All of the literature for the prior art cited in this specification are incorporated into the specification by reference.

EXAMPLES

The present invention is illustrated in detail by the following examples, which are not intended to limit the scope of the invention.

Example 1

Preparation of Polynucleotide Encoding SALPR

Isolation of a polynucleotide encoding SALPR was carried out based on the nucleic acid sequence represented by SEQ ID NO: 3 as follows. In SEQ ID NO: 3, 1857 base pairs are shown and the area encoding SALPR is known to be from position 361 to position 1770 (1410 base pairs, 470 amino acid residues) (GenBank Accession No: NM_016568). To isolate a gene by the polymerase chain reaction (PCR), PCR primers represented by SEQ ID NO: 5 and SEQ ID NO: 6 were prepared according to an ordinary method.

Using a human genomic DNA (Roche Diagnostics) as a template, PCR was carried out with a set of PCR primers represented by SEQ ID NO: 5 and SEQ ID NO: 6 using the Expand High Fidelity PCR System (Roche Diagnostics) for 30 repeating cycles (at 98° C. for 1 min, at 57° C. for 1 min, and at 72° C. for 3 min) according to the manufacture's instructions. As a result, an about 1400 base pair DNA fragment was obtained.

This DNA fragment was inserted into pCR2.1 (Invitrogen) and the sequence was confirmed by an ABI prism DNA sequencing kit (Perkin-Elmer Applied Biosystems). As a result, the sequence of 1410 base pairs, which was inserted into pCR2.1-SALPR obtained by the set of the primers consisting of SEQ ID NO: 5 and SEQ ID NO: 6, had a length the same as that from position 361 to position 1770 in SEQ ID NO: 3 but it had one mutation in the sequence. It is evident that this mutation does not influence the amino acid translated from the nucleic acid sequence at this site and thus a polynucleotide encoding SALPR could be obtained.

Example 2

Preparation of Retrovirus Vector Plasmid pBabe Puro (Morgenstern, J. P. and Land, H. Nucleic Acids Res. Vol. 18, 3587-3596 (1990) (SEQ ID NO: 7) was cleaved with SalI and ClaI to remove the SV40 promoter-puro(r) region and was the resulting fragment was blunted with a Klenow fragment. Into the cleaved point the IRES-hyg(r) region which was excised from pIREShyg (Clontech) by cleaving with NsiI and XbaI and blunted with T4 polymerase was inserted to obtain pBabeXIH.

pBabeXIH was cleaved with SspI and BamHI to remove the 5'-LTR-packaging signal. Into the cleaved point the 5'LTR-CMV promoter-packaging signal which was excised from pCLXSN (IMGENEX) by cleaving with SspI and BamHI was inserted to obtain pBabeCLXIH.

Example 3

Preparation of Retrovirus Vector Plasmid for SALPR Gene Transfer

Figure 1:
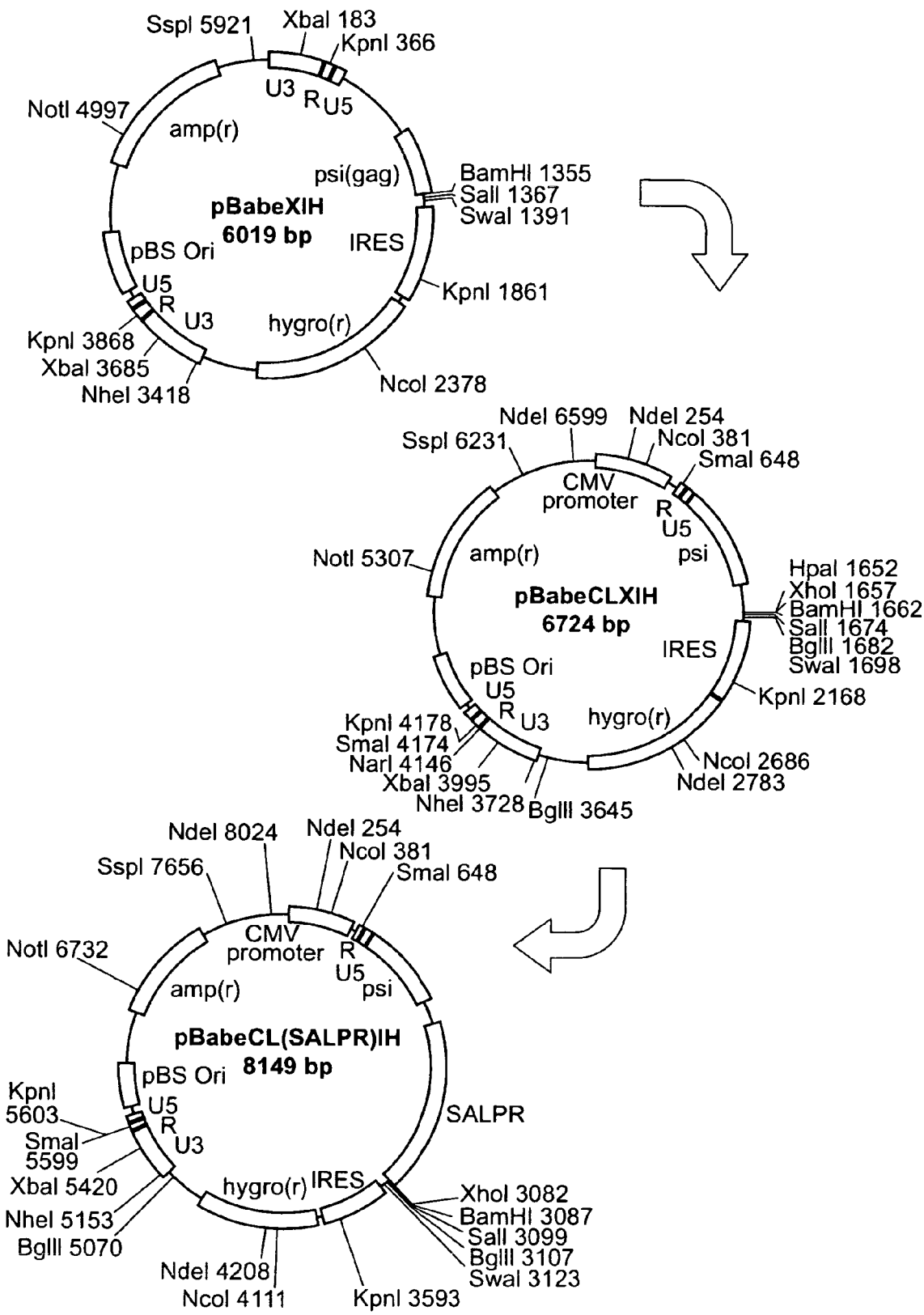
FIG. 1 illustrates the construction of pBabeCL (SALPR) IH.

The retrovirus expression plasmid pBabeCLXIH described in Example 2 above was cleaved with a restriction enzyme HpaI. Into the cleaved point a polynucleotide encoding SALPR, which was excised from pCR2.1-SALPR obtained in Example 1 above by cleaving with EcoRV and blunted with T4 polymerase, was inserted to obtain pBabeCL (SALPR) IH (FIG. 1).

Example 4

Preparation of Retrovirus Vector for SALPR Gene Transfer

293-EBNA cells (Invitrogen) ($2 \times 10^6$) were cultured in a 10-cm collagen-coated dish (IWAKI) using 10 ml of DMEM (Sigma) supplemented with 10% fetal bovine serum (FBS) and 100 units/ml penicillin and 100 µg/ml streptomycin (PS) (referred to as "EBNA medium solution" hereinafter). On the following day, the above-mentioned 293-EBNA cells were transfected using a lipofection reagent TransIT (Panvera) with 3.3 µg each of pV-gp (prepared by cleaving pVPack-GP (Stratagene) with NsiI and XbaI to remove IRES-hisD and blunting with T4 polymerase followed by selfligation of the resulting fragment), pVPack-VSV-G (Stratagene), and the retrovirus vector plasmid for SALPR gene transfer obtained in Example 3. The EBNA medium solution was exchanged 6 to 12 hours later and the incubation was continued at 37° C.

The culture solution was recovered 2 days after transfection and centrifuged at 1,200×g for 10 minutes. The resulting supernatant was filtered with a 0.45 µm filter (Millipore) to obtain an unconcentrated retrovirus vector fraction and further concentration of the viral vector was carried out as follows.

50 Ultra-Clear Tubes (Beckman) for ultra centrifugation were sterilized with 70% ethanol and rinsed with distilled water, into which about 35 ml of the unconcentrated virus vector fraction was poured. The tubes were placed in an SW28 ultracentrifuge rotor (Beckman) and centrifuged at 19,500 rpm for 100 minutes using an XL-90 ultracentrifuge (Beckman). After centrifugation, the resulting supernatant was discarded and the tubes were kept in ice. One hour later, about 100 µl of a concentrated virus vector solution, i.e., the culture solution remaining on the tube wall, was obtained Example 5

Construction of SE302 Cell for Transferring Reporter Genes Containing a Cyclic AMP Responsive Element (1) Construction of Reporter DNA Containing a Cyclic AMP Responsive Element A unit which involves in cAMP responsive transcription was constructed referring to a published paper (Durocher et al. Anal Biochem 2000, 284 (2), 316-26) as follows.

In order to construct a unit containing a cAMP responsive element (CRE), oligo DNAs represented by SEQ ID NO: 8 and SEQ ID NO: 9 for CREx2hb and oligo DNAs represented by SEQ ID NO: 10 and SEQ ID NO: 11 for CREx2bp were constructed according to an ordinary method.

The oligo DNAs of individual combinations were heat treated at 95° C., after which the temperature was gradually lowered to room temperature to form double-stranded DNAs (CREx2hb and CREx2bp). CREx2hb was digested with HindIII and BarrHI and CREx2bp was digested with BamHI and PstI, and at the same time, pBluescriptIISK(+) (Stratagene) was digested with HindIII and PstI. The digested DNAs were subjected to electrophoresis to purify DNAs having restriction enzyme cleavage sites on both ends, after which these 3 DNAs (CREx2hb, CREx2bp, and pBluescriptIISK(+)) were simultaneously ligated and the resulting plasmid sequences were analyzed to construct CRE4/pBluescriptIISK.

Next, in order to obtain DNA containing a VIP (vasoactive intestinal peptide) promoter, PCR primers represented by SEQ ID NO: 12 and SEQ ID NO: 13 were constructed according to an ordinary method.

Figure 2A:
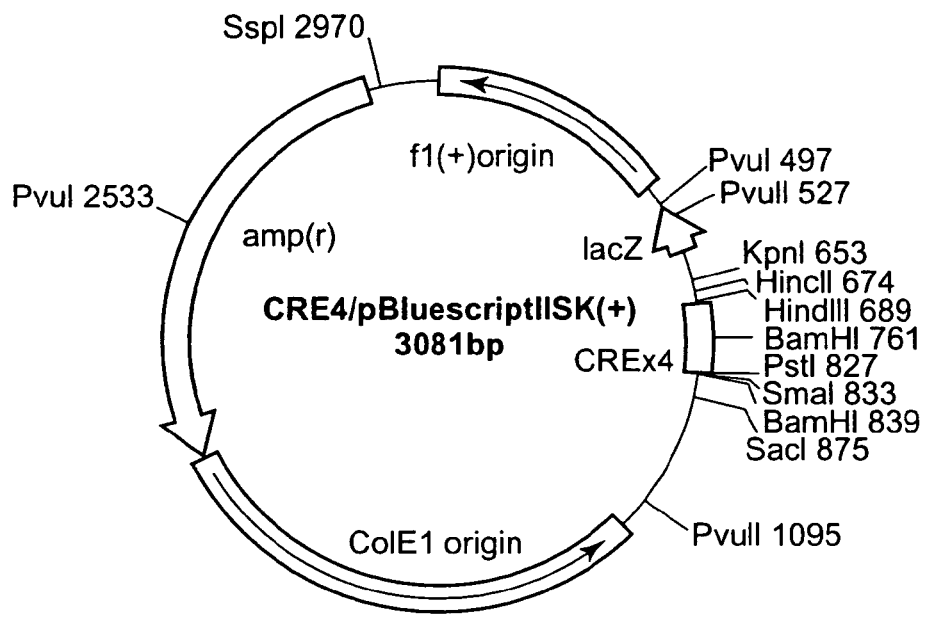
FIG. 2A illustrates the construction of CRE4VIP/pBluescriptIISK(+).
Figure 2A:
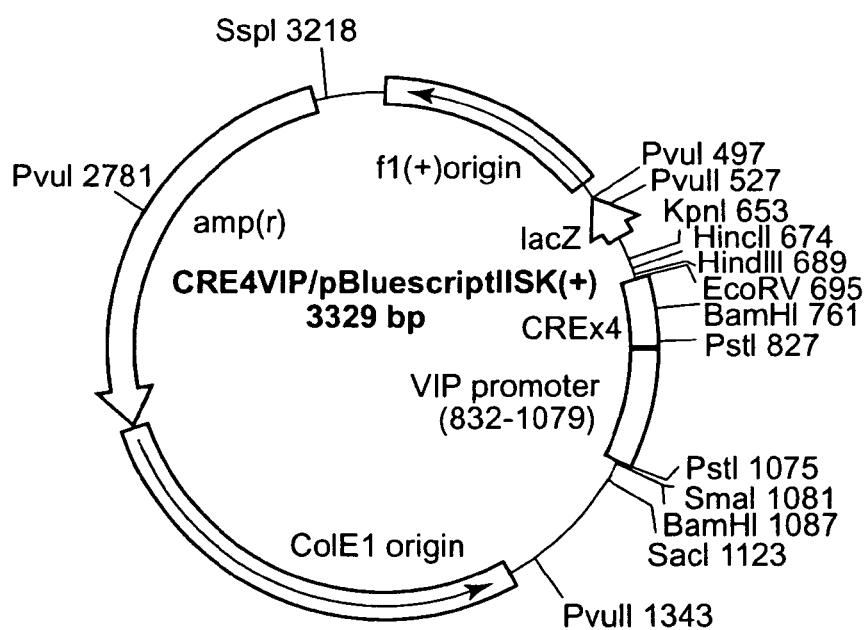

Using a human genomic DNA (Roche Diagnostics) as a template, PCR was carried out with a set of PCR primers represented by SEQ ID NO: 12 and SEQ ID NO: 13 using recombinant Taq polymerase (Takara) for 35 repeating cycles (at 94° C. for 30 sec, at 55° C. for 30 sec, and at 72° C. for 1 min) to obtain a 264 base pair DNA fragment (SEQ ID NO: 14). This 264 base pair DNA was digested with PstI and inserted into the PstI site of CRE4/pBluescriptIISK(+) and the sequence of the resulting plasmid was confirmed to construct CRE4VIP/pBluescriptIISK(+) (FIG. 2A). CRE4VIP/pBluescriptIISK(+) thus obtained was digested with HindIII and SmaI, after which the resulting CRE4VIP promoter fragment was blunted.

Figure 2B:
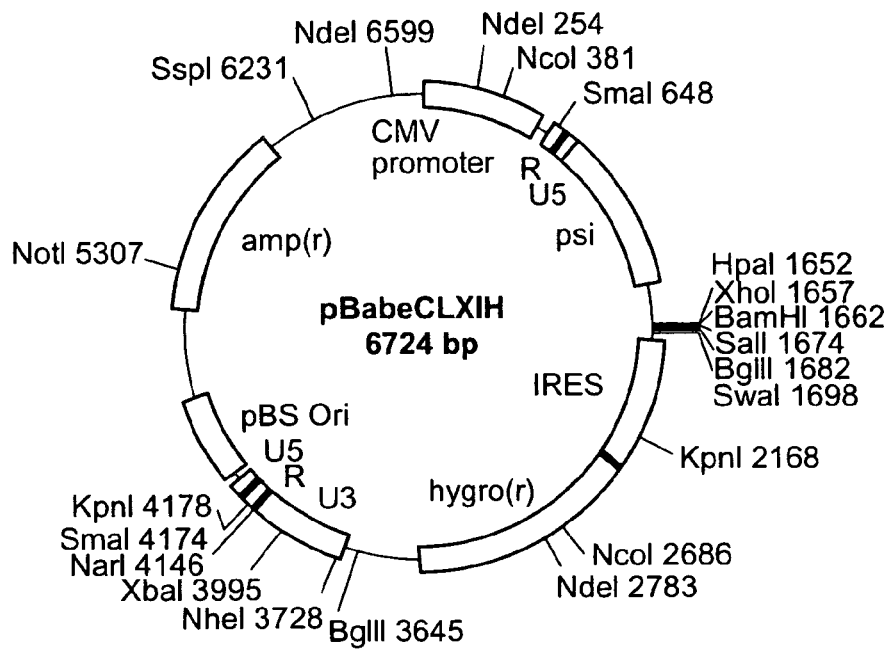
FIG. 2B illustrates the construction of pBabeCLX.
Figure 2B:
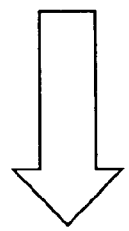
Figure 2B:
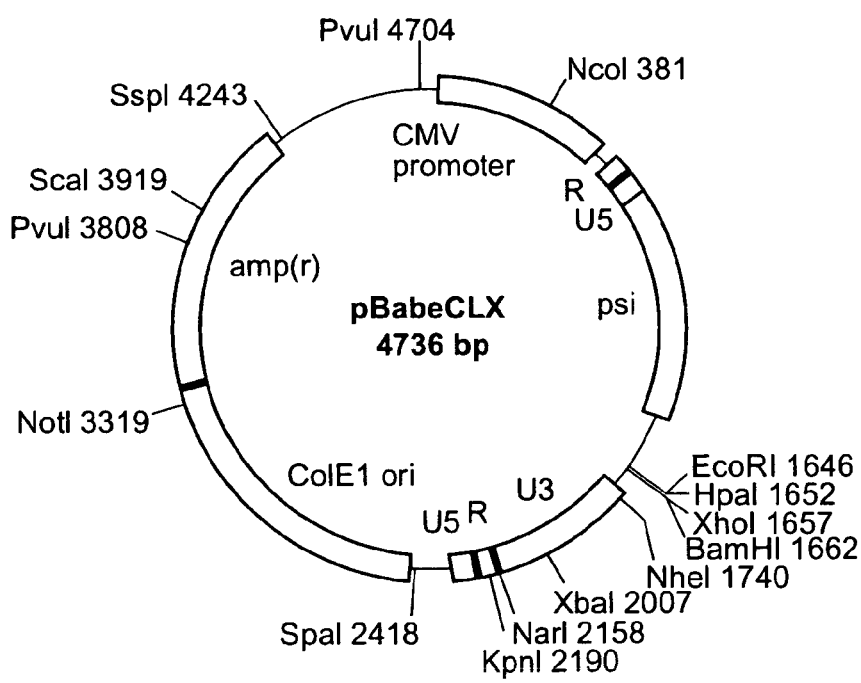
Figure 2C:
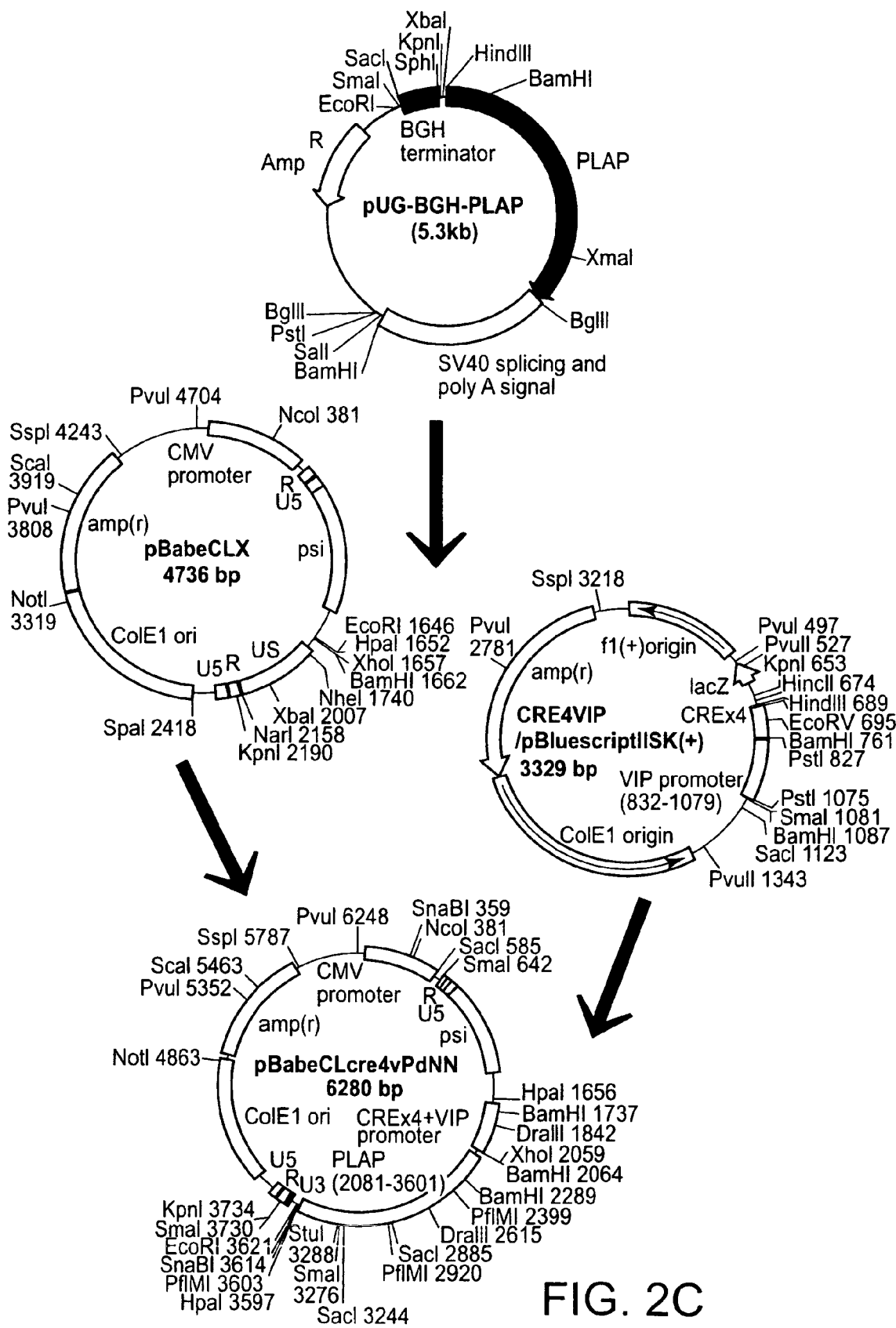
FIG. 2C illustrates the construction of pBabeCLcre4vPdNN.

An IRES-hygro(r) region was removed from the above-mentioned viral expression vector plasmid pBabeCLXIH to construct pBabeCLX (FIG. 2B). A sequence containing CRE and a VIP promoter and a reporter gene, i.e., placenta-derived alkaline phosphatase (PLAP) gene (Goto et al., Molecular Pharmacology, 49, 860-873, 1996) were introduced into a retrovirus vector plasmid for foreign promoter transfer, which was obtained by removing the NheI-NarI region in endogenous retrovirus enhancer activity (LTR) from pBabeCLX, to obtain pBabeCLcre4vPdNN (FIG. 2C).

(2) Establishment of SE302 Cells for Transferring Reporter Genes Containing Cyclic AMP Responsive Element A retrovirus vector was prepared according to the method described in Example 4 using a retrovirus vector plasmid pBabeCLcre4vPdNN in which the PLAP reporter gene is induced by a cyclic AMP responsive element. The retrovirus vector thus prepared was introduced into HEK293 cells and the resulting cells were cloned by the limiting dilution method. A cloned cell exhibiting best reactivity in PLAP induction (hereinafter called "SE302 cell") was used in the following experiments.

Example 6

Preparation of SALPR Expressing Cell by Retrovirus Vector for SALPR Gene Transfer SALPR gene transfer into a cell by the retrovirus vector prepared in Example 4 above was carried out as follows.

SE302 cells ($3 \times 10^3$) constructed in Example 5 above were cultured in a 96-well plate (Asahi Techno Glass) using 100 µl of DMEM (Sigma) supplemented with 10% fetal bovine serum (FBS) and PS (hereinafter called "medium solution"). On the following day, the retrovirus vector prepared in Example 4 was appropriately diluted and a 100-µl portion of the dilution and polybrene (also called as hexadimethrine bromide, Sigma) prepared in the medium solution (at a final concentration of 8 µg/ml) were added to the SE302 cells. On the following day, the medium solution was replaced by 200 µl of medium solution supplemented with 500 µg/ml hygromycin (Invitrogen) and then incubation was continued. The SE302 cells for SALPR gene transfer grown under these conditions (hereinafter called "SALPR-SE302 cells") were appropriately subcultured for experimental use.

Example 7

Suppression by Relaxin-3 of Transcription Activity Increased by Addition of Forskolin in SALPR-SE302 Cells SALPR-SE302 cells constructed in Example 6 above were suspended in a medium for measuring transcription activity (DMEM supplemented with 10% FBS (inactivated at 65° C. for 30 minutes)) and then seeded in a 96-well plate (Beckton Dickinson) at $1 \times 10^4$ cells/well. On the following day, relaxin-3 (Phoenix Pharmaceuticals) or insulin (Invitrogen) diluted with an assay medium (DMEM supplemented with 0.1% bovine serum albumin) in specified concentrations was added, after which forskolin (Calbiochem) was added to make a final concentration of 1 μmol/L. After 1 day incubation, 15 μl each of the cell supernatant was recovered and then transferred to a 96-well plate for chemiluminescence measurement (Sumitomo Bakelite), 60 μl of buffer solution for assay (280 mmol/L $Na_2CO_3$—$NaHCO_3$, 8 mmol/L $MgSO_4$, pH 10) and 70 μl of Lumiphos530 (Lumigen) were added and the reaction was carried out at room temperature for 1 hour, after which chemiluminescence for each well was measured by a fusion plate reader (Perkin Elmer) to assess the transcription activity. The activity in the cell supernatant added with each test sample was represented as a percent by setting the transcription activity in the cell supernatant with forskolin added at 1 μmol/L to be 100% and the activity in the supernatant without the addition of forskolin to be 0% (FIG. 3).

The result showed that relaxin-3 suppressed via SALPR activation the increase in transcription activity by forskolin. Since this increase in transcription activity was not affected by a related peptide, i.e., insulin, the reaction was revealed to be relaxin-3 specific. Namely, it was shown that compounds or substances which affect the activation of SALPR by relaxin-3 can be distinguished by using this experimental system.

Example 8

Screening for Relaxin-3 Antagonistic Substance Using SALPR-SE302 Cells

Using the experimental system shown in Example 7, screening for a compound which antagonizes the activity of relaxin-3 was carried out to find a compound having the antagonistic activity.

SALPR-SE302 cells were suspended in a medium for measuring transcription activity (DMEM-F12 supplemented with 10% FBS (inactivated at 65° C. for 30 minutes)) and then seeded in a 384-well plate (Greiner) at 5000 cells/well. On the following day, a test compound (1,2,5-oxadiazolo[3,4-a]1,2, 5-oxadiazolo[3,4-e]1,2,5-oxadiazolo[3,4-i]1,2,5-oxadiazolo [3,4-m][16]annulene (compound1)) was dissolved in a forskolin (Fermentek) solution and the resulting solution was added to the cell supernatant (the final concentrations: 3 μmol/L forskolin, 20 μg/ml test compound, 0.5% DMSO (dimethyl sulfoxide)). Then, relaxin-3 (Peptide Institute, Inc.) diluted in an assay medium (DMEM-F12 supplemented with 0.1% bovine serum albumin) was added at a final concentration of 3 nmol/L. After 1 day incubation, 5 μl each of the cell supernatant was recovered and then transferred to a 384- well plate for chemiluminescence measurement (Corning), 20 μl of buffer solution for assay and 25 μl of Lumiphos530 were added, and the reaction was carried out at room temperature for 2 hours, after which chemiluminescence for each well was measured by an ARVOsx3 plate reader (Perkin Elmer) to assess the transcription activity. SE302 cells without SALPR expression were treated in the same manner to confirm the specificity of the test substance.

The result showed that relaxin-3 suppressed the increase in transcription activity by forskolin in SALPR-SE302 cells and the test substance compound 1 antagonized suppression of transcription activity by relaxin-3 (FIG. 4A). Further, in SE302 cells without SALPR expression, the compound 1 did not increase the transcription activity (FIG. 4B). Accordingly, it was confirmed that the test substance was a compound which specifically suppressed activation of SALPR by relaxin-3.

Example 9

Feeding-stimulation by Intracerebroventricular Administration of Relaxin-3

(1) Experimental Animals and Pretreatment for Intracerebroventricular Administration Wistar male rats (7 weeks of age; Japan Charles River) were fed feed for experimental animals (MF; Oriental Yeast) to be adapted. The rats (250 to 300 g) received cannulation into the lateral cerebroventricle under anesthesia. Administration experiments were carried out a week or later.

(2) Preparation of Relaxin-3 Solution

Relaxin-3 (60 μg; Phoenix Pharmaceuticals) was dissolved in DMSO and added with an artificial cerebrospinal fluid to make a final concentration of 200 μmol/L. The deposited precipitate was removed by centrifugation and the resulting supernatant was used as a relaxin-3 administration solution. The amount of administration (relaxin-3 concentration in the administration solution) was about 50 pmol/rat when calculated using the standard curve with relaxin-3 in the experimental system shown in Example 7.

(3) Intracerebroventricular Administration of Relaxin-3 Solution

Rats with guide cannula implantation were divided into 2 groups (6 animals per group) and administered with the relaxin-3 administration solution or a vehicle solution (a solution having the same composition as (2) above without relaxin-3) at a rate of 5 μl/2 minutes using an infusion pump.

(4) Measurement of the Amount of Feeding

Immediately after the intracerebroventricular administration of the administration solution, rats were put in a cage where pre-weighed feed was placed and fed ad libitum. The amount of feeding was calculated by measuring the decrease in feed 2 hours later. FIG. 5 shows the amount of average feeding and standard deviation for each group. The result showed that the amount of feeding measured 2 hours after administration was significantly increased in the rats which received about 50 pmol of relaxin-3 as compared to that in the rats which received the control vehicle solution (t-test, p<0.01). Accordingly, it was revealed that relaxin-3 stimulated feeding behavior.

Example 10

Increase in Blood Leptin Concentration Upon Single Intracerebroventricular Administration of Relaxin-3 Measurement of Blood Leptin Concentration The above-mentioned rats were anesthetized with Nembutal after the feeding measurement (about 3 hours after administration) and the blood was taken from the abdominal aorta. The blood taken was centrifuged at 1,750×g for 15 minutes and the resulting supernatant was stored at −80° C. Later, the amount of leptin in the supernatant was quantitatively determined by a rat leptin quantification ELISA kit (Amersham Bioscience).

The result revealed that the blood leptin concentration was significantly increased in the rats in the single relaxin-3 administration group as compared to that in the control vehicle administration group (t-test, $p<0.05$; FIG. 6).

Example 11

Stimulation of Body Weight Gain and Fattening by Chronic Administration of Relaxin-3

(1) Preparation of Relaxin-3 Solution

A relaxin-3 solution was prepared by dissolving relaxin-3 (Peptide Institute, Inc.) in physiological saline at a concentration of 100 μmol/L. A vehicle solution (physiological saline) or the relaxin-3 solution was poured into an osmotic pump (Alzet osmotic pump model 1002 (DURECT); delivering 6 μl/day), a tube and a cannula for administration, after which they were connected together.

(2) Experimental Animals and Treatment for Intracerebroventricular Administration Wistar male rats (6 weeks of age; Japan Charles River) were fed feed for experimental animals (MF; Oriental Yeast) and adapted to individual cages for 4 days. Under anesthesia, a guide cannula was inserted into the lateral cerebroventricle of these rats (250-270 g) and an osmotic pump was implanted under the skin.

(3) Measurements of Body Weight Increase and the Amount of Feeding

The rats had free access to feed and their body weight and feeding were measured every morning. Body weight increase from the day of operation (day 0) is shown in FIG. 7. Further, the decrease in the amount of feed per day is shown as the amount of feeding (FIG. 8).

A significant increase in body weight was confirmed from day 1 after operation in the rats in the relaxin-3 administration group. Further, a significant increase in the amount of feeding was also observed from day 1 in the relaxin-3 administration group (t-test; ** $p<0.01$, * $p<0.05$).

(4) Measurement of Fat Weight and Quantitative Determination of Blood Leptin and Blood Insulin Levels After measuring body weight and the amount of feed on the last day of the experiment (day 14), the rats were anesthetized with Nembutal, epididymal fat was taken and the total fat weight was measured (FIG. 9). Further, the blood was taken from the abdominal aorta. The blood was centrifuged at 1,750×g for 15 minutes and the resulting supernatant was stored at −80° C. Later, the amount of leptin in the supernatant was quantitatively determined by a rat leptin measuring kit (L) (IBL) (FIG. 10A). Further, the amount of insulin in the supernatant was quantitatively determined by an ultra sensitive rat insulin measuring kit (Morinaga Institute of Biological Science) (FIG. 10B).

The result showed that the amount of epididymal fat was significantly increased in the rats in the relaxin-3 chronic administration group as compared to the rats in the control vehicle administration group. Further, it was revealed that the leptin and insulin concentrations in blood were also significantly increased in the rats in the relaxin-3 chronic administration group (t-test; ** $p<0.01$, * $p<0.05$). Accordingly, it was revealed that the relaxin-3 administration stimulated fattening activity associated with fat accumulation and at the same time increased the insulin level.

Example 12

Effect of Relaxin-3 Chronic Administration on Body Weight Gain and Locomotor Activity (1) Preparation of Relaxin-3 Solution A relaxin-3 solution was prepared by dissolving relaxin-3 (Peptide Institute, Inc.) in physiological saline at a concentration of 100 μmol/L. A vehicle solution (physiological saline) or the relaxin-3 solution was poured into an osmotic pump (Alzet osmotic pump model 1002 (DURECT), delivering at 6 μ/day), a tube and a cannula for administration, after which they were connected together.

(2) Experimental Animals and Treatment for Intracerebroventricular Administration Wistar male rats (5 weeks of age; Japan Charles River) were fed feed for experimental animals (MF; Oriental Yeast) and adapted to individual cages for 5 days. Under anesthesia, a guide cannula was inserted into the lateral cerebroventricle of these rats (170-200 g) and an osmotic pump was implanted under the skin. The operation date was set to be day 0. The rats had free access to feed and water and the body weight was measured every morning, except on days for locomotor activity measurement (FIG. 11).

A significant increase in body weight was confirmed from day 1 after administration in the rats in the relaxin-3 administration group similarly to Example 11 above (t-test; ** $p<0.01$, * $p<0.05$).

(3) Measurement of Spontaneous Locomotor Activity

Spontaneous locomotor activity was measured using a Versamax system (Accuscan) in the light phase and dark phase on days when significant difference in body weight increasing activity in the rats receiving relaxin-3 administration was recognized.

Rats in the light phase (on days 2 and 7 after the start of administration) and rats in dark phase (on days 3 and 8 after the start of administration) were transferred from individual cage room to a laboratory for adaptation at least 1 hour prior to the experiment, after which the rats were introduced into a Versamax cage and locomotor activity was recorded starting immediately for 90 minutes. The total locomotor activity for 90 minutes is shown in FIG. 12.

No significant change in locomotor activity was observed in rats in any group on any day. Namely, it was revealed that the body weight increasing activity of relaxin-3 was not due to the change in spontaneous locomotor activity.

INDUSTRIAL APPLICABILITY

According to the present invention, there are provided a polypeptide having useful effects in stimulating feeding, increasing body weight, and fattening; a therapeutic agent containing said polypeptide; a method of screening for a compound, a substance, or a salt thereof which activates or suppresses a receptor of said polypeptide; a kit for said screening; and an agent which comprises a substance which inhibits expression of said polypeptide, such as a feeding-suppressing agent, a therapeutic agent for the treatment of obesity, and a therapeutic agent for the treatment of diabetes.

The invention claimed is:

1. A method of stimulating feeding, comprising administering an effective amount of relaxin-3, or a salt thereof, to a mammal in need thereof.

2. A method of increasing body weight, comprising administering an effective amount of relaxin-3, or a salt thereof, to a mammal in need thereof.

3. A method of increasing fat weight, comprising administering an effective amount of relaxin-3, or a salt thereof, to a mammal in need thereof.

4. A method of recovering feeding and/or body weight gain in a patient having a disease involving reduced feeding and/or weight loss, comprising administering an effective amount of relaxin-3, or a salt thereof, to a patient in need thereof.

5. A method of treating anorexia or cachexia, comprising administering an effective amount of relaxin-3, or a salt thereof, to a mammal in need thereof.

* * * * *

SEQUENCE LISTING

```
<160> NUMBER OF SEQ ID NOS: 14

<210> SEQ ID NO 1
<211> LENGTH: 429
<212> TYPE: DNA
<213> ORGANISM: Homo sapiens
<220> FEATURE:
<221> NAME/KEY: CDS
<222> LOCATION: (1)..(429)
<223> OTHER INFORMATION:

<400> SEQUENCE: 1 atg gcc agg tac atg ctg ctg ctc ctg gcg gta tgg gtg ctg acc         48
Met Ala Arg Tyr Met Leu Leu Leu Leu Ala Val Trp Val Leu Thr
1               5                   10                  15 ggg gag ctg tgg ccg gga gct gag gcc cgg gca gcg cct tac ggg gtc     96
Gly Glu Leu Trp Pro Gly Ala Glu Ala Arg Ala Ala Pro Tyr Gly Val
            20                  25                  30 agg ctt tgc ggc cga gaa ttc atc cga gca gtc atc ttc acc tgc ggg    144
Arg Leu Cys Gly Arg Glu Phe Ile Arg Ala Val Ile Phe Thr Cys Gly
        35                  40                  45 ggc tcc cgg tgg aga cga tca gac atc ctg gcc cac gag gct atg gga    192
Gly Ser Arg Trp Arg Arg Ser Asp Ile Leu Ala His Glu Ala Met Gly
    50                  55                  60 gat acc ttc ccg gat gca gat gct gat gaa gac agt ctg gca ggc gag    240
Asp Thr Phe Pro Asp Ala Asp Ala Asp Glu Asp Ser Leu Ala Gly Glu
65                  70                  75                  80 ctg gat gag gcc atg ggg tcc agc gag tgg ctg gcc ctg acc aag tca    288
Leu Asp Glu Ala Met Gly Ser Ser Glu Trp Leu Ala Leu Thr Lys Ser
                85                  90                  95 ccc cag gcc ttt tac agg ggg cga ccc agc tgg caa gga acc cct ggg    336
Pro Gln Ala Phe Tyr Arg Gly Arg Pro Ser Trp Gln Gly Thr Pro Gly
            100                 105                 110 gtt ctt cgg ggc agc cga gat gtc ctg gct ggc ctt tcc agc agc tgc    384
Val Leu Arg Gly Ser Arg Asp Val Leu Ala Gly Leu Ser Ser Ser Cys
        115                 120                 125 tgc aag tgg ggg tgt agc aaa agt gaa atc agt agc ctt tgc tag        429
Cys Lys Trp Gly Cys Ser Lys Ser Glu Ile Ser Ser Leu Cys
    130                 135                 140

<210> SEQ ID NO 2
<211> LENGTH: 142
<212> TYPE: PRT
<213> ORGANISM: Homo sapiens

<400> SEQUENCE: 2

Met Ala Arg Tyr Met Leu Leu Leu Leu Ala Val Trp Val Leu Thr
1               5                   10                  15

Gly Glu Leu Trp Pro Gly Ala Glu Ala Arg Ala Ala Pro Tyr Gly Val
            20                  25                  30

Arg Leu Cys Gly Arg Glu Phe Ile Arg Ala Val Ile Phe Thr Cys Gly
        35                  40                  45

Gly Ser Arg Trp Arg Arg Ser Asp Ile Leu Ala His Glu Ala Met Gly
    50                  55                  60

Asp Thr Phe Pro Asp Ala Asp Ala Asp Glu Asp Ser Leu Ala Gly Glu
```

```
                65                  70                  75                  80
Leu Asp Glu Ala Met Gly Ser Ser Glu Trp Leu Ala Leu Thr Lys Ser
                        85                  90                  95
Pro Gln Ala Phe Tyr Arg Gly Arg Pro Ser Trp Gln Gly Thr Pro Gly
                100                 105                 110
Val Leu Arg Gly Ser Arg Asp Val Leu Ala Gly Leu Ser Ser Ser Cys
            115                 120                 125
Cys Lys Trp Gly Cys Ser Lys Ser Glu Ile Ser Ser Leu Cys
        130                 135                 140

<210> SEQ ID NO 3
<211> LENGTH: 1857
<212> TYPE: DNA
<213> ORGANISM: Homo sapiens
<220> FEATURE:
<221> NAME/KEY: CDS
<222> LOCATION: (361)..(1770)
<223> OTHER INFORMATION:

<400> SEQUENCE: 3
gatttgggga gttatgcgcc agtgccccag tgaccgcggg acacggagag gggaagtctg     60
cgttgtacat aaggacctag ggactccgag cttggcctga gaacccttgg acgccgagtg    120
cttgccttac gggctgcact cctcaactct gctccaaagc agccgctgag ctcaactcct    180
gcgtccaggg cgttcgctgc gcgccaggac gcgcttagta cccagttcct gggctctctc    240
ttcagtagct gctttgaaag ctcccacgca cgtcccgcag gctagcctgg caacaaaact    300
ggggtaaacc gtgttatctt aggtcttgtc ccccagaaca tgacctagag gtacctgcgc    360
atg cag atg gcc gat gca gcc acg ata gcc acc atg aat aag gca gca     408
Met Gln Met Ala Asp Ala Ala Thr Ile Ala Thr Met Asn Lys Ala Ala
1               5                   10                  15
ggc ggg gac aag cta gca gaa ctc ttc agt ctg gtc ccg gac ctt ctg      456
Gly Gly Asp Lys Leu Ala Glu Leu Phe Ser Leu Val Pro Asp Leu Leu
                20                  25                  30
gag gcg gcc aac acg agt ggt aac gcg tcg ctg cag ctt ccg gac ttg      504
Glu Ala Ala Asn Thr Ser Gly Asn Ala Ser Leu Gln Leu Pro Asp Leu
            35                  40                  45
tgg tgg gag ctg ggg ctg gag ttg ccg gac ggc gcg ccg cca gga cat      552
Trp Trp Glu Leu Gly Leu Glu Leu Pro Asp Gly Ala Pro Pro Gly His
        50                  55                  60
ccc ccg ggc agc ggc ggg gca gag agc gcg gac aca gag gcc cgg gtg      600
Pro Pro Gly Ser Gly Gly Ala Glu Ser Ala Asp Thr Glu Ala Arg Val
65                  70                  75                  80
cgg att ctc atc agc gtg gtg tac tgg gtg gtg tgc gcc ctg ggg ttg      648
Arg Ile Leu Ile Ser Val Val Tyr Trp Val Val Cys Ala Leu Gly Leu
                85                  90                  95
gcg ggc aac ctg ctg gtt ctc tac ctg atg aag agc atg cag ggc tgg      696
Ala Gly Asn Leu Leu Val Leu Tyr Leu Met Lys Ser Met Gln Gly Trp
                100                 105                 110
cgc aag tcc tct atc aac ctc ttc gtc acc aac ctg gcg ctg acg gac      744
Arg Lys Ser Ser Ile Asn Leu Phe Val Thr Asn Leu Ala Leu Thr Asp
            115                 120                 125
ttt cag ttt gtg ctc acc ctg ccc ttc tgg gcg gtg gag aac gct ctt      792
Phe Gln Phe Val Leu Thr Leu Pro Phe Trp Ala Val Glu Asn Ala Leu
        130                 135                 140
gac ttc aaa tgg ccc ttc ggc aag gcc atg tgt aag atc gtg tcc atg      840
Asp Phe Lys Trp Pro Phe Gly Lys Ala Met Cys Lys Ile Val Ser Met
145                 150                 155                 160
gtg acg tcc atg aac atg tac gcc agc gtg ttc ttc ctc act gcc atg      888
Val Thr Ser Met Asn Met Tyr Ala Ser Val Phe Phe Leu Thr Ala Met
                165                 170                 175
agt gtg acg cgc tac cat tcg gtg gcc tcg gct ctg aag agc cac cgg      936
Ser Val Thr Arg Tyr His Ser Val Ala Ser Ala Leu Lys Ser His Arg
                180                 185                 190
acc cga gga cac ggc cgg ggc gac tgc tgc ggc cgg agc ctg ggg gac      984
Thr Arg Gly His Gly Arg Gly Asp Cys Cys Gly Arg Ser Leu Gly Asp
            195                 200                 205
agc tgc tgc ttc tcg gcc aag gcg ctg tgt gtg tgg atc tgg gct ttg     1032
Ser Cys Cys Phe Ser Ala Lys Ala Leu Cys Val Trp Ile Trp Ala Leu
        210                 215                 220
gcc gcg ctg gcc tcg ctg ccc agt gcc att ttc tcc acc acg gtc aag     1080
Ala Ala Leu Ala Ser Leu Pro Ser Ala Ile Phe Ser Thr Thr Val Lys
225                 230                 235                 240
gtg atg ggc gag gag ctg tgc ctg gtg cgt ttc ccg gac aag ttg ctg     1128
Val Met Gly Glu Glu Leu Cys Leu Val Arg Phe Pro Asp Lys Leu Leu
```

-continued

```
                  245                 250                 255
ggc cgc gac agg cag ttc tgg ctg ggc ctc tac cac tcg cag aag gtg    1176
Gly Arg Asp Arg Gln Phe Trp Leu Gly Leu Tyr His Ser Gln Lys Val
            260                 265                 270
ctg ttg ggc ttc gtg ctg ccg ctg ggc atc att atc ttg tgc tac ctg    1224
Leu Leu Gly Phe Val Leu Pro Leu Gly Ile Ile Ile Leu Cys Tyr Leu
        275                 280                 285
ctg ctg gtg cgc ttc atc gcc gac cgc gcg gcg ggg acc aaa gga        1272
Leu Leu Val Arg Phe Ile Ala Asp Arg Ala Ala Gly Thr Lys Gly
    290                 295                 300
ggg gcc gcg gta gcc gga gga cgc ccg acc gga gcc agc gcc cgg aga    1320
Gly Ala Ala Val Ala Gly Gly Arg Pro Thr Gly Ala Ser Ala Arg Arg
305                 310                 315                 320
ctg tcg aag gtc acc aaa tca gtg acc atc gtt gtc ctg tcc ttc ttc    1368
Leu Ser Lys Val Thr Lys Ser Val Thr Ile Val Val Leu Ser Phe Phe
                325                 330                 335
ctg tgt tgg ctg ccc aac cag gcg ctc acc acc tgg agc atc ctc atc    1416
Leu Cys Trp Leu Pro Asn Gln Ala Leu Thr Thr Trp Ser Ile Leu Ile
            340                 345                 350
aag ttc aac gcg gtg ccc ttc agc cag gag tat ctg tgc cag gta        1464
Lys Phe Asn Ala Val Pro Phe Ser Gln Glu Tyr Leu Cys Gln Val
        355                 360                 365
tac gcg ttc cct gtg agc gtg tgc cta gcg cac tcc aac agc tgc ctc    1512
Tyr Ala Phe Pro Val Ser Val Cys Leu Ala His Ser Asn Ser Cys Leu
    370                 375                 380
aac ccc gtc ctc tac tgc ctc gtg cgc cgc gag ttc cgc aag gcg ctc    1560
Asn Pro Val Leu Tyr Cys Leu Val Arg Arg Glu Phe Arg Lys Ala Leu
385                 390                 395                 400
aag agc ctg ctg tgg cgc atc gcg tct cct tcg atc acc agc atg cgc    1608
Lys Ser Leu Leu Trp Arg Ile Ala Ser Pro Ser Ile Thr Ser Met Arg
                405                 410                 415
ccc ttc acc gcc act acc aag ccg gag cac gag gat cag ggg ctg cag    1656
Pro Phe Thr Ala Thr Thr Lys Pro Glu His Glu Asp Gln Gly Leu Gln
            420                 425                 430
gcc ccg gcg ccg ccc cac gcg gcc gcg gag ccg gac ctg ctc tac tac    1704
Ala Pro Ala Pro Pro His Ala Ala Ala Glu Pro Asp Leu Leu Tyr Tyr
        435                 440                 445
cca cct ggc gtc gtg gtc tac agc ggg ggg cgc tac gac ctg ctg ccc    1752
Pro Pro Gly Val Val Val Tyr Ser Gly Gly Arg Tyr Asp Leu Leu Pro
    450                 455                 460
agc agc tct gcc tac tga cgcaggcctc aggcccaggg cgcgccgtcg           1800
Ser Ser Ser Ala Tyr
465
gggcaaggtg gccttccccg ggcggtaaag aggtgaaagg atgaaggagg gctgggg     1857

<210> SEQ ID NO 4
<211> LENGTH: 469
<212> TYPE: PRT
<213> ORGANISM: Homo sapiens

<400> SEQUENCE: 4

Met Gln Met Ala Asp Ala Ala Thr Ile Ala Thr Met Asn Lys Ala Ala
1               5                   10                  15

Gly Gly Asp Lys Leu Ala Glu Leu Phe Ser Leu Val Pro Asp Leu Leu
            20                  25                  30

Glu Ala Ala Asn Thr Ser Gly Asn Ala Ser Leu Gln Leu Pro Asp Leu
        35                  40                  45

Trp Trp Glu Leu Gly Leu Glu Leu Pro Asp Gly Ala Pro Pro Gly His
    50                  55                  60

Pro Pro Gly Ser Gly Gly Ala Glu Ser Ala Asp Thr Glu Ala Arg Val
65                  70                  75                  80

Arg Ile Leu Ile Ser Val Val Tyr Trp Val Cys Ala Leu Gly Leu
                85                  90                  95

Ala Gly Asn Leu Leu Val Leu Tyr Leu Met Lys Ser Met Gln Gly Trp
            100                 105                 110

Arg Lys Ser Ser Ile Asn Leu Phe Val Thr Asn Leu Ala Leu Thr Asp
        115                 120                 125

Phe Gln Phe Val Leu Thr Leu Pro Phe Trp Ala Val Glu Asn Ala Leu
    130                 135                 140
```

```
Asp Phe Lys Trp Pro Phe Gly Lys Ala Met Cys Lys Ile Val Ser Met
145                 150                 155                 160

Val Thr Ser Met Asn Met Tyr Ala Ser Val Phe Phe Leu Thr Ala Met
            165                 170                 175

Ser Val Thr Arg Tyr His Ser Val Ala Ser Ala Leu Lys Ser His Arg
        180                 185                 190

Thr Arg Gly His Gly Arg Gly Asp Cys Cys Gly Arg Ser Leu Gly Asp
            195                 200                 205

Ser Cys Cys Phe Ser Ala Lys Ala Leu Cys Val Trp Ile Trp Ala Leu
    210                 215                 220

Ala Ala Leu Ala Ser Leu Pro Ser Ala Ile Phe Ser Thr Thr Val Lys
225                 230                 235                 240

Val Met Gly Glu Glu Leu Cys Leu Val Arg Phe Pro Asp Lys Leu Leu
                245                 250                 255

Gly Arg Asp Arg Gln Phe Trp Leu Gly Leu Tyr His Ser Gln Lys Val
            260                 265                 270

Leu Leu Gly Phe Val Leu Pro Leu Gly Ile Ile Ile Leu Cys Tyr Leu
        275                 280                 285

Leu Leu Val Arg Phe Ile Ala Asp Arg Arg Ala Ala Gly Thr Lys Gly
        290                 295                 300

Gly Ala Val Ala Gly Gly Arg Pro Thr Gly Ala Ser Ala Arg Arg
305                 310                 315                 320

Leu Ser Lys Val Thr Lys Ser Val Thr Ile Val Val Leu Ser Phe Phe
                325                 330                 335

Leu Cys Trp Leu Pro Asn Gln Ala Leu Thr Thr Trp Ser Ile Leu Ile
            340                 345                 350

Lys Phe Asn Ala Val Pro Phe Ser Gln Glu Tyr Phe Leu Cys Gln Val
            355                 360                 365

Tyr Ala Phe Pro Val Ser Val Cys Leu Ala His Ser Asn Ser Cys Leu
        370                 375                 380

Asn Pro Val Leu Tyr Cys Leu Val Arg Arg Glu Phe Arg Lys Ala Leu
385                 390                 395                 400

Lys Ser Leu Leu Trp Arg Ile Ala Ser Pro Ser Ile Thr Ser Met Arg
                405                 410                 415

Pro Phe Thr Ala Thr Thr Lys Pro Glu His Glu Asp Gln Gly Leu Gln
            420                 425                 430

Ala Pro Ala Pro Pro His Ala Ala Ala Glu Pro Asp Leu Leu Tyr Tyr
        435                 440                 445

Pro Pro Gly Val Val Val Tyr Ser Gly Gly Arg Tyr Asp Leu Leu Pro
    450                 455                 460

Ser Ser Ser Ala Tyr
465

<210> SEQ ID NO 5
<211> LENGTH: 38
<212> TYPE: DNA
<213> ORGANISM: Artificial Sequence
<220> FEATURE:
<223> OTHER INFORMATION: A sense primer

<400> SEQUENCE: 5
gatatcgccg ccaccatgca gatggccgat gcagccac                          38

<210> SEQ ID NO 6
<211> LENGTH: 28
```

```
<212> TYPE: DNA
<213> ORGANISM: Artificial Sequence
<220> FEATURE:
<223> OTHER INFORMATION: An antisense primer

<400> SEQUENCE: 6
gatatctcag taggcagagc tgctgggc                                          28

<210> SEQ ID NO 7
<211> LENGTH: 5020
<212> TYPE: DNA
<213> ORGANISM: Plasmid

<400> SEQUENCE: 7
ctgcagcctg aatatgggcc aaacaggata tctgtggtaa gcagttcctg ccccggctca      60
gggccaagaa cagatggaac agctgaatat gggccaaaca ggatatctgt ggtaagcagt     120
tcctgccccg gctcagggcc aagaacagat ggtccccaga tgcggtccag ccctcagcag     180
tttctagaga accatcagat gtttccaggg tgccccaagg acctgaaatg accctgtgcc     240
ttatttgaac taaccaatca gttcgcttct cgcttctgtt cgcgcgcttc tgctccccga     300
gctcaataaa agagcccaca cccctcact cggggcgcca gtcctccgat tgactgagtc      360
gcccgggtac ccgtgtatcc aataaaccct cttgcagttg catccgactt gtggtctcgc     420
tgttccttgg gagggtctcc tctgagtgat tgactacccg tcagcggggg tctttcattt     480
gggggctcgt ccgggatcgg gagacccctg cccaggggacc accgaccac caccgggagg    540
taagctggcc agcaacttat ctgtgtctgt ccgattgtct agtgtctatg actgatttta     600
tgcgcctgcg tcggtactag ttagctaact agctctgtat ctggcggacc cgtggtggaa     660
ctgacgagtt ctgaacaccc ggccgcaacc ctggagacg tcccagggac tttgggggcc      720
gttttttgtgg cccgacctga ggaagggagt cgatgtggaa tccgaccccg tcaggatatg    780
tggttctggt aggagacgag aacctaaaac agttcccgcc tccgtctgaa ttttttgcttt    840
cggtttggaa ccgaagccgc gcgtcttgtc tgctgcagca tcgttctgtg ttgtctctgt     900
ctgactgtgt ttctgtatttt gtctgaaaat tagggccaga ctgttaccac tcccttaagt    960
ttgaccttag atcactggaa agatgtcgag cggctcgctc acaaccagtc ggtagatgtc    1020
aagaagagac gttgggttac cttctgctct gcagaatggc caacctttaa cgtcggatgg    1080
ccgcgagacg gcacctttaa ccgagacctc atcacccagg ttaagatcaa ggtcttttca    1140
cctggcccgc atggacaccc agaccaggtc cctacatcg tgacctggga agccttggct     1200
tttgaccccc ctccctgggt caagcccttt gtacaccta gcctccgcc tcctcttctt      1260
ccatccgcgc cgtctctccc ccttgaacct cctctttcga cccgcctca atcctccctt     1320
tatccagccc tcactccttc tctaggcgcc ggccggatcc cagtgtggtg gtacgtagga    1380
attgccagc acagtggtcg acctgtggaa tgtgtgtcag ttagggtgtg gaaagtcccc      1440
aggctcccca gcaggcagaa gtatgcaaag catgcatctc aattagtcag caaccaggtg    1500
tggaaagtcc ccaggctccc cagcaggcag aagtatgcaa agcatgcatc tcaattagtc    1560
agcaaccata gtcccgcccc taactccgcc catcccgccc taactccgc ccagttccgc      1620
ccattctccg cccatggct gactaatttt ttttatttat gcagaggccg aggccgcctc     1680
ggcctctgag ctattccaga agtagtgagg aggctttttt ggaggcctag gcttttgcaa    1740
acgctgcttg aggctgaagg tgcgttgctg gcgttttttcc ataggctccg ccccctgac    1800
gagcatcaca aaaatcgacg ctcaagtcag aggtggcgaa acccgacagg actataaaga    1860
```

```
taccaggcgt tccccctgg aagctccctc gtgcgctctc ctgttccgac cctgccgctt    1920
accggatacc tgtccgcctt tctcccttcg ggaagcgtgg cgctttctca tagctcacgc    1980
tgtaggtatc tcagttcggt gtaggtcgtt cgctccaagc tgggctgtgt gcacgaaccc    2040
cccgttcagc ccgaccgctg cgccttatcc ggtaactatc gtcttgagtc caacccggta    2100
agacacgact tatcgccact ggcagcagcc actggtaaca ggattagcag agcgaggtat    2160
gtaggcggtg ctacagagtt cttgaagtgg tggcctaact acggctacac tagaaggaca    2220
gtatttggta tctgcgctct gctgaagcca gttaccttcg gaaaaagagt tggtagctct    2280
tgatccggca aacaaccac cgctggtagc ggtggttttt tgtttgcaa gcagcagatt     2340
acgatcgata aaataaaaga ttttatttag tctccagaaa aggggggaa tgaaagaccc     2400
cacctgtagg tttggcaagc tagcttaagt aacgccattt tgcaaggcat ggaaaaatac    2460
ataactgaga atagagaagt tcagatcaag gtcaggaaca gatggaacag ctgaatatgg    2520
gccaaacagg atatctgtgg taagcagttc ctgccccgc tcagggccaa gaacagatgg     2580
aacagctgaa tatgggccaa acaggatatc tgtggtaagc agttcctgcc ccggctcagg    2640
gccaagaaca tggtcccc agatgcggtc cagccctcag cagtttctag agaaccatca      2700
gatgtttcca gggtgcccca aggacctgaa atgaccctgt gccttatttg aactaaccaa    2760
tcagttcgct ctcgcttct gttcgcgcgc ttctgctccc cgagctcaat aaaagagccc     2820
acaacccctc actcggggcg ccagtcctcc gattgactga gtcgcccggg tacccgtgta    2880
tccaataaac cctcttgcag ttgcatccga cttgtggtct cgctgttcct tgggagggtc    2940
tcctctgagt gattgactac ccgtcagcgg gggtctttca catgcagcat gtatcaaaat    3000
taatttggtt tttttctta agtatttaca ttaaatggcc atagttgcat taatgaatcg     3060
gccaacgcgc ggggagaggc ggtttgcgta ttgggcgctc ttccgcttcc tcgctcactg    3120
actcgctgcg ctcggtcgtt cggctgcggc gagcggtatc agctcactca aaggcggtaa    3180
tacggttatc cacagaatca ggggataacg caggaaagaa catgtgagca aaaggccagc    3240
aaaaggccag gaaccgtaaa aaggccgcgt tgctggcgtt tttccatagg ctccgccccc    3300
ctgacgagca tcacaaaaat cgacgctcaa gtcagaggtg gcgaaacccg acaggactat    3360
aaagatacca ggcgtttccc cctggaagct ccctcgtgcg ctctcctgtt ccgaccctgc    3420
cgcttaccgg atacctgtcc gcctttctcc cttcgggaag cgtggcgctt tctcatagct    3480
cacgctgtag gtatctcagt tcggtgtagg tcgttcgctc caagctgggc tgtgtgcacg    3540
aaccccccgt tcagcccgac cgctgcgcct tatccggtaa ctatcgtctt gagtccaacc    3600
cggtaagaca cgacttatcg ccactggcag cagccactgg taacaggatt agcagagcga    3660
ggtatgtagg cggtgctaca gagttcttga agtggtggcc taactacggc tacactagaa    3720
ggacagtatt tggtatctgc gctctgctga gccagttac cttcggaaaa agagttggta    3780
gctcttgatc cggcaaacaa ccaccgctg gtagcggtgg ttttttgtt tgcaagcagc      3840
agattacgcg cagaaaaaa ggatctcaag aagatccttt gatcttttct acggggtctg     3900
acgctcagtg gaacgaaaac tcacgttaag ggattttggt catgagatta tcaaaaagga    3960
tcttcaccta gatcctttta aattaaaaat gaagtttgcg gccgcaaatc aatctaaagt    4020
atatatgagt aaacttggtc tgacagttac caatgcttaa tcagtgaggc acctatctca    4080
gcgatctgtc tatttcgttc atccatagtt gcctgactcc ccgtcgtgta gataactacg    4140
atacgggagg gcttaccatc tggccccagt gctgcaatga taccgcgaga cccacgctca    4200
ccggctccag atttatcagc aataaaccag ccagccggaa gggccgagcg cagaagtggt    4260
```

```
cctgcaactt tatccgcctc catccagtct attaattgtt gccgggaagc tagagtaagt    4320
agttcgccag ttaatagttt gcgcaacgtt gttgccattg ctacaggcat cgtggtgtca    4380
cgctcgtcgt ttggtatggc ttcattcagc tccggttccc aacgatcaag gcagagttaca   4440 tgatccccca tgttgtgcaa aaaagcggtt agctccttcg gtcctccgat cgttgtcaga    4500
agtaagttgg ccgcagtgtt atcactcatg gttatgcag cactgcataa ttctcttact     4560
gtcatgccat ccgtaagatg cttttctgtg actggtgagt actcaaccaa gtcattctga    4620
gaatagtgta tgcggcgacc gagttgctct gcccggcgt caacacggga taataccgcg     4680
ccacatagca gaactttaaa agtgctcatc attggaaaac gttcttcggg gcgaaaactc    4740
tcaaggatct taccgctgtt gagatccagt tcgatgtaac ccactcgtgc acccaactga    4800
tcttcagcat cttttacttt caccagcgtt tctgggtgag caaaaacagg aaggcaaaat    4860
gccgcaaaaa agggaataag ggcgacacgg aaatgttgaa tactcatact cttccttttt    4920
caatattatt gaagcattta tcagggttat tgtctcatga gcggatacat atttgaatgt    4980
atttagaaaa ataaacaaat aggggttccg cgcacatttc                          5020

<210> SEQ ID NO 8
<211> LENGTH: 83
<212> TYPE: DNA
<213> ORGANISM: Artificial Sequence
<220> FEATURE:
<223> OTHER INFORMATION: A sense strand for CREx2hb

<400> SEQUENCE: 8
cccaagcttg atatcgaatt cgacgtcaca gtatgacggc catgggaatt cgacgtcaca    60
gtatgacggc catggggatc ccg                                            83

<210> SEQ ID NO 9
<211> LENGTH: 83
<212> TYPE: DNA
<213> ORGANISM: Artificial Sequence
<220> FEATURE:
<223> OTHER INFORMATION: An antisense strand for CREx2hb

<400> SEQUENCE: 9
cgggatcccc atggccgtca tactgtgacg tcgaattccc atggccgtca tactgtgacg    60
tcgaattcga tatcaagctt ggg                                            83

<210> SEQ ID NO 10
<211> LENGTH: 78
<212> TYPE: DNA
<213> ORGANISM: Artificial Sequence
<220> FEATURE:
<223> OTHER INFORMATION: A sense strand for CREx2bp

<400> SEQUENCE: 10
tgcactgcag gaattcccat ggccgtcata ctgtgacgtc gaattcccat ggccgtcata    60
ctgtgacgtc ggatcccg                                                  78

<210> SEQ ID NO 11
<211> LENGTH: 78
<212> TYPE: DNA
<213> ORGANISM: Artificial Sequence
<220> FEATURE:
<223> OTHER INFORMATION: An antisense strand for CREx2bp

<400> SEQUENCE: 11
```

```
cgggatccga cgtcacagta tgacggccat gggaattcga cgtcacagta tgacggccat    60
gggaattcct gcagtgca                                                  78

<210> SEQ ID NO 12
<211> LENGTH: 30
<212> TYPE: DNA
<213> ORGANISM: Artificial Sequence
<220> FEATURE:
<223> OTHER INFORMATION: A sense primer

<400> SEQUENCE: 12
tcgactgcag cccatggccg tcatactgtg                                     30

<210> SEQ ID NO 13
<211> LENGTH: 30
<212> TYPE: DNA
<213> ORGANISM: Artificial Sequence
<220> FEATURE:
<223> OTHER INFORMATION: An antisense primer

<400> SEQUENCE: 13
tgcactgcag gtcggagctg actgttctgg                                     30

<210> SEQ ID NO 14
<211> LENGTH: 264
<212> TYPE: DNA
<213> ORGANISM: Artificial Sequence
<220> FEATURE:
<223> OTHER INFORMATION: Vasoactive intestinal peptide promoter

<400> SEQUENCE: 14
tcgactgcag cccatggccg tcatactgtg tgacgtcttt cagagcactt tgtgattgct    60
cagtcctaag tataagccct ataaaatgat gggctttgaa atgctggtca gggtagagtg   120
agaagcacca gcaggcagta acagccaacc cttagccatt gctaagggca gagaactggt   180
ggagcctttc tcttactccc aggacttcag cacctaagac agctccaaaa caaaccagaa   240
cagtcagctc cgacctgcag tgca                                          264
```